(12) United States Patent
Bolognesi et al.

(10) Patent No.: US 7,657,385 B2
(45) Date of Patent: Feb. 2, 2010

(54) STRUCTURE-BASED HEPATITIS C VIRUS DRUG DESIGN

(75) Inventors: Martino Bolognesi, Torre d'Isola (IT); Guido Grandi, Segrate (IT)

(73) Assignee: Novartis Vaccines and Diagnostics, S.R.L., Siena (IT)

( * ) Notice: Subject to any disclaimer, the term of this patent is extended or adjusted under 35 U.S.C. 154(b) by 342 days.

(21) Appl. No.: 10/312,490

(22) PCT Filed: Jul. 3, 2001

(86) PCT No.: PCT/IB01/01450

§ 371 (c)(1),
(2), (4) Date: Apr. 22, 2003

(87) PCT Pub. No.: WO02/02631

PCT Pub. Date: Jan. 10, 2002

(65) Prior Publication Data

US 2003/0176662 A1    Sep. 18, 2003

(30) Foreign Application Priority Data

Jul. 3, 2000    (GB)    .................... 0016361.8

(51) Int. Cl.
G01N 31/00    (2006.01)
G06F 19/00    (2006.01)
A61K 39/12    (2006.01)
C12N 7/00    (2006.01)
G01N 33/566    (2006.01)

(52) U.S. Cl. .................... 702/27; 702/19; 424/204.1; 435/235.1; 436/501

(58) Field of Classification Search .................... None
See application file for complete search history.

(56) References Cited

FOREIGN PATENT DOCUMENTS

WO    WO 99/18198    4/1999

OTHER PUBLICATIONS

IPER for WO 02/02632 (corresponding to PCT/IB01/01450), posted to ofi.epoline.org on Feb. 14, 2003.*
Geschwend et al. Journal of Molecular Recognition (1996) vol. 9, pp. 175-186.*
Higginbottom et al. Journal of Virology (Apr. 2000) vol. 74, No. 8, pp. 3642-3649.*
PDB file 1G8Q (submitted by Kitadokoro et al. Nov. 20, 2000).*
Kitadokoro et al. (EMBO J. (Jan. 2001) vol. 1-2, pp. 12-18).*
Kuntz et al., "A Geometric Approach to Macromolecule-Ligand Interactions" *J. Mol. Biol.* 161:269-288, 1982.
Petracca et al., "Structure-Function Analysis of Hepatitis C Virus Envelope-CD81 Binding" *J. Virology* 74(10):4824-4830, May 2000.
Pileri et al., "Binding of Hepatitis C Virus to CD81" *Science* 282:938-941, Oct. 1998.
Bisceglie, "Hepatitis C-Virology and Future Antiviral Targets" *American J. Medicine* 107(6B):45S-48S, Dec. 1999.
Kitakokoro et al., "Crystallization and Preliminary Crystallographic Studies on the Large Extracellular Domain of Human CD81, a Tetraspanin Receptor for Hepatitis C Virus" *Acta Cryst.* D57:156-158, 2001.
Lybrand et al., ."Ligand-Protein Docking and Rational Drug Design" *Current Opinion in Structural Biology* 5:224-228, 1995.

* cited by examiner

*Primary Examiner*—Lori A Clow
(74) *Attorney, Agent, or Firm*—Mark Seka; George Renzoni

(57) ABSTRACT

The extracellular loop of CD81 is a cellular receptor for the E2 protein of hepatitis C virus. A CD81 crystal structure has been elucidated and is provided for use in the structure-based design of compounds which bind to CD81 and thus block the binding of HCV. Methods such as docking and de novo drug design can be used.

11 Claims, 7 Drawing Sheets

SEQUENCE LISTING

<160> NUMBER OF SEQ ID NOS: 14

<210> SEQ ID NO 1
<211> LENGTH: 89
<212> TYPE: PRT
<213> ORGANISM: Human

<400> SEQUENCE: 1

Phe Val Asn Lys Asp Gln Ile Ala Lys Asp Val Lys Gln Phe Tyr Asp
1               5                   10                  15

Gln Ala Leu Gln Gln Ala Val Val Asp Asp Asp Ala Asn Asn Ala Lys
            20                  25                  30

Ala Val Val Lys Thr Phe His Glu Thr Leu Asp Cys Cys Gly Ser Ser
        35                  40                  45

Thr Leu Thr Ala Leu Thr Thr Ser Val Leu Lys Asn Asn Leu Cys Pro
    50                  55                  60

Ser Gly Ser Asn Ile Ile Ser Asn Leu Phe Lys Glu Asp Cys His Gln
65                  70                  75                  80

Lys Ile Asp Asp Leu Phe Ser Gly Lys
                85

<210> SEQ ID NO 2
<211> LENGTH: 89
<212> TYPE: PRT
<213> ORGANISM: Chimpanzee

<400> SEQUENCE: 2

Phe Val Asn Lys Asp Gln Ile Ala Lys Asp Val Lys Gln Phe Tyr Asp
1               5                   10                  15

Gln Ala Leu Gln Gln Ala Val Val Asp Asp Asp Ala Asn Asn Ala Lys
            20                  25                  30

Ala Val Val Lys Thr Phe His Glu Thr Leu Asp Cys Cys Gly Ser Ser
        35                  40                  45

Thr Leu Thr Ala Leu Thr Thr Ser Val Leu Lys Asn Asn Leu Cys Pro
    50                  55                  60

Ser Gly Ser Asn Ile Ile Ser Asn Leu Phe Lys Glu Asp Cys His Gln
65                  70                  75                  80

Lys Ile Asp Asp Phe Phe Ser Gly Lys
                85

<210> SEQ ID NO 3
<211> LENGTH: 89
<212> TYPE: PRT
<213> ORGANISM: Green monkey

<400> SEQUENCE: 3

Phe Val Asn Lys Asp Gln Ile Ala Lys Asp Val Lys Gln Phe Tyr Asp
1               5                   10                  15

Gln Ala Leu Gln Gln Ala Val Val Asp Asp Ala Asn Asn Ala Lys
            20                  25                  30

Ala Val Val Lys Thr Phe His Glu Thr Val Asp Cys Cys Gly Ser Ser
            35                  40                  45

Thr Leu Ala Ala Leu Thr Thr Ser Val Leu Lys Asn Asn Leu Cys Pro
    50                  55                  60

Ser Gly Ser Asn Ile Ile Ser Asn Leu Leu Lys Asp Cys His Gln
65                  70                  75                  80

Lys Ile Asp Asp Phe Phe Ser Gly Lys
                85

<210> SEQ ID NO 4
<211> LENGTH: 89
<212> TYPE: PRT
<213> ORGANISM: S.oedipus

<400> SEQUENCE: 4

Phe Val Asn Lys Asp Gln Ile Ala Lys Asp Val Lys Gln Phe Tyr Asp
1               5                   10                  15

Gln Ala Leu Gln Gln Ala Val Val Asp Asp Ala Asn Asn Ala Lys
            20                  25                  30

Ala Val Val Lys Thr Phe His Glu Thr Leu Asn Cys Cys Gly Ser Ser
            35                  40                  45

Thr Leu Ser Ala Leu Thr Thr Ser Met Leu Lys Asn Asn Leu Cys Pro
    50                  55                  60

Ser Gly Ser Ser Ile Ile Ser Asn Leu Phe Lys Glu Asp Cys His Gln
65                  70                  75                  80

Lys Ile Asp Glu Leu Phe Ser Gly Lys
                85

<210> SEQ ID NO 5
<211> LENGTH: 89
<212> TYPE: PRT
<213> ORGANISM: Hamster

<400> SEQUENCE: 5

Phe Val Asn Lys Asp Gln Ile Ala Lys Asp Val Lys Gln Phe Tyr Asp
1               5                   10                  15

Gln Ala Leu Gln Gln Ala Val Val Asp Asp Ala Asn Asn Ala Lys
            20                  25                  30

Ala Val Val Lys Thr Phe His Glu Thr Leu Asn Cys Cys Gly Ser Asn
            35                  40                  45

Ala Leu Thr Ala Leu Thr Thr Ser Val Leu Lys Asn Ser Leu Cys Pro
    50                  55                  60

Ser Gly Thr Asn Ile Phe Asn Ser Leu Met Lys Glu Asp Cys His Gln
65                  70                  75                  80

Lys Ile Asp Glu Leu Phe Ser Gly Lys
                85

```
<210> SEQ ID NO 6
<211> LENGTH: 89
<212> TYPE: PRT
<213> ORGANISM: Rat

<400> SEQUENCE: 6

Phe Val Asn Lys Asp Gln Ile Ala Lys Asp Val Lys Gln Phe Tyr Asp
1               5                   10                  15

Gln Ala Leu Gln Gln Ala Val Met Asp Asp Ala Asn Asn Ala Lys
            20                  25                  30

Ala Val Val Lys Thr Phe His Glu Thr Leu Asn Cys Cys Gly Ser Asn
            35                  40                  45

Thr Leu Thr Thr Leu Thr Thr Ala Val Leu Arg Asn Ser Leu Cys Pro
    50                  55                  60

Ser Ser Ser Asn Ser Phe Thr Gln Leu Leu Lys Glu Asp Cys His Gln
65                  70                  75                  80

Lys Ile Asp Glu Leu Phe Ser Gly Lys
                85

<210> SEQ ID NO 7
<211> LENGTH: 89
<212> TYPE: PRT
<213> ORGANISM: Mouse

<400> SEQUENCE: 7

Phe Val Asn Lys Asp Gln Ile Ala Lys Asp Val Lys Gln Phe Tyr Asp
1               5                   10                  15

Gln Ala Leu Gln Gln Ala Val Met Asp Asp Ala Asn Asn Ala Lys
            20                  25                  30

Ala Val Val Lys Thr Phe His Glu Thr Leu Asn Cys Cys Gly Ser Asn
            35                  40                  45

Ala Leu Thr Thr Leu Thr Thr Thr Ile Leu Arg Asn Thr Leu Cys Pro
    50                  55                  60

Ser Gly Gly Asn Ile Leu Thr Pro Leu Leu Gln Gln Asp Cys His Gln
65                  70                  75                  80

Lys Ile Asp Glu Leu Phe Ser Gly Lys
                85

<210> SEQ ID NO 8
<211> LENGTH: 82
<212> TYPE: PRT
<213> ORGANISM: Human

<400> SEQUENCE: 8

Tyr Ser His Lys Asp Glu Val Ile Lys Glu Val Gln Glu Phe Tyr Lys
1               5                   10                  15

Asp Thr Tyr Asn Lys Leu Lys Thr Lys Asp Glu Pro Gln Arg Glu Thr
            20                  25                  30

Leu Lys Ala Ile His Tyr Ala Leu Asn Cys Cys Gly Leu Ala Gly Gly
            35                  40                  45

Val Glu Gln Phe Ile Ser Asp Ile Cys Pro Lys Lys Asp Val Leu Glu
    50                  55                  60

Thr Phe Thr Val Lys Ser Cys Pro Asp Ala Ile Lys Glu Val Phe Asp
65                  70                  75                  80

Asn Lys

<210> SEQ ID NO 9
<211> LENGTH: 77
```

```
<212> TYPE: PRT
<213> ORGANISM: Human

<400> SEQUENCE: 9

Phe Ile Gly Lys Gly Val Ala Ile Arg His Val Gln Thr Met Tyr Glu
1               5                   10                  15

Glu Ala Tyr Asn Asp Tyr Leu Lys Asp Arg Gly Lys Gly Asn Gly Thr
                20                  25                  30

Leu Ile Thr Phe Pro Leu Gln His Phe Gln Cys Cys Gly Lys Glu Ser
            35                  40                  45

Ser Glu Gln Val Gln Pro Thr Cys Pro Lys Leu Leu Arg His Lys
50                  55                  60

Asn Cys Ile Asp Glu Ile Glu Thr Ile Ile Ser Val Lys
65                  70                  75

<210> SEQ ID NO 10
<211> LENGTH: 78
<212> TYPE: PRT
<213> ORGANISM: Mouse

<400> SEQUENCE: 10

Phe Val Tyr Glu Gln Lys Leu Asn Thr Leu Val Ala Glu Gly Leu Asn
1               5                   10                  15

Asp Ser Ile Gln His Tyr His Ser Asp Asn Ser Thr Met Lys Ala Trp
                20                  25                  30

Asp Phe Ile Gln Thr Gln Leu Gln Cys Cys Gly Val Asn Gly Ser Ser
            35                  40                  45

Asp Trp Thr Ser Gly Pro Pro Ser Ser Cys Pro Ser Gly Ala Asp Val
50                  55                  60

Gln Gly Cys Tyr Asn Lys Ala Lys Ser Trp Phe His Ser Asn
65                  70                  75

<210> SEQ ID NO 11
<211> LENGTH: 84
<212> TYPE: PRT
<213> ORGANISM: Human

<400> SEQUENCE: 11

Tyr Phe Asn Met Gly Lys Leu Lys Gln Glu Met Gly Gly Ile Val Thr
1               5                   10                  15

Glu Leu Ile Arg Asp Tyr Asn Ser Ser Arg Glu Asp Ser Leu Gln Asp
                20                  25                  30

Ala Trp Asp Tyr Val Gln Ala Gln Val Lys Cys Cys Gly Trp Val Ser
            35                  40                  45

Phe Tyr Asn Trp Thr Asp Asn Ala Glu Tyr Pro Cys Ser Cys Glu Val
            50                  55                  60

Lys Gly Glu Glu Asp Asn Ser Val Tyr Gln Gly Cys Met Glu Lys
65                  70                  75                  80

Val Gln Ala Trp

<210> SEQ ID NO 12
<211> LENGTH: 86
<212> TYPE: PRT
<213> ORGANISM: Human

<400> SEQUENCE: 12

Tyr Val Phe Arg Asp Lys Val Met Ser Glu Phe Asn Asn Asn Phe Arg
1               5                   10                  15
```

```
Gln Gln Met Glu Asn Tyr Pro Lys Asn Asn His Thr Ala Ser Ile Leu
            20                  25                  30

Asp Arg Met Gln Ala Asp Phe Lys Cys Cys Gly Ala Ala Asn Tyr Thr
        35                  40                  45

Asp Ser Met Ser Lys Asn Arg Val Pro Asp Ser Cys Cys Cys Gly Ile
    50                  55                  60

Asn Phe Asn Glu Lys Ile His Lys Glu Gly Cys Val Glu Lys Ile Gly
65                  70                  75                  80

Gly Trp Leu Arg Lys Asn
                85

<210> SEQ ID NO 13
<211> LENGTH: 86
<212> TYPE: PRT
<213> ORGANISM: Human

<400> SEQUENCE: 13

Phe Val Phe Arg His Glu Ile Lys Asp Thr Phe Leu Arg Thr Tyr Thr
1               5                   10                  15

Asp Ala Met Gln Thr Tyr Asn Gly Asn Asp Glu Arg Ser Arg Ala Val
            20                  25                  30

Asp His Val Gln Arg Ser Leu Ser Cys Cys Gly Val Gln Asn Tyr Thr
        35                  40                  45

Asn Trp Ser Thr Ser His Gly Ile Pro Pro Ser Cys Cys Cys Asn Pro
    50                  55                  60

Gln Asp Leu His Asn Leu Thr Gln Lys Gly Cys Tyr Asp Leu Val Thr
65                  70                  75                  80

Ser Phe Met Glu Thr Asn
                85

<210> SEQ ID NO 14
<211> LENGTH: 86
<212> TYPE: PRT
<213> ORGANISM: Human

<400> SEQUENCE: 14

Phe Val Phe Lys Asp Trp Ile Lys Asp Gln Leu Tyr Phe Phe Ile Asn
1               5                   10                  15

Asn Asn Ile Arg Ala Tyr Arg Asp Asp Ile Asp Leu Gln Asn Leu Ile
            20                  25                  30

Asp Phe Thr Gln Glu Tyr Trp Gln Cys Cys Gly Ala Thr Asp Ser Asn
        35                  40                  45

Ala Ser Arg Glu Arg Cys Gly Val Pro Phe Ser Cys Cys Thr Lys Asp
    50                  55                  60

Pro Ala Glu Asp Val Ile Tyr Thr Lys Gly Cys Val Pro Gln Phe Glu
65                  70                  75                  80

Lys Trp Leu Gln Asp Asn
                85
```

STRUCTURE-BASED HEPATITIS C VIRUS DRUG DESIGN

All documents cited herein are incorporated by reference in their entirety.

TECHNICAL FIELD

This invention is in the field of the use of structure-based drug design methods to identify compounds that bind to CD81, which is a cell-surface receptor for hepatitis C virus (HCV).

BACKGROUND ART

Chronic HCV infection occurs in about 3% of the world's population. It is a major cause of liver disease, but effective anti-HCV drugs are not yet available.

In October 1998, the extracellular loop of CD81 was reported as a cellular receptor for the E2 protein of HCV [1]. It is an object of the invention to facilitate rational structure-based drug design of chemical compounds that interact with CD81 to inhibit the binding of HCV.

DISCLOSURE OF THE INVENTION

The invention is based on the elucidation of a crystal structure for the large extracellular loop (LEL; amino acids 113-201) of human CD81. This facilitates structure-based design of compounds which bind to CD81 and thus block the binding of HCV.

The invention provides a computer-based method for identifying a ligand for CD81, comprising the steps of: (a) providing a 3D structural representation of the large extracellular loop of CD81 in a storage medium on a computer; and (b) using the computer to apply structure-based drug design techniques to the structural representation.

Structure-Based Drug Design Techniques

Structure-based drug design techniques can be applied to the structural representation of the LEL in order to identify compounds that interact with CD81 to block HCV binding. A variety of suitable techniques [e.g. ref. 2] are available to the skilled person.

Software packages for implementing molecular modelling techniques for use in structure-based drug design include SYBYL [3], AMBER [4], CERIUS$^2$ [5], INSIGHT II [5], CATALYST [5], QUANTA [5], HYPERCHEM [6], CHEM-SITE [7] etc.

This software can be used to determine binding surfaces of the LEL in order to reveal features such as van der Waals contacts, electrostatic interactions, and/or hydrogen bonding opportunities. These binding surfaces may be used as follows:

Docking

Docking aligns the 3D structures of two or more molecules to predict the conformation of a complex formed from the molecules [e.g. ref 8]. According to the present invention, molecules are docked with the LEL structure to assess their ability to interact with CD81.

Docking can be accomplished by either geometric matching of the ligand and its receptor or by minimising the energy of interaction. Geometric matching algorithms are preferred because of their relative speed.

Suitable docking algorithms include, but are not limited to:

DOCK.[9], the prototypical program for structure-based drug design.

AUTODOCK [10, 4], which docks ligands in a flexible manner to receptors using grid-based Monte Carlo simulated annealing. The flexible nature of the AUTODOCK procedure helps to avoid bias (e.g. in orientation and conformation of the ligand in the active site) introduced by the user researcher [11] because, whilst the starting conformation in a rigid docking is normally biased towards an minimum energy conformation of the ligand, the binding conformation may be of relatively high conformational energy [12].

MOE-DOCK [13], in which a simulated annealing search algorithm is used to flexibly dock ligands. A grid-based energy evaluation is used to score docked conformations.

FLExX [3], which docks conformationally flexible ligands into a binding site using an incremental construction algorithm that builds the ligand in the site. Docked conformations are scored based on the strength of ligand-receptor interactions.

GOLD [14], a genetic algorithm for flexible ligand docking, with full ligand and partial protein flexibility. Energy functions are partly based on conformation and non-bonded contact information.

AFFINITY [5], which uses a two step process to dock ligands. First, initial placements of the ligand within the receptor are made using a Monte Carlo type procedure to search both conformational and Cartesian space. Second, a simulated annealing phase optimises the location of each ligand placement. During this phase, AFFINITY holds the 'bulk' of the receptor (atoms not in the binding site) rigid, while the binding site atoms and ligand atoms are movable.

$C^2$.LigandFit [5], which uses the energy of the ligand-receptor complex to automatically find best binding modes. Stochastic conformational search technique are used, and the best results from the conformational sampling are retained. A grid method is used to evaluate non-bonded interactions between the rigid receptor and the flexible ligand atoms.

Preferably, the docking algorithm is used, in a 'high throughput' mode, in which members of large structural libraries of potential ligands are screened against the receptor structure [15].

Suitable structural libraries include the ACD (Available Chemical Directory, from MDL Inc), AsInEx, Bionet, ComGenex, the Derwent World Drug Index (WDI), the Contact Service Company database, LaboTest, ChemBridge Express Pick, ChemStar, BioByteMasterFile, Orion, SALOR, TRIAD, ILIAD, the National Cancer Institute database (NCI), and the Aldrich, Fluka, Sigman and Maybridge catalogs. These are commercially available (e.g. the *HTS Chemicals* collections from Oxford Molecular, or the LeadQuest™ files from Tripos).

Pharmacophore hypotheses

A pharmacophore (i.e. a collection of chemical features and 3D constraints that expresses specific characteristics responsible for activity) can be defined for the LEL. The pharmacophore preferably includes surface-accessible features, more preferably including hydrogen bond donors and acceptors, charged/ionisable groups, and/or hydrophobic patches. These may be weighted depending on their relative importance in conferring activity [16].

Pharmacophores can be determined using software such as CATALYST (including HypoGen or HipHop) [5], CERIUS2, or constructed by hand from a known conformation of a lead compound. The pharmacophore can be used to screen structural libraries, using a program such as CATALYST [5]. The CLIX program [17] can also be used, which searches for orientations of candidate molecules in structural databases that yield maximum spatial coincidence with chemical groups which interact with the receptor.

de novo Compound Design

The binding surface or pharmacophore of the LEL can be used to map favourable interaction positions for functional groups (e.g. protons, hydroxyl groups, amine groups, hydrophobic groups and/or divalent cations) or small molecule fragments. Compounds can then be designed de novo in which the relevant functional groups are located in the correct spatial relationship to interact with CD81.

Once functional groups or small molecule fragments which can interact with specific sites in the CD81 binding surface have been identified, they can be linked in a single compound using either bridging fragments with the correct size and geometry or frameworks which can support the functional groups at favourable orientations, thereby providing a compound according to the invention. Whilst linking of functional groups in this way can be done manually, perhaps with the help of software such as QUANTA or SYBYL, automated or semi-automated de novo design approaches are also available:

MCDLNG [18], which fills a receptor binding site with a close-packed array of generic atoms and uses a Monte Carlo procedure to randomly vary atom types, positions, bonding arrangements and other properties.

MCSS/HOOK [19, 20, 5], which links multiple functional groups with molecular templates taken from a database.

LUDI [21, 5], which computes the points of interaction that would ideally be fulfilled by a ligand, places fragments in the binding site based on their ability to interact with the receptor, and then connects them to produce a ligand.

GROW [22], which starts with an initial 'seed' fragment (placed manually or automatically) and grows the ligand outwards.

SPROUT [23], suite which includes modules to: identify favourable hydrogen bonding and hydrophobic regions within a binding pocket (HIPPO module); select functional groups and position them at target sites to form starting fragments for structure generation (EleFAnT); generate skeletons that satisfy the steric constraints of the binding pocket by growing spacer fragments onto the start fragments and then connecting the resulting part skeletons (SPIDeR); substitute hetero atoms into the skeletons to generate molecules with the electrostatic properties that are complementary to those of the receptor site (MARABOU). The solutions can be clustered and scored using the ALLigaTOR module.

LEAPFROG [3], which evaluates ligands by making small stepwise structural changes and rapidly evaluating the binding energy of the new compound. Changes are kept or discarded based on the altered binding energy, and structures evolve to increase the interaction energy with the receptor.

GROUPBUILD [24], which uses a library of common organic templates and a complete empirical force field description of the non-bonding interactions between a ligand and receptor to construct ligands that have chemically reasonable structure and have steric and electrostatic properties complimentary to the receptor binding site.

CAVEAT [25], which designs linking units to constrain acyclic molecules.

RASSE [26]

The LEL Binding Site

To simplify computational complexity, algorithms for docking and ligand design will typically focus only on the binding site of a receptor—it is pointless to attempt to dock a ligand with a region in the receptor which is known not to be involved. Binding site identification is included in some algorithms (e.g. $C^2$.LigandFit, the 'Binding Site Analysis' module of INSIGHT II, the SPHGEN routine of DOCK). Some manual guidance may be required (e.g. AFFINITY).

Where a binding site has to be defined for the CD81-LEL, this should include amino acid residue Phe186. It may also include one or more of Leu154, Thr163, Ile181, Ile182, Leu185, Glu188, and Asp196. The binding site may include the whole of helix D.

The Structural Representation

The invention involves the use of a 3D structural representation of the LEL. This may be a representation of (a) the complete LEL, (b) a fragment of CD81 that comprises the LEL, or (c) a fragment of the LEL which includes the amino acids which interact with HCV E2 protein.

The structural representation is preferably based on or derived from the atomic co-ordinates cd81lel.pdb as set out herein, which represents the LEL dimer [see also refs. 27, 28 & 29]. Suitable structural representations include 3D models and molecular surfaces derived from these atomic co-ordinates.

Variants of cd81lel.pdb can also be used for the invention, such as variants in which the r.m.s. deviation of the x, y and z co-ordinates for all heavy (i.e. not hydrogen) atoms are all less than 2.5 Å (e.g. less than 2 Å, preferably less than 1 Å, and more preferably less than 0.5 Å or less than 0.1 Å) compared with cd81lel.pdb. Co-ordinate transformations which retain the 3D spatial relationships of atoms may also be used to give suitable variants.

Preferred fragments of the LEL whose co-ordinates can be used in the invention include amino acid residue Phe186. The fragments may also include one or more of Leu154, Thr163, Ile181, Ile182, Leu185, Glu188, and Asp196.

It is preferred that the methods of the invention use only one protein chain i.e. only of the monomers in cd81lel.pdb. Where only one monomer is used, it is preferred to use the first monomer (residues 113-202) rather than the second (residues 213-302).

The water molecules in cd81lel.pdb can optionally be omitted when performing the methods of the invention.

The atomic co-ordinates given herein can also be used as the basis of models of further protein structures. For example, a homology model could be based on the LEL structure of the present invention. The co-ordinates can also be used in the solution or refinement of further crystal structures of CD81.

The Storage Medium

The storage medium in which the LEL structural representation is provided is preferably random-access memory (RAM), but may also be read-only memory (ROM e.g. CDROM), or a diskette. The storage medium may be local to the computer, or may be remote (e.g. a networked storage medium, including the internet).

The invention also provides a computer-readable medium for a computer, characterised in that the medium contains atomic co-ordinates and/or a 3D structural representation of the LEL of CD81. The atomic co-ordinates are preferably cd81lel.pdb or variants thereof.

Any suitable computer can be used in the present invention.

Testing Compounds

The methods may comprise the further steps of: (c) providing a compound identified by said structure-based drug design techniques; and (d) contacting said compound with CD81, or a fragment thereof containing the LEL, and assaying the interaction between them.

The assay may be of a competitive nature. For example, the assay may include HCV E2 protein (either purified, or in the context of the HCV virion), such that E2 and the compound compete for binding to CD81.

Compounds and Their Uses

The methods of the invention identify compounds that can interact with CD81. These compounds may be designed de novo, may be known compounds, or may be based on known compounds. The compounds may be useful pharmaceuticals themselves, or may be prototypes which can be used for further pharmaceutical refinement (i.e. lead compounds) in order to improve binding affinity or other pharmacologically important features (e.g. bio-availability, toxicology, metabolism, pharmacokinetics etc.).

The invention thus provides: (i) a compound identified using the methods of the invention; (ii) a compound identified using the methods of the invention for use as a pharmaceutical; (iii) the use of a compound identified using the methods of the invention in the manufacture of a medicament for treating hepatitis C infection; and (iv) a method of treating a patient with hepatitis C infection, comprising administering an effective amount of a compound identified using the methods of the invention.

These compounds preferably interact with CD81 with a binding constant in the micromolar or, more preferably, nanomolar range or stronger.

As well as being useful compounds individually, ligands identified in silico by the structure-based design techniques can also be used to suggest libraries of compounds for 'traditional' in vitro or in vivo screening methods. Important pharmaceutical motifs in the ligands can be identified and mimicked in compound libraries (e.g. combinatorial libraries) for screening for CD81-binding activity.

Crystals

The invention also provides a composition comprising an extracellular region (e.g. the LEL) of CD81 in crystalline form. The crystal can be used for diffraction studies e.g. X-ray or neutron diffraction.

The crystal is preferably in the monoclinic space group $P2_1$ (a=31.5 Å, b=77.2 Å, c=38.5 Å, β=107.4°), with two molecules per asymmetric unit (Vm of 2.16 Å$^3$/dalton).

In some embodiments, the composition may include ligands which are co-crystallised with the CD81 fragment; in other embodiments the composition may be essentially pure protein.

BRIEF DESCRIPTION OF DRAWINGS

The patent or application file contains at least one drawing executed in color. Copies of this patent or patent application publication with color drawing(s) will be provided by the Office upon request and payment of the necessary fee.

MODES FOR CARRYING OUT THE INVENTION

CD81-LEL Production

CD81-LEL was purified from a recombinant *E. coli* strain as a fusion protein with the IgG binding domain of the *S. aureus* protein A. After purification of the chimeric protein, CD81-LEL was separated from the fusion by specific protease cleavage and further purified for the crystallization experiments. The purified protein was fully active as judged by the recombinant E2/CD81 inhibition of binding assay [1].

CD81-LEL Crystallisation

Crystals of CD81-LEL were obtained by mixing purified CD81-LEL at 10 mg/mil with 0.1M MES buffer (pH 6.0), 0.1M sodium chloride, and 10% PEG4000. The crystals belong to the monoclinic space group $P2_1$ (a=31.5 Å, b=77.2

Å, c=38.5 Å, β=107.4°), with two molecules per asymmetric unit (Vm of 2.16 Å$^3$/dalton). Crystals were flash-cooled at 100K with addition of 20% glycerol as cryoprotectant.

Whilst native crystals could be obtained easily, it was difficult to obtain suitable heavy atom derivatives for multiple isomorphous replacement techniques.

Three suitable derivatives were eventually produced, based on Lu, Hg and Pt:

at 1.60 Å resolution. No residues are found in disallowed regions of the Ramachandran plot. Residues 238-241 are disordered in a A'B'loop.

Analysis of the Crystal Structure

Figure 1A:
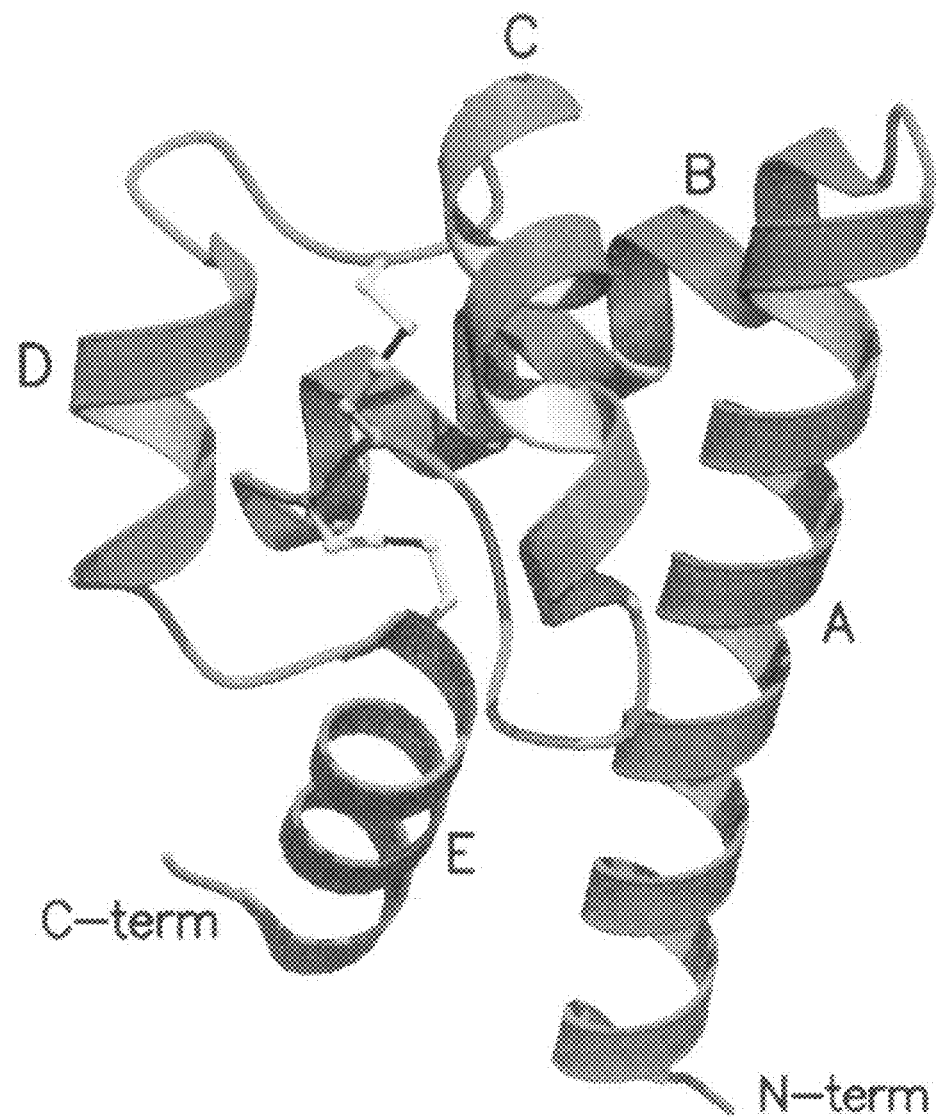
FIG. 1 shows: (1A) the CD81-LEL isolated chain tertiary structure, highlighting the head domain localisation relative to the N- and C-terminal helices (α-helices A and E, respectively), and the labelling of secondary structure elements. The two disulphide bridges are shown by yellow bonds; (1B) the dimeric CD81-LEL, showing the two subunits in blue and purple, with the helix labels distinguished by a symbol. The molecular two-fold axis is close to vertical, and located between the N- and C-termini of the two chains. Solid dots in the purple subunit trace an approximate path for the loops not observable in the electron density maps. (1C) A GRASP view of the molecular surface of the CD81-LEL dimer, in an orientation corresponding that of the blue subunit in panel 1A. This orientation brings α-helices C and D in the foreground; they can be recognised by comparison to panel A and by the low polarity region (white colour) in the upper part of the molecular surface.

FIG. 1A shows the CD81-LEL tertiary structure, which is essentially composed of five α-helices (A, B, C, D, E) spanning residues Asn115-Asp137, Ala140-Asp155, Leu165-

| Parameter | Native 1 | LuCl$_3$ | Hg(Ac)$_2$ | K$_2$PtCl$_6$ | Native 2 |
|---|---|---|---|---|---|
| Diffraction data | | | | | |
| Wavelength (Å) | 1.54 | 1.54 | 1.54 | 1.54 | 0.93 |
| Resolution (Å) | 2.7 | 2.7 | 3.0 | 3.3 | 1.6 |
| Unique reflections | 5136 | 4979 | 3619 | 2521 | 21557 |
| R$_{merge}$ (%) | 5.8 | 6.0 | 8.4 | 4.4 | 3.8 |
| Completeness (%) | 99.7 | 98.0 | 98.1 | 91.8 | 98.0 |
| | (99.4) | (93.4) | (97.1) | (87.5) | (93.1) |
| Redundancy | 3.4 | 2.0 | 3.2 | 8.2 | 6.9 |
| MIR phasing | | | | | |
| Phasing power/R$_{cullis}$ | | | | | |
| (acentric) | | 1.49/0.78 | 1.25/0.84 | 1.30/0.87 | |
| (centric) | | 1.16/0.82 | 0.98/0.85 | 0.90/0.89 | |
| (anom) | | 0.95/0.97 | 0.66/0.99 | 0.65/0.99 | |
| Overall FOM (acentric/centric) | | | 0.63/0.58 | | |
| Refinement | | | | | |
| Resolution range | | | | | 20.0-1.6 |
| R$_{factor}$/R$_{free}$ (%) | | | | | 18.7/23.8 |
| No. of protein atoms | | | | | 1345 |
| No. of solvent atoms | | | | | 194 |
| Ramachandran distribution | | | | | |
| % core | | | | | 92.4 |
| % allowed | | | | | 7.6 |
| % generous | | | | | 0.0 |
| % disallowed | | | | | 0.0 |
| r.m.s. bonds (Å) | | | | | 0.006 |
| r.m.s. angles (°) | | | | | 1.2 |
| Average B values (Å$^2$) | | | | | 35.2 |

NB:
R$_{merge}$ = Σ| Ii − <Ii> |/Σ <Ii>, where Ii is the observed intensity and <Ii> is the average intensity over symmetry equivalent measurements.
Phasing power = Σ |F$_H$|/Σ | |F$_{PH}$(obs)| − |F$_{PH}$(calc)| |, where F$_{PH}$ and F$_H$ are the derivative and calculated heavy-atom structure factors, respectively.
R$_{cullis}$ = Σ | |F$_{PH}$ − F$_P$| − |F$_H$(calc)|/|F$_{PH}$ − F$_P$|, where F$_{PH}$, F$_P$ and F$_H$ are the derivative, native and calculated heavy-atom structure factors, respectively.
R$_{factor}$ = Σ |F$_{obs}$| − |F$_{calc}$| |/Σ |F$_{obs}$|, R$_{free}$ is the same as R$_{factor}$, but for a 5% subset of all reflections that were never used in crystallographic refinement.
FOM (FIG. of merit) = |F(hkl)best/|F(hkl)|
Completeness is reported for all reflection and for the highest resolution shell.

Diffraction and Structure Solving

Native and derivative diffraction data were collected in house. Additional native data (at 1.6 Å resolution) were collected on beamline ID14 (ESRF, Grenoble, France), on a MAR CCD detector. All data were processed using DENZO and SCALEPACK [31] and merged using the CCP4 program suite [32]. Crystallographic phases were calculated with CCP4 programs and refined using SHARP [33] and SOLOMON [34]. The resulting electron density maps allowed about 80% of the two independent molecules to be traced. Model building and inspection was based on the O suite [35]. The structure was refined using CNS [36] and REFMAC [37]0.5% of the unique data were used to monitor the free R-factor. The final values for general R-factor and free R-factor are 18.7% and 23.8%, respectively. The refined model consists of 176 amino acids, with 194 water molecules, Asn172, Asn180-Phe186 and Asp189-Gly200, respectively (amino acids numbered according to the full CD81 sequence; refs 38 & 39). A short 3$_{10}$ helical segment covers residues Leu162-Ala164. The anti-parallel A- and E-helices can be seen as the stalk of a mushroom-shaped molecule, whose head domain (about 60 residues) is built by packing of the shorter B-, C- and D-helices and their intervening loops (loops are defined by the helices they connect i.e. AB, . . . , DE). A DALI search [40] of 3D protein structures did not show significant structural homology of the CD81-LEL fold to any known protein tertiary structure.

Figure 1B:
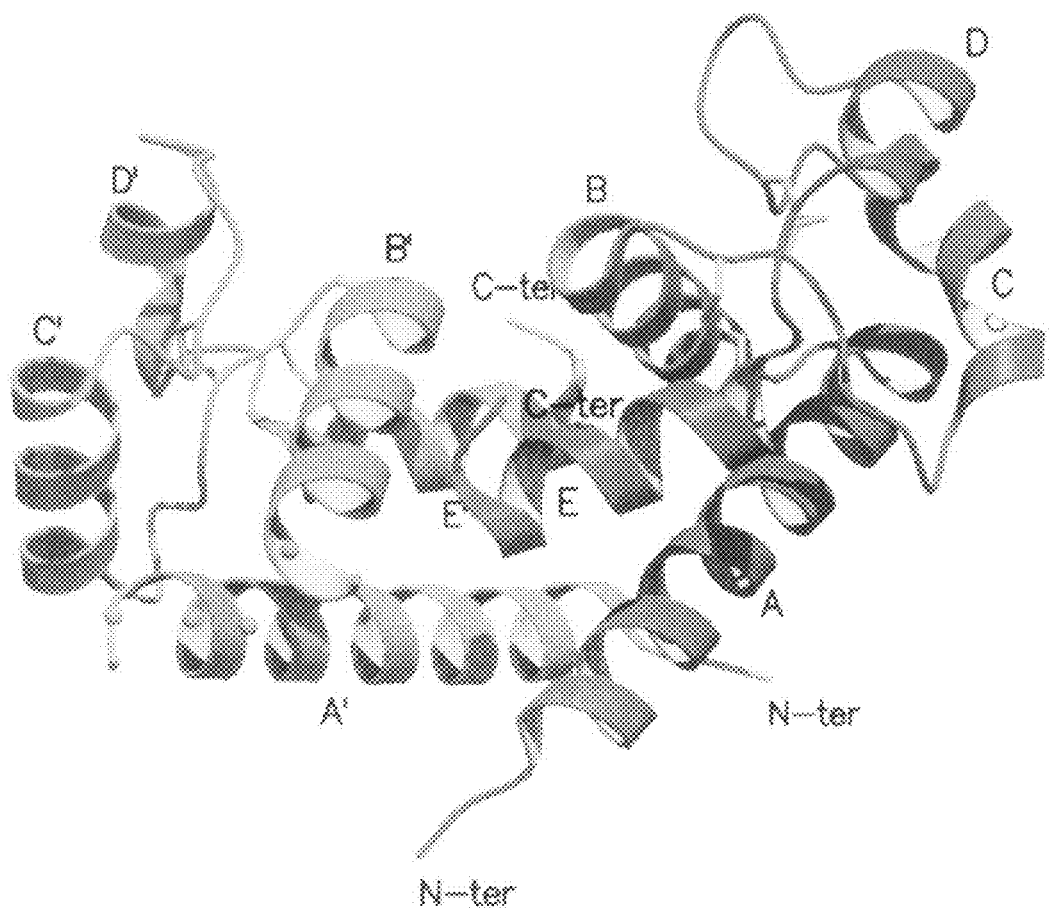

The dimeric assembly observed in the crystallographic asymmetric unit is shown in FIG. 1B. Two CD81-LEL chains assemble around a local two-fold axis, displaying intermolecular contacts mainly at the A:A' helix interface (a ' symbol distinguishes features of the partner subunit) and along the B-helix, which is in contact with the C-terminal region of the facing protomer. The subunit interface (986 Å$^2$) is composed of apolar residues for about 70% of its contact region.

The A:A' interface segment involves primarily residues Val114, Ile119, Val123, Gln125, Phe126 and Gln129, in both antiparallel helices, together with solvent mediated interactions between exposed polar side chains at the rim of the contact region. The second interface region includes residues Asn142, Val146, Thr149, Phe150, Thr153 & Leu154 which contact Leu197', Phe198', Ser199' & Gly200'. No water molecules are buried at the association interface.

Bivalent molecules (such as specific antibodies) capable of recognising human CD81 have been reported to have a higher affinity than E2 for CD81 [41]. In agreement with the crystal structure, this suggests that CD81 exists as a homodimeric species at the cell surface. In the crystal structure, the distance between the D- and D'-helices is about 30 Å, close to the distance between antigen-binding sites in an assembled antibody molecule.

The C-terminal His-tag does not appear to have a structural influence because the proximity of N- and C-termini within each chain, permitted by the antiparallel arrangement of A- and E-helices, is compatible with their topological location between TM3 and TM4 of native CD81 [39]. Moreover, due to the quaternary structure two-fold symmetry, the N- and C-termini of the two protomers fall in a restricted area, but on opposite faces of the assembled dimer (FIG. 1B). This quaternary organization is compatible with inter- and intra-cellular aggregation of CD81 in homo-dimeric species, through the association interface described.

Figure 1C:
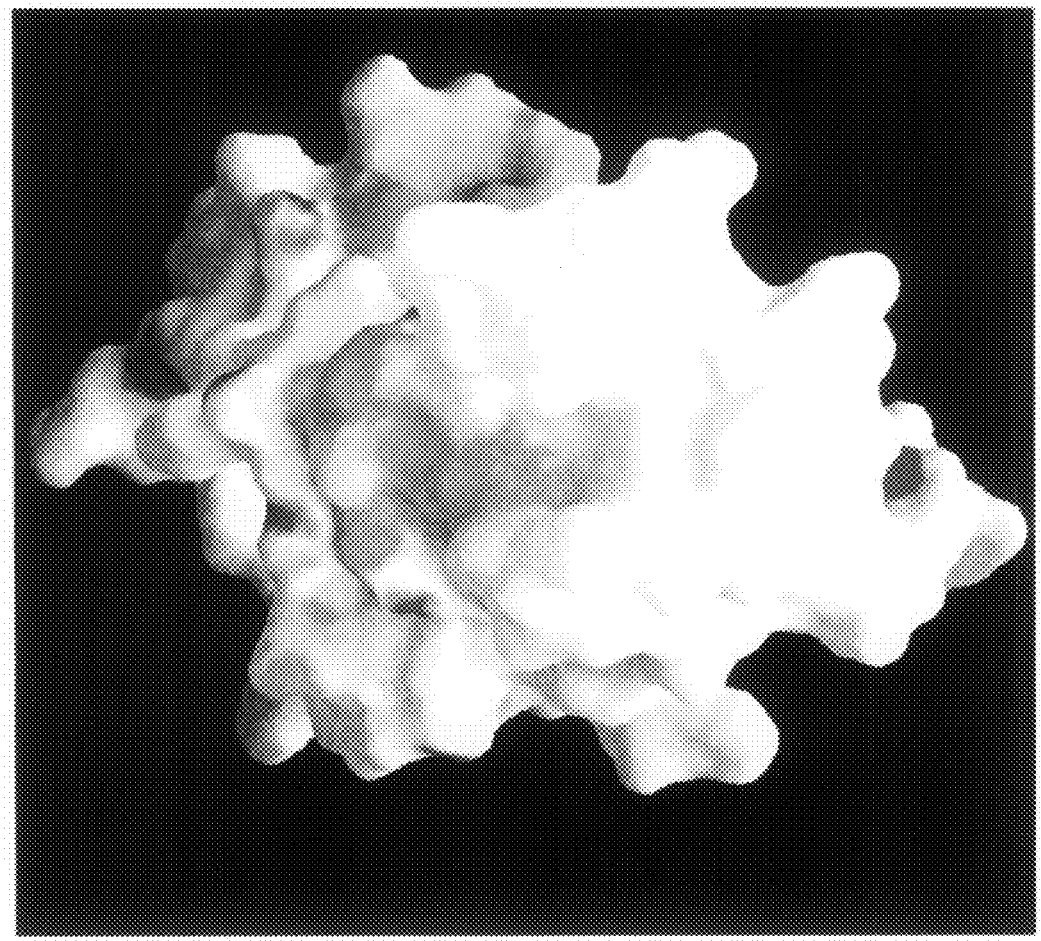

The overall shape of the CD81-LEL dimer is further characterized in FIG. 1C, as a surface displaying electrostatic potential. Besides the localization of negative potential in the central region of the dimer, a low polarity patch is present in a surface region comprising the C- and D-helices. In the crystal packing this region is virtually solvent inaccessible, due to extended contacts with a symmetry equivalent dimer.

Figure 3A:
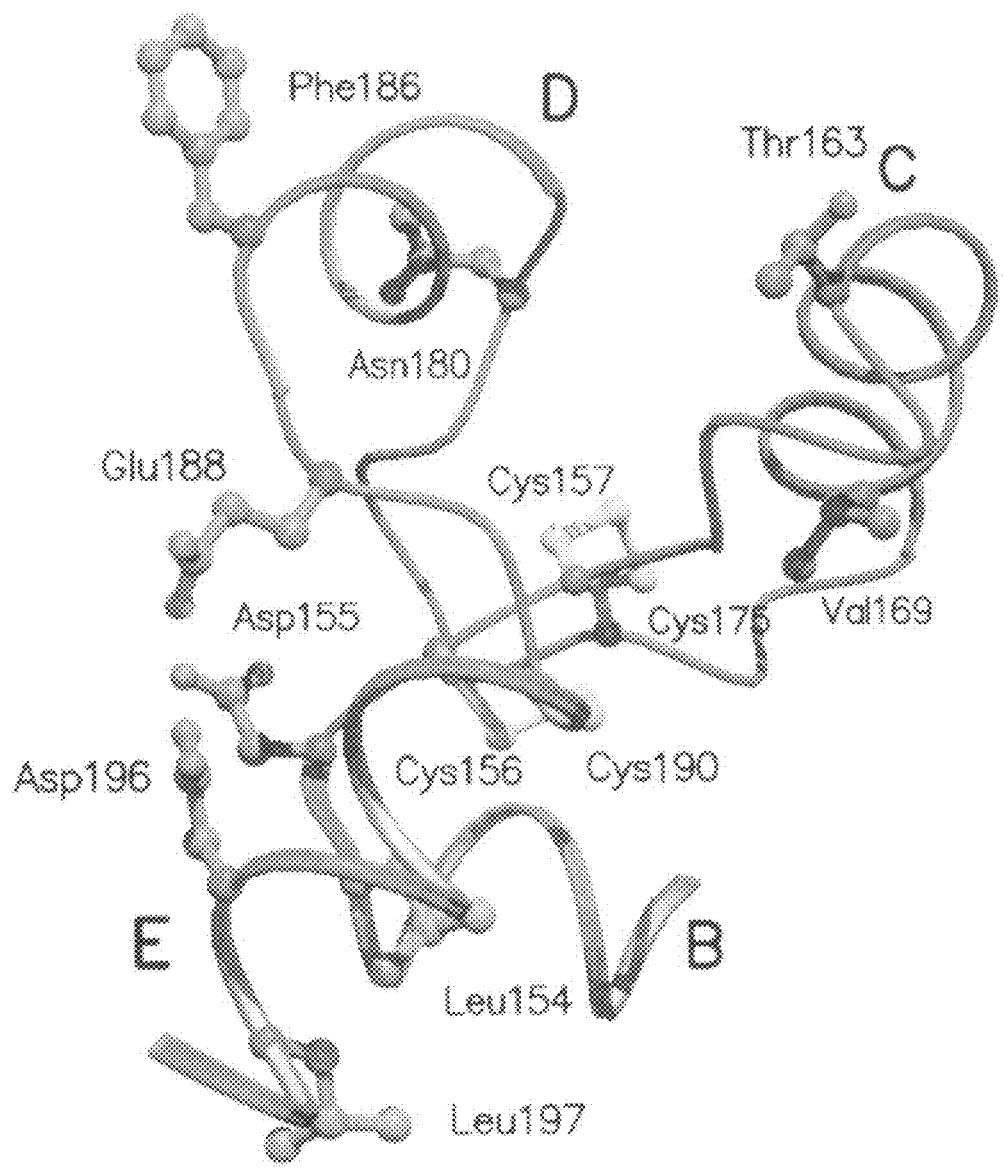
FIG. 3 shows: (3A) a schematic view of the location of Cys156--Cys190 and Cys157--Cys175 disulphide bridges (yellow bonds) within the head domain of CD81-LEL. The additional residues displayed are the sites of mutation observed in AGM CD81-LEL (green) and in tamarin CD81-LEL (red); (3B) the residues surrounding Tyr127, the head domain core, including electron density for the two disulphide bridges; (3C) a molecular surface representation of the CD81-LEL dimer, showing mutation sites 163, 186 and 196 (green patches) which have been shown to affect binding to HCV E2. Phe196 is in the upper-right part of the figure.

The CD81-LEL head domain is essentially composed of the last two turns of the A-helix, the B-, C-, D-helices, the intervening segments, and the DE loop. The domain fold is firstly stabilized by two tetraspanin-invariant intramolecular disulfide bridges [1, 38, 39, 41], which originate from two adjacent Cys residues (156 & 157) and are oriented approximately in opposite directions within the head domain (FIG. 3A). Their topological connections are Cys156--Cys190 and Cys157--Cys175: the first involves residues located at the C-terminus of the B-helix (Cys156) and at the N-terminus of the E-helix (Cys190); the second connects the BC segment (Cys157) with the CD loop region (Cys175). The latter region is fully exposed to solvent and specifically kinked towards the head domain core by virtue of the Cys157—Cys175 bridge. Of the four Cys residues, only Cys 175 is partly accessible to solvent (20 Å$^2$).

The head domain is built around the core residue Tyr127, fully buried and surrounded by Leu131, Val147, Phe150, His151 and by the. Asp128--His191 hydrogen-bonded salt-bridge. Tyr127 OH atom is hydrogen-bonded to His151 NE2 atom (2.7 Å) and is 3.61 Å from the Cys190Sγ atom (FIG. 3B). The imidazole ring of His151 is nestled between the two disulfide bridges, and is at hydrogen-bonding distance from Cys190 Sγ (3.56 Å). A hydrogen-bonding network involving Tyr127, His151 and Cys190 may play a role in regulating the redox properties of one or both disulfide bridges. Tyr127 is strictly conserved between species in CD81 (FIG. 2), and in all the CD9 sequences known to date; residue 191 is either His or Gln in amino acid sequences representing different tetraspanin sub-families (FIG. 2).

Sequence database surveys show that the tetraspanin family is composed of several sub-families (CD9, CD37, CD63, CD53, CD82, CD151 and others; ref. 38), for a total of about 160 amino acid sequences currently recognized. Among these, CD81 and CD9 families display close sequence (and thus structural) homology (23% residue identities are observed between human CD81-LEL and human CD9-LEL). FIG. 2 shows multiple amino acid sequence alignments of CD81-LEL from seven different species, together with human CD9-LEL and other tetraspanins. Sequence-based dendrogram analysis indicates that, within the sequences included in FIG. 2, human CD82-LEL is the one most distantly related to CD81-LEL (only 9% identical residues).

Figure 2:
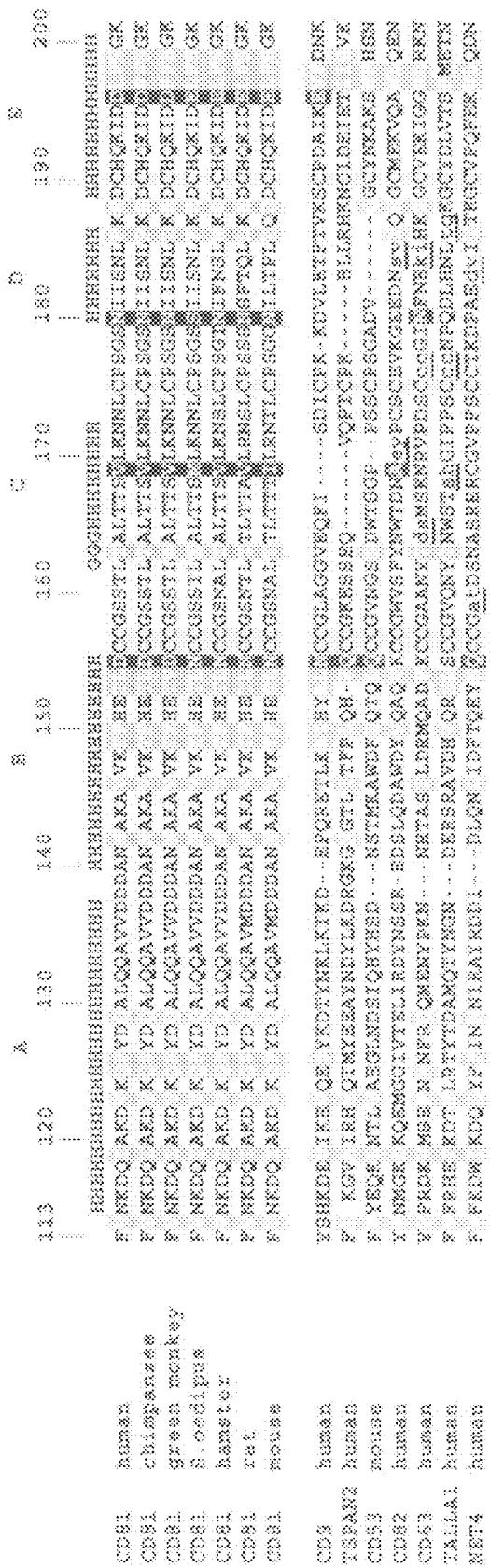
FIG. 2 shows an amino acid sequence alignment of LEL segments from mammalian CD81 and other tetraspanins. A symbol indicating the secondary structure [PROCHECK, ref. 30; H=α-helix; G=$3_{10}$ helix) is shown on the top line. On the leftmost column, name and organism are indicated. The accession numbers for the sequences used in the alignment are: human CD81, NP_004347; *Saguinus oedipus*, CAB89875; rat, NP_037219; mouse, P35762; human CD9, NP_001760; human TSPAN2, NP_005716; mouse CD53, NP 031677; human CD82, NP_002222; human CD63, NP_001771; human TALLA1, AAF4412; human NET4, AAC17120. Amino acid sequences of CD81 from chimpanzee, green monkey, and hamster have been obtained from ref. 1. The last four sequences contain insertions which have not been included in the alignment to avoid the introduction of long gaps, located between pairs of underlined residues. In detail, the insertion stretches are: in CD82 eLMNRPEVTy and sLSVRKGFCEAPGNRTQSGNHPEDWPv; in CD63, dWEKPs, cINVTVGc and kAi; in TALLA1, sPYFLEh, cMNETDc and tVAATKVNq; in NET4, aFGADDWNLNIYFNt and dVINTQCGYDARQKPEVDQQIv. The conserved Cys residues are enclosed in yellow boxes. Amino acids involved in the association interface are shown in pink boxes. The residues which are different between hCD81-LEL and agmCD81-LEL or tamCD81-LEL are marked in green or blue, respectively. Note that residue 163 is mutated in agmCD81-LEL and in tamCD81-LEL.
Figure 3B:
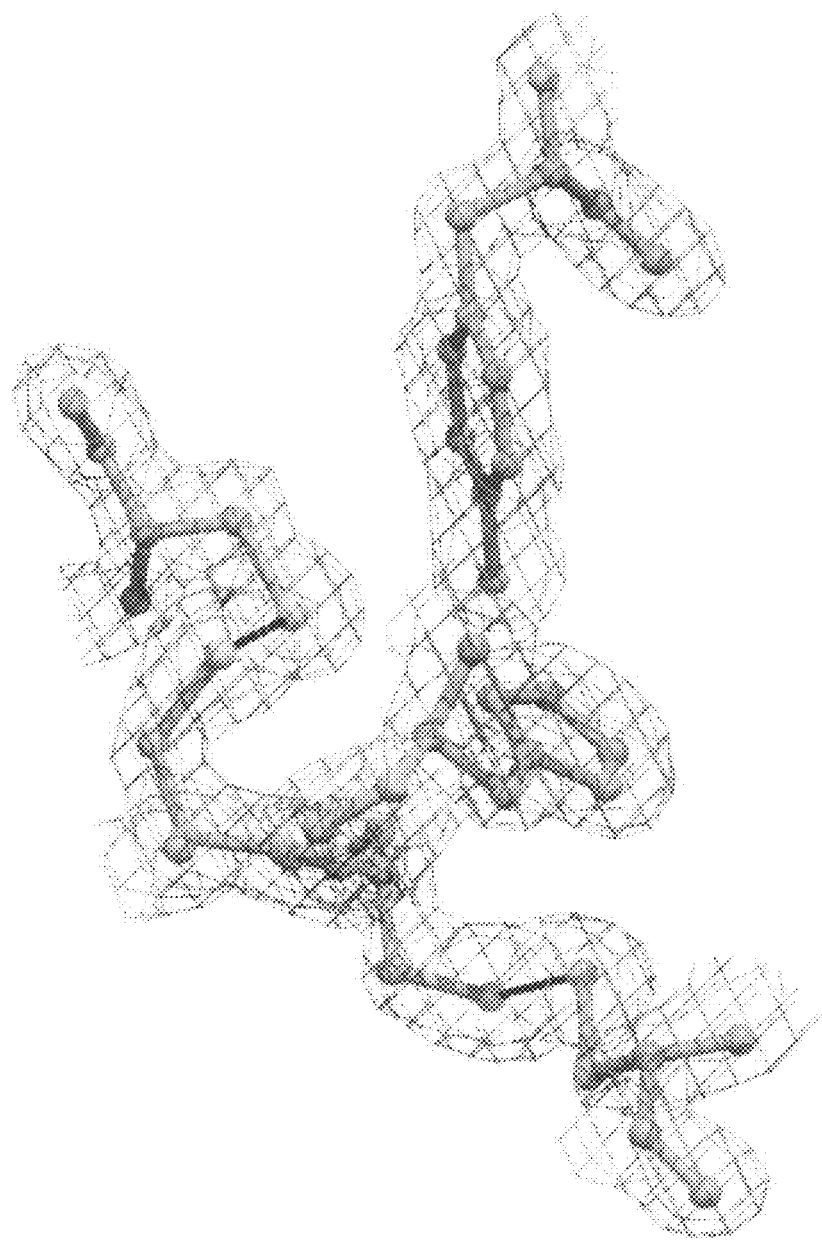

Besides the clearly recognized tetraspanin four-Cys consensus motif, inspection of the CD81 and CD9 alignment in FIG. 2 shows strict residue conservation at thirteen residues. Among these, four are charged amino acids (Lys116, Asp117, Lys148, and Lys201), which are totally solvent exposed in the assembled CD81-LEL dimer. The remaining nine conserved residues can be divided into three structural classes:

(a) Tyr127, His151 and Ile194 are buried residues involved in intramolecular interactions stabilizing the head domain and its contacts to the E-helix, as described above.

(b) Val123, Phe126, Leu154 and Phe198, which are primarily involved in subunit interface contacts, together with residues Ile119 and Phe150, conservatively substituted at the association interface. Conservation of the interface hydrophobic residues can be recognized throughout the sequence alignment of FIG. 2, suggesting that the observed subunit interface has a general functional significance for both homo- or hetero-dimeric tetraspanin association related to intra- or inter-cellular recognition processes.

(c) Gly158 and Pro176, both of which display unique positions and conformations (as indicated by their Ramachandran Φ,Ψ pairs) within the head domain fold, occurring after the Cys156-Cys157 pair and after Cys175. The selection of Gly and Pro at sites 158 and 176, respectively, may be required by the structural constraints imposed on the CD loop by the Cys157-Cys175 bridge, coding its specific kink towards the B-helix.

Analysis of the available sequences indicates that tetraspanin LEL segments display enhanced residue variability, deletions or insertions in the protein segments 158-174 and 176-189, which are comprised between the two disulfide bridges (see FIG. 2). The two segments span the BC loop, the C- and the D-helices and the DE hinge i.e. mostly solvent-exposed regions of the head domain (see FIGS. 1B & 3A). The structural location and sequence variability of this protein region, as opposed to generally conserved protein interface and core regions, suggests its involvement in species- or tetraspanin-specific recognition processes.

No binding of the HCV E2 glycoprotein to african green monkey (*Chlorocebus aethiops*) CD81 has been observed, but the LELs of human and AGM CD81 differ at only five residues: 154, 163, 186, 188 and 197 [1]. Conversely, E2 does bind to tamarin (*Saguinus oedipus*) CD81 with high affinity, and it differs from human CD81 only at residues 155, 163, 169, 180 and 196. Three of the AGM mutations have been engineered into human CD81-LEL and their binding properties versus recombinant E2 and anti-CD81 antibodies have been analysed in vitro [41]. Phe186 is the most critical residue affecting E2 binding, since the F186A mutation in human CD81-LEL fully impairs binding to E2 and to specific antibodies, the introduction of Phe186 in AGM CD81-LEL restores E2 binding, and tamarin CD81 displays Phe186 [1, 41, 42]. The Thr163Ala mutation marginally improves human CD81 binding to E2, whereas Asp196Glu mutation decreases binding to E2 [41].

Figure 3C:
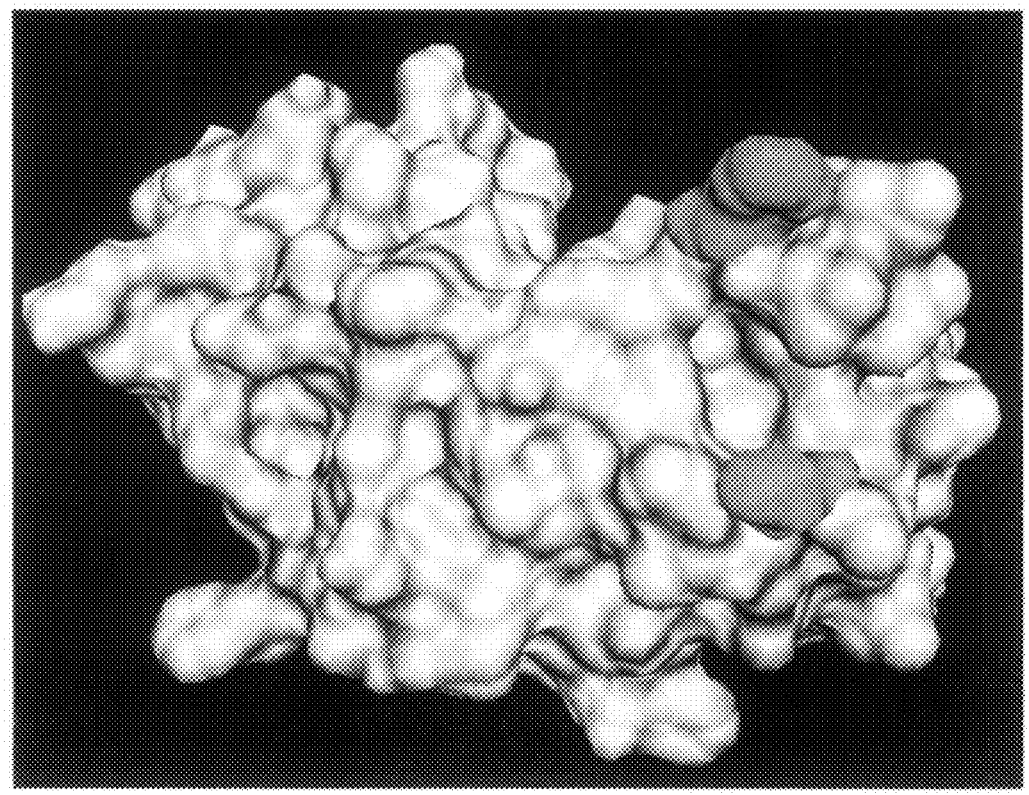

From a structural viewpoint, the tamarin and AGM mutated residues map in the head domain, with the exception of residues 196 and 197, which fall next to the C-terminus (see FIG. 3C), Leu197 being a subunit interface residue in human CD81. Residues 155, 163, 180, 186 and 188 are solvent exposed, such that their conservative substitution should not affect the domain conformation. On the other hand, the substitution of residues 154 and 169 is subject to polarity and residue size restrictions, since they occur at buried locations next to both disulfide bridges. In human CD81 Thr163 is located in the short $3_{10}$ segment preceding the C-helix, and Phe186 is the last residue in the D-helix. The two antiparallel helices build up a sort of narrow "canyon" sub-structure, whose floor is essentially defined by the Cys157--Cys175 disulfide connecting the CD loop to the domain core. Residues 163 and 186 are located at the canyon end opposing the CD loop (FIGS. 3A & 3C).

The mutant AGM and tamarin residues which affect E2 binding map to the C-, D-, E-helices, and the intervening segments i.e. residues mostly comprised within the two conserved disulfide bridges and including the 179-193 sequence stretch recognised as the minimal epitope for E2 binding [41]. Conformational integrity of this region is likely related to the oxidised state of the disulfide bridges, particularly the Cys157-Cys175 bridge; reduction of the disulfides impairs E2 and antibody recognition experiments [41, 43]. Sequence alignments show that the identified region displays highest residue variability within the CD81-LEL subfamily (FIG. 2), but also within other members of the tetraspanin family, which may bear specific residue deletions and insertions affecting the tertiary structure according to their molecular recognition requirements.

The conservation in the CD81 sequences of the hydrophobic residues Ile181, Ile182, Leu185, and Phe186 belonging to the D-helix (FIG. 2) is peculiar, since their solvent-exposed location (FIGS. 1C & 3A) should select against their conservation through species. Such an uncommon structural property, the extended intermolecular crystal contacts observed in this region, and the dramatic loss of E2 affinity related to Phe86 mutation, suggest that the D-helix region is the docking site for the viral glycoprotein E2.

It will be understood that the invention has been described by way of example only and modifications may be made whilst remaining within the scope and spirit of the invention.

REFERENCES (THE CONTENTS OF WHICH ARE HEREBY INCORPORATED IN FULL HEREIN)

1—Pileri et al. (1998) *Science* 282:938-941.
2—Further details: *Rational drug design: novel methodology and practical applications*, ACS Symposium Series vol. 719 (Parrill & Reddy eds., 1991).
3—Available from Tripos Inc (http://www.tripos.com).
4—Available from Oxford Molecular (http://www.oxmol.co.uk/).
5—Available from Molecular Simulations Inc (http://www.msi.com/).
6—Available from Hypercube Inc (http://www.hyper.com/).
7—Available from Pyramid Learning (http://www.chemsite.org/).
8—Blaney & Dixon (1993) *Perspectives in Drug Discovery and Design* 1:301
9—Kuntz et al. (1982) *J. Mol. Biol.* 161:269-288); available from UCSF.
10—Goodsell & Olson (1990) *Proteins: Structure, Function and Genetics* 8:195-202.
11—Meyer et al. (1995) *Persp. Drug Disc. Des.* 3:168-195
12—Nicklaus et al. (1995) *Bioorganic & Medicinal Chemistry* 3:411
13—Available from Chemical Computing Group Inc. (http://www.chemcomp.com/).
14—Jones et al. (1997) *J. Mol. Biol.* 267:727-748
15—Martin (1992) *J. Med. Chem.* 35:2145-54.
16—also *Computer-Assisted Lead Finding and Optimization* (eds. Testra & Folkers, 1997).
17—Davic & Lawrence (1992) *Proteins* 12:31-41.
18—Gehlhaar et al. (1995) *J. Med. Chem.* 38:466-72.
19—Caflish et al. (1993) *J. Med. Chem.* 36:2142-67
20—Eisen et al. (1994) *Proteins: Str. Funct. Genet.* 19:199-221.
21—Böhm (1992) *J. Comp. Aided Molec. Design* 6:61-78.
22—Moon & Howe (1991) *Proteins: Str. Funct. Genet.* 11:314-328.
23—Available from http://chem.leeds.ac.uk/ICAMS/SPROUT.html.
24—Rotstein et al. (1993) *J. Med. Client.* 36:1700.
25—Lauri & Bartlett (1994) *Comp. Aided Mol. Design* 8:51-66.
26—Lai (1996) *J. Chem. Inf. Comput. Sci.* 36:1187-1194.
27—File 1G8Q at the Protein Data Bank [http://www.rcsb.org/pdb/]
28—Kitadokoro et al. (2001) *Acta Crystallogr D Biol Crstallogr* 57:156-158.
29—Kitadokoro et al. (2001) *EMBO J.* 20:12-18.
30—Laskowski et al. (1993) *J. Appl. Crystallogr.* 26:283
31—Otwinowski & Minor (1996) *Methods Enzymol.* 276: 307.
32—CCP4, *Acta Crystallogr. D*50, 760 (1994).
33—Fortelle &. Bricogne (1997) *Methods Enzymol. B* 472
34—Abrahams & Leslie (1996) *Acta Crystallogr.* D52, 30.
35—Jones et al. (1991) *Acta Crystallogr.* A47, 110
36—Brunget et al. (1998) *Acta Crystallogr.* D 54, 905
37—Murshudov et al. (1997) *Acta Crystallogr.* D 53, 240
38—Maecker et al. (1997) *FASEB J.* 11:428-42.
39—Levy et al. (1998) *Annu Rev Immunol.* 16:89-109
40—Holm & Sander (1993) *J. Mol. Biol.* 233, 123
41—Higginbottom et al. (2000) *J. Virol.* 74:3642-9.
42—Meola et al. (2000) *J. Virol.* 74:5933.
43—Petracca et al. (2000) *J. Virol.* 74:4824-30.

---

PDB FILE LISTING –cd81lel.pdb

| | | | | | | |
|---|---|---|---|---|---|---|
| REMARK | Written by O version 7.0.0 | | | | | |
| REMARK | Mon Jun 26 07:13:19 2000 | | | | | |
| CRYST1 | 31.485 | 77.172 | 38.462 | 90.00 | 107.39 | 90.00 |
| ORIGX1 | 1.000000 | 0.000000 | 0.000000 | | 0.00000 | |
| ORIGX2 | 0.000000 | 1.000000 | 0.000000 | | 0.00000 | |

-continued

PDB FILE LISTING – cd81el.pdb

| | | | | | | | | | | | |
|---|---|---|---|---|---|---|---|---|---|---|---|
| ORIGX3 | | 0.000000 | | 0.000000 | 1.000000 | | 0.00000 | | | | |
| SCALE1 | | 0.031761 | | −0.000001 | 0.009946 | | 0.00000 | | | | |
| SCALE2 | | 0.000000 | | 0.012958 | 0.000000 | | 0.00000 | | | | |
| SCALE3 | | 0.000000 | | 0.000000 | 0.027245 | | 0.00000 | | | | |
| ATOM | 1 | CB | PHE | A | 113 | 13.054 | 44.460 | −4.086 | 1.00 | 35.22 | 6 |
| ATOM | 2 | CG | PHE | A | 113 | 13.550 | 44.904 | −5.447 | 1.00 | 34.10 | 6 |
| ATOM | 3 | CD1 | PHE | A | 113 | 13.436 | 46.217 | −5.867 | 1.00 | 33.03 | 6 |
| ATOM | 4 | CD2 | PHE | A | 113 | 14.097 | 43.957 | −6.288 | 1.00 | 31.53 | 6 |
| ATOM | 5 | CE1 | PHE | A | 113 | 13.846 | 46.604 | −7.112 | 1.00 | 41.68 | 6 |
| ATOM | 6 | CE2 | PHE | A | 113 | 14.536 | 44.353 | −7.552 | 1.00 | 33.43 | 6 |
| ATOM | 7 | CZ | PHE | A | 113 | 14.417 | 45.655 | −7.929 | 1.00 | 29.35 | 6 |
| ATOM | 8 | C | PHE | A | 113 | 13.055 | 44.591 | −1.648 | 1.00 | 34.73 | 6 |
| ATOM | 9 | O | PHE | A | 113 | 13.493 | 43.601 | −1.095 | 1.00 | 35.94 | 8 |
| ATOM | 10 | N | PHE | A | 113 | 15.194 | 44.738 | −2.818 | 1.00 | 38.93 | 7 |
| ATOM | 11 | CA | PHE | A | 113 | 13.749 | 45.121 | −2.929 | 1.00 | 35.51 | 6 |
| ATOM | 12 | N | VAL | A | 114 | 12.014 | 45.304 | −1.292 | 1.00 | 30.69 | 7 |
| ATOM | 13 | CA | VAL | A | 114 | 11.297 | 44.908 | −0.047 | 1.00 | 30.59 | 6 |
| ATOM | 14 | CB | VAL | A | 114 | 10.318 | 46.078 | 0.218 | 1.00 | 28.83 | 6 |
| ATOM | 15 | CG1 | VAL | A | 114 | 9.273 | 45.698 | 1.249 | 1.00 | 39.07 | 6 |
| ATOM | 16 | CG2 | VAL | A | 114 | 11.101 | 47.339 | 0.495 | 1.00 | 32.04 | 6 |
| ATOM | 17 | C | VAL | A | 114 | 10.519 | 43.644 | −0.291 | 1.00 | 33.72 | 6 |
| ATOM | 18 | O | VAL | A | 114 | 9.766 | 43.438 | −1.254 | 1.00 | 38.10 | 8 |
| ATOM | 19 | N | ASN | A | 115 | 10.631 | 42.726 | 0.661 | 1.00 | 26.02 | 7 |
| ATOM | 20 | CA | ASN | A | 115 | 9.999 | 41.431 | 0.616 | 1.00 | 26.31 | 6 |
| ATOM | 21 | CB | ASN | A | 115 | 11.119 | 40.392 | 0.761 | 1.00 | 32.36 | 6 |
| ATOM | 22 | CG | ASN | A | 115 | 10.695 | 38.985 | 0.416 | 1.00 | 36.81 | 6 |
| ATOM | 23 | OD1 | ASN | A | 115 | 9.539 | 38.606 | 0.608 | 1.00 | 37.44 | 8 |
| ATOM | 24 | ND2 | ASN | A | 115 | 11.665 | 38.213 | −0.109 | 1.00 | 41.24 | 7 |
| ATOM | 25 | C | ASN | A | 115 | 9.050 | 41.307 | 1.840 | 1.00 | 29.28 | 6 |
| ATOM | 26 | O | ASN | A | 115 | 9.588 | 40.946 | 2.886 | 1.00 | 29.32 | 8 |
| ATOM | 27 | N | LYS | A | 116 | 7.818 | 41.715 | 1.661 | 1.00 | 28.31 | 7 |
| ATOM | 28 | CA | LYS | A | 116 | 6.877 | 41.671 | 2.790 | 1.00 | 30.52 | 6 |
| ATOM | 29 | CB | LYS | A | 116 | 5.534 | 42.201 | 2.323 | 1.00 | 32.42 | 6 |
| ATOM | 30 | CG | LYS | A | 116 | 4.438 | 42.302 | 3.360 | 1.00 | 40.71 | 6 |
| ATOM | 31 | CD | LYS | A | 116 | 3.494 | 41.125 | 3.184 | 1.00 | 54.74 | 6 |
| ATOM | 32 | CE | LYS | A | 116 | 2.097 | 41.504 | 3.656 | 1.00 | 50.77 | 6 |
| ATOM | 33 | NZ | LYS | A | 116 | 1.233 | 40.305 | 3.663 | 1.00 | 45.99 | 7 |
| ATOM | 34 | C | LYS | A | 116 | 6.740 | 40.325 | 3.467 | 1.00 | 29.54 | 6 |
| ATOM | 35 | O | LYS | A | 116 | 6.720 | 40.232 | 4.696 | 1.00 | 27.76 | 8 |
| ATOM | 36 | N | ASP | A | 117 | 6.611 | 39.248 | 2.695 | 1.00 | 29.77 | 7 |
| ATOM | 37 | CA | ASP | A | 117 | 6.551 | 37.911 | 3.304 | 1.00 | 30.69 | 6 |
| ATOM | 38 | CB | ASP | A | 117 | 6.396 | 36.802 | 2.261 | 1.00 | 35.31 | 6 |
| ATOM | 39 | CG | ASP | A | 117 | 5.055 | 36.833 | 1.558 | 1.00 | 41.21 | 6 |
| ATOM | 40 | OD1 | ASP | A | 117 | 4.955 | 36.192 | 0.472 | 1.00 | 44.39 | 8 |
| ATOM | 41 | OD2 | ASP | A | 117 | 4.140 | 37.496 | 2.092 | 1.00 | 44.63 | 8 |
| ATOM | 42 | C | ASP | A | 117 | 7.800 | 37.628 | 4.109 | 1.00 | 31.27 | 6 |
| ATOM | 43 | O | ASP | A | 117 | 7.612 | 37.076 | 5.208 | 1.00 | 29.68 | 8 |
| ATOM | 44 | N | GLN | A | 118 | 9.006 | 37.962 | 3.675 | 1.00 | 27.32 | 7 |
| ATOM | 45 | CA | GLN | A | 118 | 10.192 | 37.645 | 4.471 | 1.00 | 23.79 | 6 |
| ATOM | 46 | CB | GLN | A | 118 | 11.500 | 37.816 | 3.709 | 1.00 | 33.42 | 6 |
| ATOM | 47 | CG | GLN | A | 118 | 12.392 | 36.592 | 3.917 | 1.00 | 50.37 | 6 |
| ATOM | 48 | CD | GLN | A | 118 | 11.870 | 35.402 | 3.136 | 1.00 | 55.11 | 6 |
| ATOM | 49 | OE1 | GLN | A | 118 | 11.385 | 34.436 | 3.730 | 1.00 | 61.81 | 8 |
| ATOM | 50 | NE2 | GLN | A | 118 | 11.933 | 35.435 | 1.806 | 1.00 | 55.23 | 7 |
| ATOM | 51 | C | GLN | A | 118 | 10.218 | 38.513 | 5.755 | 1.00 | 25.07 | 6 |
| ATOM | 52 | O | GLN | A | 118 | 10.575 | 38.027 | 6.842 | 1.00 | 28.38 | 8 |
| ATOM | 53 | N | ILE | A | 119 | 9.863 | 39.760 | 5.566 | 1.00 | 25.14 | 7 |
| ATOM | 54 | CA | ILE | A | 119 | 9.880 | 40.701 | 6.719 | 1.00 | 23.26 | 6 |
| ATOM | 55 | CB | ILE | A | 119 | 9.498 | 42.128 | 6.266 | 1.00 | 27.36 | 6 |
| ATOM | 56 | CG2 | ILE | A | 119 | 9.266 | 43.023 | 7.510 | 1.00 | 23.47 | 6 |
| ATOM | 57 | CG1 | ILE | A | 119 | 10.560 | 42.718 | 5.345 | 1.00 | 30.01 | 6 |
| ATOM | 58 | CD1 | ILE | A | 119 | 10.193 | 44.009 | 4.618 | 1.00 | 30.66 | 6 |
| ATOM | 59 | C | ILE | A | 119 | 8.938 | 40.184 | 7.788 | 1.00 | 23.31 | 6 |
| ATOM | 60 | O | ILE | A | 119 | 9.311 | 40.183 | 8.996 | 1.00 | 25.16 | 8 |
| ATOM | 61 | N | ALA | A | 120 | 7.712 | 39.788 | 7.412 | 1.00 | 24.17 | 7 |
| ATOM | 62 | CA | ALA | A | 120 | 6.781 | 39.316 | 8.463 | 1.00 | 25.04 | 6 |
| ATOM | 63 | CB | ALA | A | 120 | 5.384 | 38.976 | 7.916 | 1.00 | 29.48 | 6 |
| ATOM | 64 | C | ALA | A | 120 | 7.304 | 38.051 | 9.147 | 1.00 | 24.84 | 6 |
| ATOM | 65 | O | ALA | A | 120 | 7.234 | 37.964 | 10.377 | 1.00 | 25.63 | 8 |
| ATOM | 66 | N | LYS | A | 121 | 7.886 | 37.145 | 8.333 | 1.00 | 25.80 | 7 |
| ATOM | 67 | CA | LYS | A | 121 | 8.459 | 35.934 | 8.924 | 1.00 | 27.45 | 6 |
| ATOM | 68 | CB | LYS | A | 121 | 8.937 | 35.072 | 7.739 | 1.00 | 31.96 | 6 |
| ATOM | 69 | CG | LYS | A | 121 | 10.222 | 34.305 | 7.934 | 1.00 | 45.25 | 6 |
| ATOM | 70 | CD | LYS | A | 121 | 11.443 | 35.174 | 7.733 | 1.00 | 55.59 | 6 |
| ATOM | 71 | CE | LYS | A | 121 | 12.488 | 34.542 | 6.833 | 1.00 | 54.95 | 6 |
| ATOM | 72 | NZ | LYS | A | 121 | 13.434 | 35.534 | 6.259 | 1.00 | 49.41 | 7 |
| ATOM | 73 | C | LYS | A | 121 | 9.581 | 36.310 | 9.886 | 1.00 | 24.12 | 6 |

-continued

PDB FILE LISTING –cd81el.pdb

| ATOM | 74 | O | LYS | A | 121 | 9.630 | 35.792 | 11.038 | 1.00 | 26.90 | 8 |
|---|---|---|---|---|---|---|---|---|---|---|---|
| ATOM | 75 | N | ASP | A | 122 | 10.378 | 37.296 | 9.562 | 1.00 | 23.49 | 7 |
| ATOM | 76 | CA | ASP | A | 122 | 11.489 | 37.734 | 10.391 | 1.00 | 24.47 | 6 |
| ATOM | 77 | CB | ASP | A | 122 | 12.549 | 38.580 | 9.737 | 1.00 | 22.87 | 6 |
| ATOM | 78 | CG | ASP | A | 122 | 13.362 | 37.819 | 8.674 | 1.00 | 26.68 | 6 |
| ATOM | 79 | OD1 | ASP | A | 122 | 13.273 | 36.574 | 8.574 | 1.00 | 32.55 | 8 |
| ATOM | 80 | OD2 | ASP | A | 122 | 14.103 | 38.528 | 7.955 | 1.00 | 31.33 | 8 |
| ATOM | 81 | C | ASP | A | 122 | 10.982 | 38.456 | 11.665 | 1.00 | 24.38 | 6 |
| ATOM | 82 | O | ASP | A | 122 | 11.555 | 38.251 | 12.733 | 1.00 | 22.88 | 8 |
| ATOM | 83 | N | VAL | A | 123 | 9.945 | 39.256 | 11.552 | 1.00 | 24.91 | 7 |
| ATOM | 84 | CA | VAL | A | 123 | 9.363 | 39.886 | 12.747 | 1.00 | 22.20 | 6 |
| ATOM | 85 | CB | VAL | A | 123 | 8.288 | 40.939 | 12.399 | 1.00 | 18.76 | 6 |
| ATOM | 86 | CG1 | VAL | A | 123 | 7.800 | 41.562 | 13.705 | 1.00 | 20.06 | 6 |
| ATOM | 87 | CG2 | VAL | A | 123 | 9.037 | 42.026 | 11.568 | 1.00 | 23.40 | 6 |
| ATOM | 88 | C | VAL | A | 123 | 8.825 | 38.829 | 13.692 | 1.00 | 20.54 | 6 |
| ATOM | 89 | O | VAL | A | 123 | 9.008 | 38.889 | 14.911 | 1.00 | 22.54 | 8 |
| ATOM | 90 | N | LYS | A | 124 | 8.098 | 37.844 | 13.114 | 1.00 | 21.95 | 7 |
| ATOM | 91 | CA | LYS | A | 124 | 7.566 | 36.768 | 14.018 | 1.00 | 24.00 | 6 |
| ATOM | 92 | CB | LYS | A | 124 | 6.797 | 35.783 | 13.134 | 1.00 | 26.02 | 6 |
| ATOM | 93 | CG | LYS | A | 124 | 5.505 | 36.413 | 12.619 | 1.00 | 25.26 | 6 |
| ATOM | 94 | CD | LYS | A | 124 | 4.836 | 35.414 | 11.667 | 1.00 | 29.55 | 6 |
| ATOM | 95 | CE | LYS | A | 124 | 3.735 | 36.131 | 10.886 | 1.00 | 32.92 | 6 |
| ATOM | 96 | NZ | LYS | A | 124 | 3.115 | 35.139 | 9.941 | 1.00 | 31.45 | 7 |
| ATOM | 97 | C | LYS | A | 124 | 8.722 | 36.046 | 14.715 | 1.00 | 25.01 | 6 |
| ATOM | 98 | O | LYS | A | 124 | 8.678 | 35.783 | 15.931 | 1.00 | 24.77 | 8 |
| ATOM | 99 | N | GLN | A | 125 | 9.817 | 35.779 | 14.045 | 1.00 | 22.22 | 7 |
| ATOM | 100 | CA | GLN | A | 125 | 10.963 | 35.105 | 14.630 | 1.00 | 25.09 | 6 |
| ATOM | 101 | CB | GLN | A | 125 | 11.933 | 34.615 | 13.553 | 1.00 | 28.89 | 6 |
| ATOM | 102 | CG | GLN | A | 125 | 13.031 | 33.781 | 14.176 | 1.00 | 28.74 | 6 |
| ATOM | 103 | CD | GLN | A | 125 | 12.610 | 32.683 | 15.121 | 1.00 | 51.08 | 6 |
| ATOM | 104 | OE1 | GLN | A | 125 | 11.475 | 32.201 | 15.227 | 1.00 | 48.79 | 8 |
| ATOM | 105 | NE2 | GLN | A | 125 | 13.577 | 32.195 | 15.910 | 1.00 | 55.92 | 7 |
| ATOM | 106 | C | GLN | A | 125 | 11.677 | 35.939 | 15.667 | 1.00 | 22.42 | 6 |
| ATOM | 107 | O | GLN | A | 125 | 12.007 | 35.481 | 16.740 | 1.00 | 26.28 | 8 |
| ATOM | 108 | N | PHE | A | 126 | 11.872 | 37.249 | 15.396 | 1.00 | 21.19 | 7 |
| ATOM | 109 | CA | PHE | A | 126 | 12.395 | 38.149 | 16.407 | 1.00 | 23.84 | 6 |
| ATOM | 110 | CB | PHE | A | 126 | 12.358 | 39.571 | 15.868 | 1.00 | 20.40 | 6 |
| ATOM | 111 | CG | PHE | A | 126 | 12.978 | 40.587 | 16.762 | 1.00 | 22.25 | 6 |
| ATOM | 112 | CD1 | PHE | A | 126 | 14.372 | 40.659 | 16.802 | 1.00 | 24.92 | 6 |
| ATOM | 113 | CD2 | PHE | A | 126 | 12.201 | 41.422 | 17.567 | 1.00 | 24.93 | 6 |
| ATOM | 114 | CE1 | PHE | A | 126 | 14.990 | 41.588 | 17.628 | 1.00 | 28.09 | 6 |
| ATOM | 115 | CE2 | PHE | A | 126 | 12.844 | 42.353 | 18.368 | 1.00 | 21.69 | 6 |
| ATOM | 116 | CZ | PHE | A | 126 | 14.202 | 42.409 | 18.427 | 1.00 | 27.78 | 6 |
| ATOM | 117 | C | PHE | A | 126 | 11.592 | 38.131 | 17.688 | 1.00 | 21.94 | 6 |
| ATOM | 118 | O | PHE | A | 126 | 12.060 | 38.065 | 18.810 | 1.00 | 22.84 | 8 |
| ATOM | 119 | N | TYR | A | 127 | 10.246 | 38.180 | 17.534 | 1.00 | 19.86 | 7 |
| ATOM | 120 | CA | TYR | A | 127 | 9.349 | 38.135 | 18.698 | 1.00 | 20.03 | 6 |
| ATOM | 121 | CB | TYR | A | 127 | 7.865 | 38.224 | 18.184 | 1.00 | 23.84 | 6 |
| ATOM | 122 | CG | TYR | A | 127 | 6.918 | 37.987 | 19.351 | 1.00 | 21.94 | 6 |
| ATOM | 123 | CD1 | TYR | A | 127 | 6.577 | 38.925 | 20.305 | 1.00 | 21.20 | 6 |
| ATOM | 124 | CE1 | TYR | A | 127 | 5.735 | 38.634 | 21.368 | 1.00 | 17.80 | 6 |
| ATOM | 125 | CD2 | TYR | A | 127 | 6.394 | 36.687 | 19.461 | 1.00 | 21.35 | 6 |
| ATOM | 126 | CE2 | TYR | A | 127 | 5.542 | 36.351 | 20.521 | 1.00 | 23.38 | 6 |
| ATOM | 127 | CZ | TYR | A | 127 | 5.221 | 37.318 | 21.444 | 1.00 | 22.17 | 6 |
| ATOM | 128 | OH | TYR | A | 127 | 4.376 | 36.942 | 22.471 | 1.00 | 22.46 | 8 |
| ATOM | 129 | C | TYR | A | 127 | 9.552 | 36.818 | 19.437 | 1.00 | 18.72 | 6 |
| ATOM | 130 | O | TYR | A | 127 | 9.655 | 36.851 | 20.694 | 1.00 | 21.79 | 8 |
| ATOM | 131 | N | ASP | A | 128 | 9.606 | 35.711 | 18.693 | 1.00 | 23.27 | 7 |
| ATOM | 132 | CA | ASP | A | 128 | 9.726 | 34.407 | 19.418 | 1.00 | 22.55 | 6 |
| ATOM | 133 | CB | ASP | A | 128 | 9.674 | 33.283 | 18.359 | 1.00 | 25.98 | 6 |
| ATOM | 134 | CG | ASP | A | 128 | 8.249 | 33.014 | 17.910 | 1.00 | 29.92 | 6 |
| ATOM | 135 | OD1 | ASP | A | 128 | 8.110 | 32.180 | 16.988 | 1.00 | 32.49 | 8 |
| ATOM | 136 | OD2 | ASP | A | 128 | 7.294 | 33.586 | 18.464 | 1.00 | 27.69 | 8 |
| ATOM | 137 | C | ASP | A | 128 | 11.093 | 34.278 | 20.077 | 1.00 | 24.19 | 6 |
| ATOM | 138 | O | ASP | A | 128 | 11.158 | 33.755 | 21.208 | 1.00 | 22.87 | 8 |
| ATOM | 139 | N | GLN | A | 129 | 12.140 | 34.817 | 19.447 | 1.00 | 22.82 | 7 |
| ATOM | 140 | CA | GLN | A | 129 | 13.441 | 34.812 | 20.158 | 1.00 | 22.77 | 6 |
| ATOM | 141 | CB | GLN | A | 129 | 14.505 | 35.588 | 19.324 | 1.00 | 25.03 | 6 |
| ATOM | 142 | CG | GLN | A | 129 | 14.771 | 34.862 | 18.042 | 1.00 | 25.57 | 6 |
| ATOM | 143 | CD | GLN | A | 129 | 15.665 | 35.668 | 17.072 | 1.00 | 26.40 | 6 |
| ATOM | 144 | OE1 | GLN | A | 129 | 15.978 | 35.087 | 16.038 | 1.00 | 30.69 | 8 |
| ATOM | 145 | NE2 | GLN | A | 129 | 15.991 | 36.913 | 17.459 | 1.00 | 30.93 | 7 |
| ATOM | 146 | C | GLN | A | 129 | 13.299 | 35.632 | 21.434 | 1.00 | 22.40 | 6 |
| ATOM | 147 | O | GLN | A | 129 | 13.819 | 35.202 | 22.487 | 1.00 | 25.02 | 8 |
| ATOM | 148 | N | ALA | A | 130 | 12.695 | 36.829 | 22.395 | 1.00 | 20.16 | 7 |
| ATOM | 149 | CA | ALA | A | 130 | 12.602 | 37.564 | 22.647 | 1.00 | 19.19 | 6 |
| ATOM | 150 | CB | ALA | A | 130 | 12.049 | 39.003 | 22.397 | 1.00 | 21.18 | 6 |

-continued

PDB FILE LISTING –cd81el.pdb

| ATOM | 151 | C | ALA | A | 130 | 11.791 | 36.880 | 23.687 | 1.00 | 22.54 | 6 |
| ATOM | 152 | O | ALA | A | 130 | 12.047 | 36.945 | 24.912 | 1.00 | 22.88 | 8 |
| ATOM | 153 | N | LEU | A | 131 | 10.655 | 36.253 | 23.276 | 1.00 | 18.79 | 7 |
| ATOM | 154 | CA | LEU | A | 131 | 9.742 | 35.645 | 24.266 | 1.00 | 21.57 | 6 |
| ATOM | 155 | CB | LEU | A | 131 | 8.492 | 35.127 | 23.523 | 1.00 | 21.87 | 6 |
| ATOM | 156 | CG | LEU | A | 131 | 7.340 | 34.780 | 24.516 | 1.00 | 26.58 | 6 |
| ATOM | 157 | CD1 | LEU | A | 131 | 6.825 | 36.097 | 25.128 | 1.00 | 24.19 | 6 |
| ATOM | 158 | CD2 | LEU | A | 131 | 6.209 | 34.116 | 23.747 | 1.00 | 23.85 | 6 |
| ATOM | 159 | C | LEU | A | 131 | 10.454 | 34.451 | 24.948 | 1.00 | 21.60 | 6 |
| ATOM | 160 | O | LEU | A | 131 | 10.320 | 34.274 | 26.150 | 1.00 | 22.16 | 8 |
| ATOM | 161 | N | GLN | A | 132 | 11.181 | 33.692 | 24.137 | 1.00 | 22.17 | 7 |
| ATOM | 162 | CA | GLN | A | 132 | 11.884 | 32.531 | 24.707 | 1.00 | 23.12 | 6 |
| ATOM | 163 | CB | GLN | A | 132 | 12.508 | 31.669 | 23.581 | 1.00 | 22.76 | 6 |
| ATOM | 164 | CG | GLN | A | 132 | 11.381 | 30.963 | 22.796 | 1.00 | 24.05 | 6 |
| ATOM | 165 | CD | GLN | A | 132 | 11.961 | 30.193 | 21.606 | 1.00 | 25.65 | 6 |
| ATOM | 166 | OE1 | GLN | A | 132 | 11.936 | 28.946 | 21.582 | 1.00 | 28.29 | 8 |
| ATOM | 167 | NE2 | GLN | A | 132 | 12.428 | 30.852 | 20.541 | 1.00 | 25.24 | 7 |
| ATOM | 168 | C | GLN | A | 132 | 12.922 | 32.987 | 25.692 | 1.00 | 22.26 | 6 |
| ATOM | 169 | O | GLN | A | 132 | 13.006 | 32.389 | 26.770 | 1.00 | 23.25 | 8 |
| ATOM | 170 | N | GLN | A | 133 | 13.693 | 34.050 | 25.412 | 1.00 | 21.14 | 7 |
| ATOM | 171 | CA | GLN | A | 133 | 14.711 | 34.509 | 26.348 | 1.00 | 21.05 | 6 |
| ATOM | 172 | CB | GLN | A | 133 | 15.533 | 35.610 | 25.619 | 1.00 | 22.48 | 6 |
| ATOM | 173 | CG | GLN | A | 133 | 16.687 | 35.994 | 26.548 | 1.00 | 25.57 | 6 |
| ATOM | 174 | CD | GLN | A | 133 | 17.650 | 36.993 | 25.926 | 1.00 | 23.61 | 6 |
| ATOM | 175 | OE1 | GLN | A | 133 | 17.463 | 37.432 | 24.806 | 1.00 | 28.80 | 8 |
| ATOM | 176 | NE2 | GLN | A | 133 | 18.726 | 37.251 | 26.669 | 1.00 | 29.55 | 7 |
| ATOM | 177 | C | GLN | A | 133 | 14.070 | 35.146 | 27.572 | 1.00 | 22.02 | 6 |
| ATOM | 178 | O | GLN | A | 133 | 14.481 | 34.985 | 28.734 | 1.00 | 24.53 | 8 |
| ATOM | 179 | N | ALA | A | 134 | 12.946 | 35.879 | 27.368 | 1.00 | 22.25 | 7 |
| ATOM | 180 | CA | ALA | A | 134 | 12.270 | 36.531 | 28.489 | 1.00 | 24.32 | 6 |
| ATOM | 181 | CB | ALA | A | 134 | 11.058 | 37.332 | 27.987 | 1.00 | 24.55 | 6 |
| ATOM | 182 | C | ALA | A | 134 | 11.798 | 35.628 | 29.623 | 1.00 | 23.77 | 6 |
| ATOM | 183 | O | ALA | A | 134 | 11.708 | 35.947 | 30.819 | 1.00 | 27.92 | 8 |
| ATOM | 184 | N | VAL | A | 135 | 11.447 | 34.399 | 29.250 | 1.00 | 22.81 | 7 |
| ATOM | 185 | CA | VAL | A | 135 | 10.918 | 33.425 | 30.203 | 1.00 | 22.24 | 6 |
| ATOM | 186 | CB | VAL | A | 135 | 9.948 | 32.446 | 29.546 | 1.00 | 31.11 | 6 |
| ATOM | 187 | CG1 | VAL | A | 135 | 8.682 | 33.122 | 29.084 | 1.00 | 29.66 | 6 |
| ATOM | 188 | CG2 | VAL | A | 135 | 10.546 | 31.496 | 28.557 | 1.00 | 45.64 | 6 |
| ATOM | 189 | C | VAL | A | 135 | 12.043 | 32.676 | 30.843 | 1.00 | 25.73 | 6 |
| ATOM | 190 | O | VAL | A | 135 | 11.880 | 32.216 | 31.986 | 1.00 | 31.63 | 8 |
| ATOM | 191 | N | VAL | A | 136 | 13.147 | 32.472 | 30.135 | 1.00 | 30.36 | 7 |
| ATOM | 192 | CA | VAL | A | 136 | 14.211 | 31.649 | 30.768 | 1.00 | 29.23 | 6 |
| ATOM | 193 | CB | VAL | A | 136 | 14.704 | 30.717 | 29.663 | 1.00 | 30.54 | 6 |
| ATOM | 194 | CG1 | VAL | A | 136 | 15.653 | 31.427 | 28.727 | 1.00 | 28.12 | 6 |
| ATOM | 195 | CG2 | VAL | A | 136 | 15.237 | 29.401 | 30.184 | 1.00 | 33.07 | 6 |
| ATOM | 196 | C | VAL | A | 136 | 15.274 | 32.433 | 31.445 | 1.00 | 32.01 | 6 |
| ATOM | 197 | O | VAL | A | 136 | 16.080 | 31.921 | 32.242 | 1.00 | 35.58 | 8 |
| ATOM | 198 | N | ASP | A | 137 | 15.520 | 33.683 | 31.050 | 1.00 | 29.34 | 7 |
| ATOM | 199 | CA | ASP | A | 137 | 16.647 | 34.496 | 31.487 | 1.00 | 30.00 | 6 |
| ATOM | 200 | CB | ASP | A | 137 | 17.273 | 35.171 | 30.263 | 1.00 | 31.01 | 6 |
| ATOM | 201 | CG | ASP | A | 137 | 18.536 | 35.952 | 30.547 | 1.00 | 38.12 | 6 |
| ATOM | 202 | OD1 | ASP | A | 137 | 19.181 | 36.426 | 29.580 | 1.00 | 33.65 | 8 |
| ATOM | 203 | OD2 | ASP | A | 137 | 18.933 | 36.171 | 31.710 | 1.00 | 34.77 | 8 |
| ATOM | 204 | C | ASP | A | 137 | 16.127 | 35.551 | 32.450 | 1.00 | 35.73 | 6 |
| ATOM | 205 | O | ASP | A | 137 | 15.411 | 36.471 | 32.043 | 1.00 | 35.33 | 8 |
| ATOM | 206 | N | ASP | A | 138 | 16.486 | 35.444 | 33.718 | 1.00 | 41.35 | 7 |
| ATOM | 207 | CA | ASP | A | 138 | 16.026 | 36.345 | 34.735 | 1.00 | 44.53 | 6 |
| ATOM | 208 | CB | ASP | A | 138 | 16.349 | 35.881 | 36.159 | 1.00 | 55.88 | 6 |
| ATOM | 209 | CG | ASP | A | 138 | 14.551 | 35.422 | 36.525 | 0.00 | 27.18 | 6 |
| ATOM | 210 | OD1 | ASP | A | 138 | 14.174 | 34.275 | 36.165 | 0.00 | 27.18 | 8 |
| ATOM | 211 | OD2 | ASP | A | 138 | 13.773 | 36.235 | 37.082 | 0.00 | 27.18 | 8 |
| ATOM | 212 | C | ASP | A | 138 | 16.457 | 37.783 | 34.550 | 1.00 | 45.63 | 6 |
| ATOM | 213 | O | ASP | A | 138 | 15.642 | 38.619 | 34.905 | 1.00 | 46.37 | 8 |
| ATOM | 214 | N | ASP | A | 139 | 17.659 | 38.047 | 34.046 | 1.00 | 47.04 | 7 |
| ATOM | 215 | CA | ASP | A | 139 | 18.045 | 39.434 | 33.860 | 1.00 | 47.12 | 6 |
| ATOM | 216 | CB | ASP | A | 139 | 19.315 | 39.889 | 34.534 | 1.00 | 59.30 | 6 |
| ATOM | 217 | CG | ASP | A | 139 | 20.138 | 38.776 | 35.141 | 1.00 | 60.21 | 6 |
| ATOM | 218 | OD1 | ASP | A | 139 | 20.667 | 37.956 | 34.371 | 1.00 | 66.48 | 8 |
| ATOM | 219 | OD2 | ASP | A | 139 | 20.245 | 38.739 | 36.381 | 1.00 | 60.42 | 8 |
| ATOM | 220 | C | ASP | A | 139 | 17.980 | 39.852 | 32.397 | 1.00 | 44.11 | 6 |
| ATOM | 221 | O | ASP | A | 139 | 18.684 | 40.814 | 32.054 | 1.00 | 45.91 | 8 |
| ATOM | 222 | N | ALA | A | 140 | 17.165 | 39.159 | 31.588 | 1.00 | 36.40 | 7 |
| ATOM | 223 | CA | ALA | A | 140 | 17.097 | 39.640 | 30.176 | 1.00 | 34.34 | 6 |
| ATOM | 224 | CB | ALA | A | 140 | 16.549 | 38.514 | 29.305 | 1.00 | 29.85 | 6 |
| ATOM | 225 | C | ALA | A | 140 | 16.124 | 40.801 | 30.144 | 1.00 | 29.56 | 6 |
| ATOM | 226 | O | ALA | A | 140 | 14.956 | 40.665 | 29.725 | 1.00 | 28.22 | 8 |
| ATOM | 227 | N | ASN | A | 141 | 16.528 | 41.977 | 30.625 | 1.00 | 29.81 | 7 |

-continued

PDB FILE LISTING –cd81el.pdb

| ATOM | 228 | CA | ASN | A | 141 | 15.623 | 43.101 | 30.725 | 1.00 | 30.52 | 6 |
| ATOM | 229 | CB | ASN | A | 141 | 16.336 | 44.264 | 31.435 | 1.00 | 37.01 | 6 |
| ATOM | 230 | CG | ASN | A | 141 | 16.696 | 43.864 | 32.857 | 1.00 | 54.30 | 6 |
| ATOM | 231 | OD1 | ASN | A | 141 | 15.795 | 43.768 | 33.690 | 1.00 | 48.05 | 8 |
| ATOM | 232 | ND2 | ASN | A | 141 | 17.991 | 43.645 | 33.062 | 1.00 | 56.03 | 7 |
| ATOM | 233 | C | ASN | A | 141 | 15.225 | 43.622 | 29.319 | 1.00 | 25.07 | 6 |
| ATOM | 234 | O | ASN | A | 141 | 14.036 | 43.975 | 29.220 | 1.00 | 30.82 | 8 |
| ATOM | 235 | N | ASN | A | 142 | 16.189 | 43.580 | 28.407 | 1.00 | 32.80 | 7 |
| ATOM | 236 | CA | ASN | A | 142 | 15.802 | 44.039 | 27.068 | 1.00 | 27.52 | 6 |
| ATOM | 237 | CB | ASN | A | 142 | 16.955 | 44.259 | 26.125 | 1.00 | 32.75 | 6 |
| ATOM | 238 | CG | ASN | A | 142 | 17.649 | 45.601 | 26.305 | 1.00 | 52.93 | 6 |
| ATOM | 239 | OD1 | ASN | A | 142 | 18.857 | 45.697 | 26.058 | 1.00 | 59.14 | 8 |
| ATOM | 240 | ND2 | ASN | A | 142 | 16.922 | 46.626 | 26.735 | 1.00 | 57.80 | 7 |
| ATOM | 241 | C | ASN | A | 142 | 14.791 | 43.064 | 26.464 | 1.00 | 25.36 | 6 |
| ATOM | 242 | O | ASN | A | 142 | 13.788 | 43.551 | 25.878 | 1.00 | 26.29 | 8 |
| ATOM | 243 | N | ALA | A | 143 | 15.035 | 41.759 | 26.593 | 1.00 | 23.53 | 7 |
| ATOM | 244 | CA | ALA | A | 143 | 14.041 | 40.835 | 26.012 | 1.00 | 25.47 | 6 |
| ATOM | 245 | CB | ALA | A | 143 | 14.443 | 39.375 | 26.206 | 1.00 | 22.30 | 6 |
| ATOM | 246 | C | ALA | A | 143 | 12.661 | 41.003 | 26.568 | 1.00 | 24.29 | 6 |
| ATOM | 247 | O | ALA | A | 143 | 11.612 | 40.989 | 25.897 | 1.00 | 22.58 | 8 |
| ATOM | 248 | N | LYS | A | 144 | 12.519 | 41.185 | 27.922 | 1.00 | 21.87 | 7 |
| ATOM | 249 | CA | LYS | A | 144 | 11.258 | 41.408 | 28.541 | 1.00 | 20.70 | 6 |
| ATOM | 250 | CB | LYS | A | 144 | 11.375 | 41.391 | 30.083 | 1.00 | 28.64 | 6 |
| ATOM | 251 | CG | LYS | A | 144 | 11.856 | 40.022 | 30.597 | 1.00 | 26.79 | 6 |
| ATOM | 252 | CD | LYS | A | 144 | 12.210 | 40.226 | 32.089 | 1.00 | 31.38 | 6 |
| ATOM | 253 | CE | LYS | A | 144 | 13.007 | 39.023 | 32.585 | 1.00 | 45.61 | 6 |
| ATOM | 254 | NZ | LYS | A | 144 | 12.035 | 37.945 | 32.966 | 1.00 | 43.86 | 7 |
| ATOM | 255 | C | LYS | A | 144 | 10.663 | 42.717 | 28.045 | 1.00 | 19.65 | 6 |
| ATOM | 256 | O | LYS | A | 144 | 9.472 | 42.704 | 27.782 | 1.00 | 24.45 | 8 |
| ATOM | 257 | N | ALA | A | 145 | 11.500 | 43.758 | 27.888 | 1.00 | 22.72 | 7 |
| ATOM | 258 | CA | ALA | A | 145 | 10.889 | 45.019 | 27.383 | 1.00 | 24.10 | 6 |
| ATOM | 259 | CB | ALA | A | 145 | 11.949 | 46.097 | 27.451 | 1.00 | 23.70 | 6 |
| ATOM | 260 | C | ALA | A | 145 | 10.430 | 44.868 | 25.914 | 1.00 | 21.09 | 6 |
| ATOM | 261 | O | ALA | A | 145 | 9.302 | 45.355 | 25.644 | 1.00 | 21.56 | 8 |
| ATOM | 262 | N | VAL | A | 146 | 12.171 | 44.078 | 25.189 | 1.00 | 22.29 | 7 |
| ATOM | 263 | CA | VAL | A | 146 | 10.683 | 43.855 | 23.784 | 1.00 | 20.84 | 6 |
| ATOM | 264 | CB | VAL | A | 146 | 11.731 | 43.079 | 22.976 | 1.00 | 22.15 | 6 |
| ATOM | 265 | CG1 | VAL | A | 146 | 11.112 | 42.478 | 21.711 | 1.00 | 23.27 | 6 |
| ATOM | 266 | CG2 | VAL | A | 146 | 12.898 | 44.014 | 22.734 | 1.00 | 22.16 | 6 |
| ATOM | 267 | C | VAL | A | 146 | 9.361 | 43.149 | 23.742 | 1.00 | 19.58 | 6 |
| ATOM | 268 | O | VAL | A | 146 | 8.394 | 43.563 | 23.088 | 1.00 | 21.79 | 8 |
| ATOM | 269 | N | VAL | A | 147 | 9.239 | 42.066 | 24.552 | 1.00 | 19.17 | 7 |
| ATOM | 270 | CA | VAL | A | 147 | 7.968 | 41.312 | 24.548 | 1.00 | 19.64 | 6 |
| ATOM | 271 | CB | VAL | A | 147 | 8.263 | 40.138 | 25.586 | 1.00 | 23.25 | 6 |
| ATOM | 272 | CG1 | VAL | A | 147 | 7.102 | 39.633 | 26.344 | 1.00 | 36.08 | 6 |
| ATOM | 273 | CG2 | VAL | A | 147 | 8.943 | 39.101 | 24.664 | 1.00 | 32.42 | 6 |
| ATOM | 274 | C | VAL | A | 147 | 6.844 | 42.194 | 25.068 | 1.00 | 20.95 | 6 |
| ATOM | 275 | O | VAL | A | 147 | 5.742 | 42.204 | 24.529 | 1.00 | 21.71 | 8 |
| ATOM | 276 | N | LYS | A | 148 | 7.072 | 42.924 | 26.178 | 1.00 | 19.59 | 7 |
| ATOM | 277 | CA | LYS | A | 148 | 5.979 | 43.783 | 26.688 | 1.00 | 21.04 | 6 |
| ATOM | 278 | CB | LYS | A | 148 | 6.499 | 44.431 | 27.981 | 1.00 | 26.20 | 6 |
| ATOM | 279 | CG | LYS | A | 148 | 6.574 | 43.388 | 29.093 | 1.00 | 27.82 | 6 |
| ATOM | 280 | CD | LYS | A | 148 | 6.786 | 44.057 | 30.419 | 1.00 | 30.78 | 6 |
| ATOM | 281 | CE | LYS | A | 148 | 8.007 | 44.919 | 30.523 | 1.00 | 46.34 | 6 |
| ATOM | 282 | NZ | LYS | A | 148 | 8.210 | 45.450 | 31.917 | 1.00 | 44.31 | 7 |
| ATOM | 283 | C | LYS | A | 148 | 5.564 | 44.894 | 25.702 | 1.00 | 20.08 | 6 |
| ATOM | 284 | O | LYS | A | 148 | 4.365 | 45.111 | 25.584 | 1.00 | 23.45 | 8 |
| ATOM | 285 | N | THR | A | 149 | 6.509 | 45.375 | 24.919 | 1.00 | 22.66 | 7 |
| ATOM | 286 | CA | THR | A | 149 | 6.199 | 46.426 | 23.955 | 1.00 | 24.54 | 6 |
| ATOM | 287 | CB | THR | A | 149 | 7.501 | 46.993 | 23.359 | 1.00 | 28.59 | 6 |
| ATOM | 288 | OG1 | THR | A | 149 | 8.175 | 47.743 | 24.398 | 1.00 | 27.03 | 8 |
| ATOM | 289 | CG2 | THR | A | 149 | 7.137 | 47.974 | 22.239 | 1.00 | 26.03 | 6 |
| ATOM | 290 | C | THR | A | 149 | 5.444 | 45.829 | 22.784 | 1.00 | 22.31 | 6 |
| ATOM | 291 | O | THR | A | 149 | 4.445 | 46.365 | 22.357 | 1.00 | 23.09 | 8 |
| ATOM | 292 | N | PHE | A | 150 | 5.840 | 44.627 | 22.338 | 1.00 | 20.35 | 7 |
| ATOM | 293 | CA | PHE | A | 150 | 5.032 | 43.967 | 21.295 | 1.00 | 20.84 | 6 |
| ATOM | 294 | CB | PHE | A | 150 | 5.656 | 42.622 | 20.813 | 1.00 | 19.43 | 6 |
| ATOM | 295 | CG | PHE | A | 150 | 6.572 | 42.840 | 19.638 | 1.00 | 19.28 | 6 |
| ATOM | 296 | CD1 | PHE | A | 150 | 7.767 | 43.517 | 19.804 | 1.00 | 23.21 | 6 |
| ATOM | 297 | CD2 | PHE | A | 150 | 6.223 | 42.279 | 18.424 | 1.00 | 22.14 | 6 |
| ATOM | 298 | CE1 | PHE | A | 150 | 8.628 | 43.662 | 18.709 | 1.00 | 24.38 | 6 |
| ATOM | 299 | CE2 | PHE | A | 150 | 7.090 | 42.460 | 17.318 | 1.00 | 26.48 | 6 |
| ATOM | 300 | CZ | PHE | A | 150 | 8.274 | 43.138 | 17.487 | 1.00 | 26.64 | 6 |
| ATOM | 301 | C | PHE | A | 150 | 3.639 | 43.730 | 21.816 | 1.00 | 21.43 | 6 |
| ATOM | 302 | O | PHE | A | 150 | 2.641 | 43.978 | 21.161 | 1.00 | 22.18 | 8 |
| ATOM | 303 | N | HIS | A | 151 | 3.492 | 43.160 | 23.052 | 1.00 | 19.41 | 7 |
| ATOM | 304 | CA | HIS | A | 151 | 2.136 | 42.899 | 23.534 | 1.00 | 20.29 | 6 |

-continued

PDB FILE LISTING –cd81el.pdb

| ATOM | 305 | CB  | HIS | A | 151 | 2.327  | 42.196 | 24.892 | 1.00 | 20.50 | 6  |
| ---- | --- | --- | --- | - | --- | ------ | ------ | ------ | ---- | ----- | -- |
| ATOM | 306 | CG  | HIS | A | 151 | 2.926  | 40.818 | 24.756 | 1.00 | 19.00 | 6  |
| ATOM | 307 | CD2 | HIS | A | 151 | 3.109  | 39.943 | 23.786 | 1.00 | 21.53 | 6  |
| ATOM | 308 | ND1 | HIS | A | 151 | 3.430  | 40.277 | 25.923 | 1.00 | 24.13 | 7  |
| ATOM | 309 | CE1 | HIS | A | 151 | 3.844  | 39.057 | 25.645 | 1.00 | 22.94 | 6  |
| ATOM | 310 | NE2 | HIS | A | 151 | 3.714  | 38.809 | 24.336 | 1.00 | 23.76 | 7  |
| ATOM | 311 | C   | HIS | A | 151 | 1.264  | 44.140 | 23.689 | 1.00 | 17.69 | 6  |
| ATOM | 312 | O   | HIS | A | 151 | 0.092  | 44.031 | 23.367 | 1.00 | 20.84 | 8  |
| ATOM | 313 | N   | GLU | A | 152 | 1.799  | 45.257 | 24.154 | 1.00 | 20.91 | 7  |
| ATOM | 314 | CA  | GLU | A | 152 | 0.990  | 46.458 | 24.397 | 1.00 | 21.45 | 6  |
| ATOM | 315 | CB  | GLU | A | 152 | 1.887  | 47.401 | 25.181 | 1.00 | 24.45 | 6  |
| ATOM | 316 | CG  | GLU | A | 152 | 1.146  | 48.737 | 25.465 | 1.00 | 35.51 | 6  |
| ATOM | 317 | CD  | GLU | A | 152 | 1.910  | 49.450 | 26.575 | 1.00 | 37.49 | 6  |
| ATOM | 318 | OE1 | GLU | A | 152 | 3.012  | 49.946 | 26.243 | 1.00 | 60.98 | 8  |
| ATOM | 319 | OE2 | GLU | A | 152 | 1.409  | 49.523 | 27.706 | 1.00 | 54.52 | 8  |
| ATOM | 320 | C   | GLU | A | 152 | 0.652  | 47.073 | 23.016 | 1.00 | 24.93 | 6  |
| ATOM | 321 | O   | GLU | A | 152 | -0.516 | 47.374 | 22.677 | 1.00 | 26.68 | 8  |
| ATOM | 322 | N   | THR | A | 153 | 1.679  | 47.050 | 22.170 | 1.00 | 22.06 | 7  |
| ATOM | 323 | CA  | THR | A | 153 | 1.553  | 47.631 | 20.837 | 1.00 | 23.76 | 6  |
| ATOM | 324 | CB  | THR | A | 153 | 2.877  | 47.930 | 20.167 | 1.00 | 22.41 | 6  |
| ATOM | 325 | OG1 | THR | A | 153 | 3.719  | 48.778 | 20.982 | 1.00 | 25.19 | 8  |
| ATOM | 326 | CG2 | THR | A | 153 | 2.706  | 48.553 | 18.778 | 1.00 | 26.00 | 6  |
| ATOM | 327 | C   | THR | A | 153 | 0.543  | 46.956 | 19.957 | 1.00 | 25.16 | 6  |
| ATOM | 328 | O   | THR | A | 153 | -0.255 | 47.624 | 19.292 | 1.00 | 27.39 | 8  |
| ATOM | 329 | N   | LEU | A | 154 | 0.581  | 45.631 | 19.880 | 1.00 | 24.12 | 7  |
| ATOM | 330 | CA  | LEU | A | 154 | -0.293 | 44.865 | 19.028 | 1.00 | 24.17 | 6  |
| ATOM | 331 | CB  | LEU | A | 154 | 0.475  | 43.699 | 18.382 | 1.00 | 24.04 | 6  |
| ATOM | 332 | CG  | LEU | A | 154 | 1.735  | 44.158 | 17.692 | 1.00 | 23.64 | 6  |
| ATOM | 333 | CD1 | LEU | A | 154 | 2.505  | 42.926 | 17.202 | 1.00 | 28.71 | 6  |
| ATOM | 334 | CD2 | LEU | A | 154 | 1.410  | 45.020 | 16.462 | 1.00 | 27.37 | 6  |
| ATOM | 335 | C   | LEU | A | 154 | -1.519 | 44.271 | 19.703 | 1.00 | 25.12 | 6  |
| ATOM | 336 | O   | LEU | A | 154 | -2.253 | 43.539 | 19.036 | 1.00 | 30.55 | 8  |
| ATOM | 337 | N   | ASP | A | 155 | -1.650 | 44.490 | 20.998 | 1.00 | 24.04 | 7  |
| ATOM | 338 | CA  | ASP | A | 155 | -2.798 | 43.983 | 21.753 | 1.00 | 26.79 | 6  |
| ATOM | 339 | CB  | ASP | A | 155 | -4.088 | 44.595 | 21.191 | 1.00 | 29.32 | 6  |
| ATOM | 340 | CG  | ASP | A | 155 | -5.288 | 44.195 | 22.049 | 1.00 | 54.63 | 6  |
| ATOM | 341 | OD1 | ASP | A | 155 | -6.418 | 44.190 | 21.500 | 1.00 | 39.24 | 8  |
| ATOM | 342 | OD2 | ASP | A | 155 | -5.082 | 43.899 | 23.250 | 1.00 | 34.92 | 8  |
| ATOM | 343 | C   | ASP | A | 155 | -2.830 | 42.462 | 21.694 | 1.00 | 30.04 | 6  |
| ATOM | 344 | O   | ASP | A | 155 | -3.750 | 41.884 | 21.134 | 1.00 | 29.77 | 8  |
| ATOM | 345 | N   | CYS | A | 156 | -1.738 | 41.816 | 22.153 | 1.00 | 25.38 | 7  |
| ATOM | 346 | CA  | CYS | A | 156 | -1.681 | 40.340 | 22.082 | 1.00 | 25.86 | 6  |
| ATOM | 347 | C   | CYS | A | 156 | -0.797 | 39.854 | 23.234 | 1.00 | 26.35 | 6  |
| ATOM | 348 | O   | CYS | A | 156 | -0.269 | 40.677 | 24.000 | 1.00 | 26.19 | 8  |
| ATOM | 349 | CB  | CYS | A | 156 | -1.078 | 39.839 | 20.742 | 1.00 | 27.96 | 6  |
| ATOM | 350 | SG  | CYS | A | 156 | 0.624  | 40.419 | 20.466 | 1.00 | 24.36 | 16 |
| ATOM | 351 | N   | CYS | A | 157 | -0.843 | 38.518 | 23.399 | 1.00 | 26.36 | 7  |
| ATOM | 352 | CA  | CYS | A | 157 | -0.036 | 37.954 | 24.518 | 1.00 | 27.31 | 6  |
| ATOM | 353 | C   | CYS | A | 157 | 0.314  | 36.526 | 24.086 | 1.00 | 24.36 | 6  |
| ATOM | 354 | O   | CYS | A | 157 | -0.521 | 35.614 | 23.957 | 1.00 | 27.45 | 8  |
| ATOM | 355 | CB  | CYS | A | 157 | -0.965 | 37.922 | 25.747 | 1.00 | 33.17 | 6  |
| ATOM | 356 | SG  | CYS | A | 157 | -0.201 | 37.056 | 27.129 | 1.00 | 32.57 | 16 |
| ATOM | 357 | N   | GLY | A | 158 | 1.578  | 36.266 | 23.759 | 1.00 | 23.62 | 7  |
| ATOM | 358 | CA  | GLY | A | 158 | 1.997  | 34.967 | 23.282 | 1.00 | 23.46 | 6  |
| ATOM | 359 | C   | GLY | A | 158 | 1.882  | 34.721 | 21.802 | 1.00 | 24.98 | 6  |
| ATOM | 360 | O   | GLY | A | 158 | 1.347  | 35.496 | 21.016 | 1.00 | 30.72 | 8  |
| ATOM | 361 | N   | SER | A | 159 | 2.419  | 33.571 | 21.340 | 1.00 | 23.28 | 7  |
| ATOM | 362 | CA  | SER | A | 159 | 2.365  | 33.214 | 19.927 | 1.00 | 25.33 | 6  |
| ATOM | 363 | CB  | SER | A | 159 | 3.627  | 33.414 | 19.111 | 1.00 | 37.04 | 6  |
| ATOM | 364 | OG  | SER | A | 159 | 4.687  | 32.681 | 19.726 | 1.00 | 32.95 | 8  |
| ATOM | 365 | C   | SER | A | 159 | 1.906  | 31.752 | 19.744 | 1.00 | 29.87 | 6  |
| ATOM | 366 | O   | SER | A | 159 | 2.043  | 30.944 | 20.645 | 1.00 | 28.52 | 8  |
| ATOM | 367 | N   | SER | A | 160 | 1.525  | 31.513 | 18.498 | 1.00 | 28.89 | 7  |
| ATOM | 368 | CA  | SER | A | 160 | 1.020  | 30.167 | 18.155 | 1.00 | 31.12 | 6  |
| ATOM | 369 | CB  | SER | A | 160 | 0.229  | 30.282 | 16.851 | 1.00 | 29.35 | 6  |
| ATOM | 370 | OG  | SER | A | 160 | 0.979  | 30.793 | 15.778 | 1.00 | 39.68 | 8  |
| ATOM | 371 | C   | SER | A | 160 | 2.125  | 29.135 | 18.122 | 1.00 | 31.20 | 6  |
| ATOM | 372 | O   | SER | A | 160 | 1.852  | 27.946 | 18.180 | 1.00 | 40.09 | 8  |
| ATOM | 373 | N   | THR | A | 161 | 3.379  | 29.492 | 17.936 | 1.00 | 29.17 | 7  |
| ATOM | 374 | CA  | THR | A | 161 | 4.535  | 28.620 | 17.923 | 1.00 | 31.95 | 6  |
| ATOM | 375 | CB  | THR | A | 161 | 5.728  | 29.296 | 17.195 | 1.00 | 32.45 | 6  |
| ATOM | 376 | OG1 | THR | A | 161 | 5.881  | 30.601 | 17.775 | 1.00 | 30.29 | 8  |
| ATOM | 377 | CG2 | THR | A | 161 | 5.551  | 29.428 | 15.705 | 1.00 | 29.68 | 6  |
| ATOM | 378 | C   | THR | A | 161 | 4.993  | 28.340 | 19.364 | 1.00 | 29.18 | 6  |
| ATOM | 379 | O   | THR | A | 161 | 5.917  | 27.498 | 19.536 | 1.00 | 30.20 | 8  |
| ATOM | 380 | N   | LEU | A | 162 | 4.419  | 29.014 | 20.331 | 1.00 | 25.69 | 7  |
| ATOM | 381 | CA  | LEU | A | 162 | 4.856  | 28.893 | 21.717 | 1.00 | 27.41 | 6  |

-continued

PDB FILE LISTING –cd81el.pdb

| | | | | | | | | | | |
|---|---|---|---|---|---|---|---|---|---|---|
| ATOM | 382 | CB | LEU | A | 162 | 5.756 | 30.118 | 22.008 | 1.00 | 23.42 | 6 |
| ATOM | 383 | CG | LEU | A | 162 | 7.098 | 30.162 | 21.291 | 1.00 | 24.84 | 6 |
| ATOM | 384 | CD1 | LEU | A | 162 | 7.779 | 31.516 | 21.585 | 1.00 | 23.56 | 6 |
| ATOM | 385 | CD2 | LEU | A | 162 | 8.040 | 29.030 | 21.756 | 1.00 | 25.57 | 6 |
| ATOM | 386 | C | LEU | A | 162 | 3.724 | 28.789 | 22.704 | 1.00 | 27.32 | 6 |
| ATOM | 387 | O | LEU | A | 162 | 3.776 | 29.267 | 23.841 | 1.00 | 25.57 | 8 |
| ATOM | 388 | N | THR | A | 163 | 2.651 | 28.111 | 22.252 | 1.00 | 33.24 | 7 |
| ATOM | 389 | CA | THR | A | 163 | 1.435 | 27.945 | 23.005 | 1.00 | 34.43 | 6 |
| ATOM | 390 | CB | THR | A | 163 | 0.321 | 27.242 | 22.231 | 1.00 | 47.90 | 6 |
| ATOM | 391 | OG1 | THR | A | 163 | 0.574 | 25.833 | 22.222 | 1.00 | 41.55 | 8 |
| ATOM | 392 | CG2 | THR | A | 163 | 0.333 | 27.684 | 20.769 | 1.00 | 37.28 | 6 |
| ATOM | 393 | C | THR | A | 163 | 1.633 | 27.365 | 24.386 | 1.00 | 33.67 | 6 |
| ATOM | 394 | O | THR | A | 163 | 1.027 | 27.836 | 25.334 | 1.00 | 37.42 | 8 |
| ATOM | 395 | N | ALA | A | 164 | 2.588 | 26.420 | 24.481 | 1.00 | 34.03 | 7 |
| ATOM | 396 | CA | ALA | A | 164 | 2.861 | 25.891 | 25.801 | 1.00 | 33.86 | 6 |
| ATOM | 397 | CB | ALA | A | 164 | 3.368 | 24.474 | 25.747 | 1.00 | 38.55 | 6 |
| ATOM | 398 | C | ALA | A | 164 | 3.581 | 26.799 | 26.735 | 1.00 | 34.37 | 6 |
| ATOM | 399 | O | ALA | A | 164 | 3.702 | 26.455 | 27.918 | 1.00 | 32.28 | 8 |
| ATOM | 400 | N | LEU | A | 165 | 4.067 | 27.970 | 26.286 | 1.00 | 33.08 | 7 |
| ATOM | 401 | CA | LEU | A | 165 | 4.711 | 28.931 | 27.152 | 1.00 | 31.61 | 6 |
| ATOM | 402 | CB | LEU | A | 165 | 5.768 | 29.707 | 26.306 | 1.00 | 27.45 | 6 |
| ATOM | 403 | CG | LEU | A | 165 | 7.210 | 29.476 | 26.442 | 1.00 | 27.02 | 6 |
| ATOM | 404 | CD1 | LEU | A | 165 | 8.028 | 30.517 | 25.763 | 1.00 | 24.12 | 6 |
| ATOM | 405 | CD2 | LEU | A | 165 | 7.803 | 28.611 | 27.487 | 1.00 | 27.64 | 6 |
| ATOM | 406 | C | LEU | A | 165 | 3.814 | 30.032 | 27.651 | 1.00 | 29.91 | 6 |
| ATOM | 407 | O | LEU | A | 165 | 4.166 | 30.745 | 28.591 | 1.00 | 31.12 | 8 |
| ATOM | 408 | N | THR | A | 166 | 2.565 | 30.108 | 27.104 | 1.00 | 32.70 | 7 |
| ATOM | 409 | CA | THR | A | 166 | 1.679 | 31.174 | 27.587 | 1.00 | 39.86 | 6 |
| ATOM | 410 | CB | THR | A | 166 | 0.417 | 31.275 | 26.724 | 1.00 | 36.59 | 6 |
| ATOM | 411 | OG1 | THR | A | 166 | 0.772 | 31.283 | 25.342 | 1.00 | 36.37 | 8 |
| ATOM | 412 | CG2 | THR | A | 166 | −0.426 | 32.496 | 27.035 | 1.00 | 43.25 | 6 |
| ATOM | 413 | C | THR | A | 166 | 1.507 | 31.273 | 29.078 | 1.00 | 40.96 | 6 |
| ATOM | 414 | O | THR | A | 166 | 1.550 | 32.372 | 29.663 | 1.00 | 38.71 | 8 |
| ATOM | 415 | N | THR | A | 167 | 1.389 | 30.162 | 29.818 | 1.00 | 41.60 | 7 |
| ATOM | 416 | CA | THR | A | 167 | 1.264 | 30.185 | 31.258 | 1.00 | 41.06 | 6 |
| ATOM | 417 | CB | THR | A | 167 | 1.145 | 28.770 | 31.877 | 1.00 | 56.92 | 6 |
| ATOM | 418 | OG1 | THR | A | 167 | 0.505 | 27.882 | 30.956 | 1.00 | 64.37 | 8 |
| ATOM | 419 | CG2 | THR | A | 167 | 0.315 | 28.860 | 33.144 | 1.00 | 53.26 | 6 |
| ATOM | 420 | C | THR | A | 167 | 2.386 | 30.920 | 31.965 | 1.00 | 38.21 | 6 |
| ATOM | 421 | O | THR | A | 167 | 2.297 | 31.748 | 32.872 | 1.00 | 38.00 | 8 |
| ATOM | 422 | N | SER | A | 168 | 3.588 | 30.592 | 31.464 | 1.00 | 36.02 | 7 |
| ATOM | 423 | CA | SER | A | 168 | 4.823 | 31.175 | 31.912 | 1.00 | 32.03 | 6 |
| ATOM | 424 | CB | SER | A | 168 | 5.950 | 30.393 | 31.219 | 1.00 | 39.61 | 6 |
| ATOM | 425 | OG | SER | A | 168 | 7.128 | 30.624 | 31.944 | 1.00 | 41.71 | 8 |
| ATOM | 426 | C | SER | A | 168 | 4.884 | 32.652 | 31.518 | 1.00 | 30.79 | 6 |
| ATOM | 427 | O | SER | A | 168 | 5.266 | 33.502 | 32.301 | 1.00 | 33.91 | 8 |
| ATOM | 428 | N | VAL | A | 169 | 4.426 | 32.962 | 30.314 | 1.00 | 35.38 | 7 |
| ATOM | 429 | CA | VAL | A | 169 | 4.455 | 34.357 | 29.876 | 1.00 | 27.71 | 6 |
| ATOM | 430 | CB | VAL | A | 169 | 4.121 | 34.448 | 28.385 | 1.00 | 29.96 | 6 |
| ATOM | 431 | CG1 | VAL | A | 169 | 4.086 | 35.924 | 27.943 | 1.00 | 25.54 | 6 |
| ATOM | 432 | CG2 | VAL | A | 169 | 5.195 | 33.724 | 27.582 | 1.00 | 33.79 | 6 |
| ATOM | 433 | C | VAL | A | 169 | 3.604 | 35.213 | 30.817 | 1.00 | 32.85 | 6 |
| ATOM | 434 | O | VAL | A | 169 | 3.951 | 36.282 | 31.333 | 1.00 | 35.86 | 8 |
| ATOM | 435 | N | LEU | A | 170 | 2.431 | 34.704 | 31.152 | 1.00 | 35.39 | 7 |
| ATOM | 436 | CA | LEU | A | 170 | 1.500 | 35.385 | 32.050 | 1.00 | 39.23 | 6 |
| ATOM | 437 | CB | LEU | A | 170 | 0.244 | 34.542 | 32.100 | 1.00 | 35.15 | 6 |
| ATOM | 438 | CG | LEU | A | 170 | −0.801 | 34.822 | 31.014 | 1.00 | 38.80 | 6 |
| ATOM | 439 | CD1 | LEU | A | 170 | −2.126 | 34.272 | 31.565 | 1.00 | 42.41 | 6 |
| ATOM | 440 | CD2 | LEU | A | 170 | −0.976 | 36.292 | 30.731 | 1.00 | 45.02 | 6 |
| ATOM | 441 | C | LEU | A | 170 | 2.081 | 35.543 | 33.439 | 1.00 | 37.13 | 6 |
| ATOM | 442 | O | LEU | A | 170 | 2.037 | 36.613 | 34.032 | 1.00 | 38.03 | 8 |
| ATOM | 443 | N | LYS | A | 171 | 2.655 | 34.441 | 33.932 | 1.00 | 39.80 | 7 |
| ATOM | 444 | CA | LYS | A | 171 | 3.240 | 34.460 | 35.275 | 1.00 | 44.19 | 6 |
| ATOM | 445 | CB | LYS | A | 171 | 3.846 | 33.078 | 35.586 | 1.00 | 61.33 | 6 |
| ATOM | 446 | CG | LYS | A | 171 | 4.568 | 33.045 | 36.927 | 1.00 | 70.55 | 6 |
| ATOM | 447 | CD | LYS | A | 171 | 3.614 | 33.375 | 38.065 | 1.00 | 82.76 | 6 |
| ATOM | 448 | CE | LYS | A | 171 | 4.325 | 33.536 | 39.396 | 1.00 | 86.15 | 6 |
| ATOM | 449 | NZ | LYS | A | 171 | 3.605 | 34.470 | 40.306 | 1.00 | 86.50 | 7 |
| ATOM | 450 | C | LYS | A | 171 | 4.330 | 35.495 | 35.417 | 1.00 | 42.25 | 6 |
| ATOM | 451 | O | LYS | A | 171 | 4.501 | 36.069 | 36.505 | 1.00 | 40.60 | 8 |
| ATOM | 452 | N | ASN | A | 172 | 5.098 | 35.697 | 34.326 | 1.00 | 34.05 | 7 |
| ATOM | 453 | CA | ASN | A | 172 | 6.151 | 36.713 | 34.380 | 1.00 | 32.66 | 6 |
| ATOM | 454 | CB | ASN | A | 172 | 7.200 | 36.380 | 33.287 | 1.00 | 39.13 | 6 |
| ATOM | 455 | CG | ASN | A | 172 | 8.163 | 35.288 | 33.667 | 1.00 | 44.80 | 6 |
| ATOM | 456 | OD1 | ASN | A | 172 | 9.197 | 35.585 | 34.263 | 1.00 | 49.14 | 8 |
| ATOM | 457 | ND2 | ASN | A | 172 | 7.897 | 34.039 | 33.329 | 1.00 | 37.24 | 7 |
| ATOM | 458 | C | ASN | A | 172 | 5.661 | 38.135 | 34.153 | 1.00 | 32.11 | 6 |

-continued

PDB FILE LISTING –cd81el.pdb

| ATOM | 459 | O | ASN | A | 172 | 6.468 | 39.055 | 33.977 | 1.00 | 34.88 | 8 |
|------|-----|-----|-----|---|-----|--------|--------|--------|------|-------|---|
| ATOM | 460 | N | ASN | A | 173 | 4.358 | 38.394 | 34.203 | 1.00 | 31.68 | 7 |
| ATOM | 461 | CA | ASN | A | 173 | 3.768 | 39.716 | 34.061 | 1.00 | 29.24 | 6 |
| ATOM | 462 | CB | ASN | A | 173 | 4.009 | 40.629 | 35.235 | 1.00 | 35.84 | 6 |
| ATOM | 463 | CG | ASN | A | 173 | 3.450 | 39.955 | 36.506 | 1.00 | 36.42 | 6 |
| ATOM | 464 | OD1 | ASN | A | 173 | 2.591 | 39.085 | 36.396 | 1.00 | 39.55 | 8 |
| ATOM | 465 | ND2 | ASN | A | 173 | 4.002 | 40.381 | 37.626 | 1.00 | 53.62 | 7 |
| ATOM | 466 | C | ASN | A | 173 | 4.197 | 40.404 | 32.740 | 1.00 | 29.47 | 6 |
| ATOM | 467 | O | ASN | A | 173 | 4.307 | 41.640 | 32.703 | 1.00 | 32.55 | 8 |
| ATOM | 468 | N | LEU | A | 174 | 4.282 | 39.567 | 31.697 | 1.00 | 31.56 | 7 |
| ATOM | 469 | CA | LEU | A | 174 | 4.668 | 40.131 | 30.389 | 1.00 | 27.42 | 6 |
| ATOM | 470 | CB | LEU | A | 174 | 5.487 | 39.094 | 29.567 | 1.00 | 27.30 | 6 |
| ATOM | 471 | CG | LEU | A | 174 | 6.789 | 38.694 | 30.298 | 1.00 | 29.12 | 6 |
| ATOM | 472 | CD1 | LEU | A | 174 | 7.411 | 37.496 | 29.567 | 1.00 | 28.87 | 6 |
| ATOM | 473 | CD2 | LEU | A | 174 | 7.755 | 39.890 | 30.307 | 1.00 | 30.51 | 6 |
| ATOM | 474 | C | LEU | A | 174 | 3.472 | 40.556 | 29.553 | 1.00 | 30.31 | 6 |
| ATOM | 475 | O | LEU | A | 174 | 3.738 | 41.133 | 28.468 | 1.00 | 26.30 | 8 |
| ATOM | 476 | N | CYS | A | 175 | 2.255 | 40.276 | 30.006 | 1.00 | 30.27 | 7 |
| ATOM | 477 | CA | CYS | A | 175 | 1.110 | 40.728 | 29.213 | 1.00 | 30.49 | 6 |
| ATOM | 478 | C | CYS | A | 175 | 0.364 | 41.868 | 29.883 | 1.00 | 30.71 | 6 |
| ATOM | 479 | O | CYS | A | 175 | 0.383 | 41.960 | 31.119 | 1.00 | 28.85 | 8 |
| ATOM | 480 | CB | CYS | A | 175 | 0.225 | 39.531 | 28.885 | 1.00 | 33.22 | 6 |
| ATOM | 481 | SG | CYS | A | 175 | 1.157 | 38.382 | 27.797 | 1.00 | 34.32 | 16 |
| ATOM | 482 | N | PRO | A | 176 | −0.216 | 42.747 | 29.126 | 1.00 | 27.02 | 7 |
| ATOM | 483 | CD | PRO | A | 176 | −0.202 | 42.778 | 27.620 | 1.00 | 27.31 | 6 |
| ATOM | 484 | CA | PRO | A | 176 | −1.031 | 43.860 | 29.607 | 1.00 | 29.02 | 6 |
| ATOM | 485 | CB | PRO | A | 176 | −1.802 | 44.330 | 28.356 | 1.00 | 30.75 | 6 |
| ATOM | 486 | CG | PRO | A | 176 | −0.681 | 44.201 | 27.369 | 1.00 | 29.79 | 6 |
| ATOM | 487 | C | PRO | A | 176 | −2.061 | 43.417 | 30.656 | 1.00 | 28.74 | 6 |
| ATOM | 488 | O | PRO | A | 176 | −2.600 | 42.326 | 30.586 | 1.00 | 29.00 | 8 |
| ATOM | 489 | N | SER | A | 177 | −2.232 | 44.390 | 31.582 | 1.00 | 30.95 | 7 |
| ATOM | 490 | CA | SER | A | 177 | −3.173 | 44.142 | 32.688 | 1.00 | 35.36 | 6 |
| ATOM | 491 | CB | SER | A | 177 | −3.415 | 45.461 | 33.435 | 1.00 | 36.82 | 6 |
| ATOM | 492 | OG | SER | A | 177 | −2.202 | 46.102 | 33.764 | 1.00 | 45.84 | 8 |
| ATOM | 493 | C | SER | A | 177 | −4.485 | 43.656 | 32.120 | 1.00 | 38.68 | 6 |
| ATOM | 494 | O | SER | A | 177 | −4.918 | 44.231 | 31.107 | 1.00 | 42.81 | 8 |
| ATOM | 495 | N | GLY | A | 178 | −5.101 | 42.644 | 32.713 | 1.00 | 42.54 | 7 |
| ATOM | 496 | CA | GLY | A | 178 | −6.357 | 42.145 | 32.183 | 1.00 | 44.10 | 6 |
| ATOM | 497 | C | GLY | A | 178 | −6.180 | 40.771 | 31.571 | 1.00 | 47.58 | 6 |
| ATOM | 498 | O | GLY | A | 178 | −7.075 | 39.934 | 31.641 | 1.00 | 48.95 | 8 |
| ATOM | 499 | N | SER | A | 179 | −5.012 | 40.548 | 30.951 | 1.00 | 42.04 | 7 |
| ATOM | 500 | CA | SER | A | 179 | −4.715 | 39.262 | 30.363 | 1.00 | 39.16 | 6 |
| ATOM | 501 | CB | SER | A | 179 | −3.278 | 39.360 | 29.771 | 1.00 | 35.52 | 6 |
| ATOM | 502 | OG | SER | A | 179 | −3.444 | 40.056 | 28.515 | 1.00 | 44.97 | 8 |
| ATOM | 503 | C | SER | A | 179 | −4.702 | 38.152 | 31.410 | 1.00 | 41.15 | 6 |
| ATOM | 504 | O | SER | A | 179 | −4.185 | 38.285 | 32.522 | 1.00 | 38.03 | 8 |
| ATOM | 505 | N | ASN | A | 180 | −5.273 | 37.027 | 31.030 | 1.00 | 37.43 | 7 |
| ATOM | 506 | CA | ASN | A | 180 | −5.370 | 35.833 | 31.843 | 1.00 | 38.91 | 6 |
| ATOM | 507 | CB | ASN | A | 180 | −6.498 | 35.968 | 32.868 | 1.00 | 43.64 | 6 |
| ATOM | 508 | CG | ASN | A | 180 | −7.760 | 36.496 | 32.206 | 1.00 | 50.72 | 6 |
| ATOM | 509 | OD1 | ASN | A | 180 | −7.969 | 37.713 | 32.184 | 1.00 | 47.95 | 8 |
| ATOM | 510 | ND2 | ASN | A | 180 | −8.569 | 35.607 | 31.652 | 1.00 | 40.10 | 7 |
| ATOM | 511 | C | ASN | A | 180 | −5.659 | 34.707 | 30.844 | 1.00 | 39.79 | 6 |
| ATOM | 512 | O | ASN | A | 180 | −5.906 | 35.014 | 29.664 | 1.00 | 41.96 | 8 |
| ATOM | 513 | N | ILE | A | 181 | −5.508 | 33.473 | 31.256 | 1.00 | 40.01 | 7 |
| ATOM | 514 | CA | ILE | A | 181 | −5.631 | 32.321 | 30.375 | 1.00 | 35.08 | 6 |
| ATOM | 515 | CB | ILE | A | 181 | −5.369 | 31.007 | 31.114 | 1.00 | 43.35 | 6 |
| ATOM | 516 | CG2 | ILE | A | 181 | −6.180 | 30.867 | 32.394 | 1.00 | 50.56 | 6 |
| ATOM | 517 | CG1 | ILE | A | 181 | −5.664 | 29.800 | 30.226 | 1.00 | 37.17 | 6 |
| ATOM | 518 | CD1 | ILE | A | 181 | −5.177 | 28.476 | 30.772 | 1.00 | 61.09 | 6 |
| ATOM | 519 | C | ILE | A | 181 | −6.930 | 32.343 | 29.593 | 1.00 | 38.56 | 6 |
| ATOM | 520 | O | ILE | A | 181 | −6.896 | 32.286 | 28.357 | 1.00 | 39.50 | 8 |
| ATOM | 521 | N | ILE | A | 182 | −8.065 | 32.520 | 30.276 | 1.00 | 31.14 | 7 |
| ATOM | 522 | CA | ILE | A | 182 | −9.323 | 32.541 | 29.548 | 1.00 | 33.99 | 6 |
| ATOM | 523 | CB | ILE | A | 182 | −10.590 | 32.395 | 30.398 | 1.00 | 35.20 | 6 |
| ATOM | 524 | CG2 | ILE | A | 182 | −11.798 | 32.450 | 29.440 | 1.00 | 38.49 | 6 |
| ATOM | 525 | CG1 | ILE | A | 182 | −10.615 | 30.996 | 31.030 | 1.00 | 33.92 | 6 |
| ATOM | 526 | CD1 | ILE | A | 182 | −11.972 | 30.794 | 31.679 | 1.00 | 41.51 | 6 |
| ATOM | 527 | C | ILE | A | 182 | −9.453 | 33.664 | 28.548 | 1.00 | 33.21 | 6 |
| ATOM | 528 | O | ILE | A | 182 | −9.686 | 33.395 | 27.358 | 1.00 | 32.00 | 8 |
| ATOM | 529 | N | SER | A | 183 | −9.300 | 34.909 | 28.992 | 1.00 | 32.06 | 7 |
| ATOM | 530 | CA | SER | A | 183 | −9.481 | 36.019 | 28.046 | 1.00 | 30.17 | 6 |
| ATOM | 531 | CB | SER | A | 183 | −9.173 | 37.363 | 28.705 | 1.00 | 40.84 | 6 |
| ATOM | 532 | OG | SER | A | 183 | −7.832 | 37.387 | 29.180 | 1.00 | 50.43 | 8 |
| ATOM | 533 | C | SER | A | 183 | −8.539 | 35.849 | 26.867 | 1.00 | 29.79 | 6 |
| ATOM | 534 | O | SER | A | 183 | −8.841 | 36.209 | 25.719 | 1.00 | 30.43 | 8 |
| ATOM | 535 | N | ASN | A | 184 | −7.325 | 35.342 | 27.158 | 1.00 | 29.85 | 7 |

-continued

PDB FILE LISTING –cd81el.pdb

| ATOM | 536 | CA | ASN | A | 184 | −6.366 | 35.206 | 26.073 | 1.00 | 29.42 | 6 |
| ATOM | 537 | CB | ASN | A | 184 | −4.954 | 35.100 | 26.613 | 1.00 | 32.69 | 6 |
| ATOM | 538 | CG | ASN | A | 184 | −3.909 | 35.579 | 25.617 | 1.00 | 39.32 | 6 |
| ATOM | 539 | OD1 | ASN | A | 184 | −3.902 | 36.737 | 25.180 | 1.00 | 38.73 | 8 |
| ATOM | 540 | ND2 | ASN | A | 184 | −3.026 | 34.659 | 25.253 | 1.00 | 37.01 | 7 |
| ATOM | 541 | C | ASN | A | 184 | −6.767 | 34.168 | 25.046 | 1.00 | 29.90 | 6 |
| ATOM | 542 | O | ASN | A | 184 | −6.416 | 34.312 | 23.886 | 1.00 | 30.55 | 8 |
| ATOM | 543 | N | LEU | A | 185 | −7.594 | 33.180 | 25.400 | 1.00 | 28.17 | 7 |
| ATOM | 544 | CA | LEU | A | 185 | −8.022 | 32.190 | 24.418 | 1.00 | 28.14 | 6 |
| ATOM | 545 | CB | LEU | A | 185 | −8.792 | 31.069 | 25.170 | 1.00 | 31.80 | 6 |
| ATOM | 546 | CG | LEU | A | 185 | −7.873 | 30.228 | 26.077 | 1.00 | 37.24 | 6 |
| ATOM | 547 | CD1 | LEU | A | 185 | −8.734 | 29.247 | 26.874 | 1.00 | 38.22 | 6 |
| ATOM | 548 | CD2 | LEU | A | 185 | −6.862 | 29.482 | 25.200 | 1.00 | 30.41 | 6 |
| ATOM | 549 | C | LEU | A | 185 | −8.978 | 32.794 | 23.390 | 1.00 | 25.61 | 6 |
| ATOM | 550 | O | LEU | A | 185 | −9.127 | 32.198 | 22.304 | 1.00 | 29.28 | 8 |
| ATOM | 551 | N | PHE | A | 186 | −9.577 | 33.930 | 23.688 | 1.00 | 25.10 | 7 |
| ATOM | 552 | CA | PHE | A | 186 | −10.524 | 34.523 | 22.720 | 1.00 | 28.91 | 6 |
| ATOM | 553 | CB | PHE | A | 186 | −11.725 | 35.124 | 23.488 | 1.00 | 28.71 | 6 |
| ATOM | 554 | CG | PHE | A | 186 | −12.636 | 34.083 | 24.083 | 1.00 | 31.64 | 6 |
| ATOM | 555 | CD1 | PHE | A | 186 | −12.428 | 33.583 | 25.332 | 1.00 | 30.09 | 6 |
| ATOM | 556 | CD2 | PHE | A | 186 | −13.724 | 33.670 | 23.346 | 1.00 | 29.23 | 6 |
| ATOM | 557 | CE1 | PHE | A | 186 | −13.280 | 32.604 | 25.875 | 1.00 | 34.13 | 6 |
| ATOM | 558 | CE2 | PHE | A | 186 | −14.599 | 32.724 | 23.893 | 1.00 | 27.11 | 6 |
| ATOM | 559 | CZ | PHE | A | 186 | −14.364 | 32.192 | 25.124 | 1.00 | 31.22 | 6 |
| ATOM | 560 | C | PHE | A | 186 | −9.888 | 35.661 | 21.919 | 1.00 | 28.36 | 6 |
| ATOM | 561 | O | PHE | A | 186 | −10.575 | 36.472 | 21.302 | 1.00 | 30.96 | 8 |
| ATOM | 562 | N | LYS | A | 187 | −8.558 | 35.744 | 21.959 | 1.00 | 29.55 | 7 |
| ATOM | 563 | CA | LYS | A | 187 | −7.849 | 36.800 | 21.204 | 1.00 | 30.12 | 6 |
| ATOM | 564 | CB | LYS | A | 187 | −6.981 | 37.575 | 22.229 | 1.00 | 30.88 | 6 |
| ATOM | 565 | CG | LYS | A | 187 | −7.821 | 38.654 | 22.890 | 1.00 | 43.39 | 6 |
| ATOM | 566 | CD | LYS | A | 187 | −7.047 | 39.391 | 23.958 | 1.00 | 48.15 | 6 |
| ATOM | 567 | CE | LYS | A | 187 | −6.085 | 40.405 | 23.339 | 1.00 | 41.67 | 6 |
| ATOM | 568 | NZ | LYS | A | 187 | −5.759 | 41.430 | 24.369 | 1.00 | 42.64 | 7 |
| ATOM | 569 | C | LYS | A | 187 | −6.869 | 36.185 | 20.213 | 1.00 | 27.72 | 6 |
| ATOM | 570 | O | LYS | A | 187 | −6.370 | 35.086 | 20.445 | 1.00 | 28.84 | 8 |
| ATOM | 571 | N | GLU | A | 188 | −6.606 | 36.916 | 19.110 | 1.00 | 26.40 | 7 |
| ATOM | 572 | CA | GLU | A | 188 | −5.608 | 36.498 | 18.144 | 1.00 | 24.95 | 6 |
| ATOM | 573 | CB | GLU | A | 188 | −5.558 | 37.520 | 16.994 | 1.00 | 30.53 | 6 |
| ATOM | 574 | CG | GLU | A | 188 | −6.924 | 37.605 | 16.315 | 1.00 | 39.56 | 6 |
| ATOM | 575 | CD | GLU | A | 188 | −6.932 | 38.457 | 15.068 | 1.00 | 58.60 | 6 |
| ATOM | 576 | OE1 | GLU | A | 188 | −6.597 | 39.661 | 15.133 | 1.00 | 57.62 | 8 |
| ATOM | 577 | OE2 | GLU | A | 188 | −7.290 | 37.897 | 14.009 | 1.00 | 64.79 | 8 |
| ATOM | 578 | C | GLU | A | 188 | −4.194 | 36.601 | 18.808 | 1.00 | 20.96 | 6 |
| ATOM | 579 | O | GLU | A | 188 | −4.014 | 37.439 | 19.683 | 1.00 | 25.27 | 8 |
| ATOM | 580 | N | ASP | A | 189 | −3.380 | 35.673 | 18.394 | 1.00 | 25.32 | 7 |
| ATOM | 581 | CA | ASP | A | 189 | −2.027 | 35.623 | 18.967 | 1.00 | 22.63 | 6 |
| ATOM | 582 | CB | ASP | A | 189 | −1.380 | 34.237 | 18.781 | 1.00 | 28.31 | 6 |
| ATOM | 583 | CG | ASP | A | 189 | −0.770 | 34.114 | 17.422 | 1.00 | 24.61 | 6 |
| ATOM | 584 | OD1 | ASP | A | 189 | 0.473 | 33.884 | 17.302 | 1.00 | 27.48 | 8 |
| ATOM | 585 | OD2 | ASP | A | 189 | −1.347 | 34.337 | 16.351 | 1.00 | 35.01 | 8 |
| ATOM | 586 | C | ASP | A | 189 | −1.167 | 36.691 | 18.300 | 1.00 | 22.86 | 6 |
| ATOM | 587 | O | ASP | A | 189 | −1.537 | 37.330 | 17.273 | 1.00 | 24.00 | 8 |
| ATOM | 588 | N | CYS | A | 190 | 0.065 | 36.811 | 18.805 | 1.00 | 22.75 | 7 |
| ATOM | 589 | CA | CYS | A | 190 | 0.956 | 37.851 | 18.216 | 1.00 | 21.64 | 6 |
| ATOM | 590 | C | CYS | A | 190 | 1.352 | 37.562 | 16.782 | 1.00 | 21.74 | 6 |
| ATOM | 591 | O | CYS | A | 190 | 1.569 | 38.596 | 16.081 | 1.00 | 24.29 | 8 |
| ATOM | 592 | CB | CYS | A | 190 | 2.133 | 38.128 | 19.101 | 1.00 | 23.60 | 6 |
| ATOM | 593 | SG | CYS | A | 190 | 1.730 | 38.711 | 20.756 | 1.00 | 26.96 | 16 |
| ATOM | 594 | N | HIS | A | 191 | 1.496 | 36.339 | 16.299 | 1.00 | 22.50 | 7 |
| ATOM | 595 | CA | HIS | A | 191 | 1.881 | 36.196 | 14.901 | 1.00 | 21.71 | 6 |
| ATOM | 596 | CB | HIS | A | 191 | 2.232 | 34.740 | 14.596 | 1.00 | 26.64 | 6 |
| ATOM | 597 | CG | HIS | A | 191 | 3.551 | 34.362 | 15.222 | 1.00 | 26.82 | 6 |
| ATOM | 598 | CD2 | HIS | A | 191 | 4.355 | 34.965 | 16.093 | 1.00 | 26.94 | 6 |
| ATOM | 599 | ND1 | HIS | A | 191 | 4.129 | 33.171 | 14.866 | 1.00 | 29.12 | 7 |
| ATOM | 600 | CE1 | HIS | A | 191 | 5.285 | 33.094 | 15.532 | 1.00 | 25.60 | 6 |
| ATOM | 601 | NE2 | HIS | A | 191 | 5.427 | 34.114 | 16.334 | 1.00 | 25.91 | 7 |
| ATOM | 602 | C | HIS | A | 191 | 0.831 | 36.773 | 14.002 | 1.00 | 21.74 | 6 |
| ATOM | 603 | O | HIS | A | 191 | 1.141 | 37.315 | 12.904 | 1.00 | 24.92 | 8 |
| ATOM | 604 | N | GLN | A | 192 | −0.436 | 36.475 | 14.363 | 1.00 | 26.00 | 7 |
| ATOM | 605 | CA | GLN | A | 192 | −1.530 | 36.988 | 13.529 | 1.00 | 26.00 | 6 |
| ATOM | 606 | CB | GLN | A | 192 | −2.890 | 36.549 | 14.130 | 1.00 | 25.26 | 6 |
| ATOM | 607 | CG | GLN | A | 192 | −3.979 | 37.056 | 13.177 | 1.00 | 36.23 | 6 |
| ATOM | 608 | CD | GLN | A | 192 | −3.954 | 36.524 | 11.775 | 1.00 | 42.56 | 6 |
| ATOM | 609 | OE1 | GLN | A | 192 | −4.126 | 35.350 | 11.486 | 1.00 | 46.38 | 8 |
| ATOM | 610 | NE2 | GLN | A | 192 | −3.772 | 37.366 | 10.753 | 1.00 | 34.35 | 7 |
| ATOM | 611 | C | GLN | A | 192 | −1.505 | 38.503 | 13.534 | 1.00 | 25.56 | 6 |
| ATOM | 612 | O | GLN | A | 192 | −1.717 | 39.139 | 12.485 | 1.00 | 25.01 | 8 |

-continued

PDB FILE LISTING – cd81el.pdb

| ATOM | 613 | N | LYS | A | 193 | −1.318 | 39.155 | 14.685 | 1.00 | 22.99 | 7 |
|------|-----|-----|-----|---|-----|--------|--------|--------|------|-------|---|
| ATOM | 614 | CA | LYS | A | 193 | −1.206 | 40.597 | 14.767 | 1.00 | 21.22 | 6 |
| ATOM | 615 | CB | LYS | A | 193 | −1.188 | 41.124 | 16.218 | 1.00 | 20.84 | 6 |
| ATOM | 616 | CG | LYS | A | 193 | −2.495 | 40.778 | 16.896 | 1.00 | 22.00 | 6 |
| ATOM | 617 | CD | LYS | A | 193 | −3.688 | 41.482 | 16.250 | 1.00 | 28.69 | 6 |
| ATOM | 618 | CE | LYS | A | 193 | −4.963 | 41.573 | 17.081 | 1.00 | 42.13 | 6 |
| ATOM | 619 | NZ | LYS | A | 193 | −4.903 | 42.588 | 18.149 | 1.00 | 42.68 | 7 |
| ATOM | 620 | C | LYS | A | 193 | −0.033 | 41.140 | 13.970 | 1.00 | 23.50 | 6 |
| ATOM | 621 | O | LYS | A | 193 | −0.182 | 42.216 | 13.366 | 1.00 | 24.64 | 8 |
| ATOM | 622 | N | ILE | A | 194 | 1.095 | 40.444 | 13.924 | 1.00 | 20.30 | 7 |
| ATOM | 623 | CA | ILE | A | 194 | 2.211 | 40.878 | 13.074 | 1.00 | 22.70 | 6 |
| ATOM | 624 | CB | ILE | A | 194 | 3.436 | 39.972 | 13.318 | 1.00 | 22.09 | 6 |
| ATOM | 625 | CG2 | ILE | A | 194 | 4.487 | 40.101 | 12.184 | 1.00 | 23.81 | 6 |
| ATOM | 626 | CG1 | ILE | A | 194 | 3.920 | 40.404 | 14.714 | 1.00 | 20.79 | 6 |
| ATOM | 627 | CD1 | ILE | A | 194 | 4.915 | 39.428 | 15.349 | 1.00 | 24.12 | 6 |
| ATOM | 628 | C | ILE | A | 194 | 1.767 | 40.836 | 11.632 | 1.00 | 22.66 | 6 |
| ATOM | 629 | O | ILE | A | 194 | 1.942 | 41.791 | 10.879 | 1.00 | 23.54 | 8 |
| ATOM | 630 | N | ASP | A | 195 | 1.079 | 39.728 | 11.287 | 1.00 | 25.86 | 7 |
| ATOM | 631 | CA | ASP | A | 195 | 0.636 | 39.644 | 9.875 | 1.00 | 28.42 | 6 |
| ATOM | 632 | CB | ASP | A | 195 | −0.154 | 38.334 | 9.694 | 1.00 | 30.81 | 6 |
| ATOM | 633 | CG | ASP | A | 195 | 0.736 | 37.219 | 9.172 | 1.00 | 43.61 | 6 |
| ATOM | 634 | OD1 | ASP | A | 195 | 0.354 | 36.035 | 9.317 | 1.00 | 40.90 | 8 |
| ATOM | 635 | OD2 | ASP | A | 195 | 1.786 | 37.567 | 8.637 | 1.00 | 40.27 | 6 |
| ATOM | 636 | C | ASP | A | 195 | −0.330 | 40.800 | 9.581 | 1.00 | 25.57 | 6 |
| ATOM | 637 | O | ASP | A | 195 | −0.257 | 41.436 | 8.510 | 1.00 | 28.18 | 8 |
| ATOM | 638 | N | ASP | A | 196 | −1.223 | 41.116 | 10.487 | 1.00 | 25.86 | 7 |
| ATOM | 639 | CA | ASP | A | 196 | −2.214 | 42.186 | 10.297 | 1.00 | 27.70 | 6 |
| ATOM | 640 | CB | ASP | A | 196 | −3.190 | 42.304 | 11.477 | 1.00 | 27.67 | 6 |
| ATOM | 641 | CG | ASP | A | 196 | −4.130 | 41.117 | 11.536 | 1.00 | 35.55 | 6 |
| ATOM | 642 | OD1 | ASP | A | 196 | −4.182 | 40.386 | 10.527 | 1.00 | 37.44 | 8 |
| ATOM | 643 | OD2 | ASP | A | 196 | −4.830 | 40.899 | 12.549 | 1.00 | 40.00 | 8 |
| ATOM | 644 | C | ASP | A | 196 | −1.520 | 43.522 | 10.070 | 1.00 | 30.21 | 6 |
| ATOM | 645 | O | ASP | A | 196 | −1.970 | 44.383 | 9.300 | 1.00 | 29.23 | 8 |
| ATOM | 646 | N | LEU | A | 197 | −0.448 | 43.765 | 10.821 | 1.00 | 26.41 | 7 |
| ATOM | 647 | CA | LEU | A | 197 | 0.329 | 44.989 | 10.638 | 1.00 | 24.54 | 6 |
| ATOM | 648 | CB | LEU | A | 197 | 1.464 | 45.064 | 11.623 | 1.00 | 22.89 | 6 |
| ATOM | 649 | CG | LEU | A | 197 | 2.400 | 46.254 | 11.546 | 1.00 | 24.59 | 6 |
| ATOM | 650 | CD1 | LEU | A | 197 | 1.789 | 47.610 | 11.857 | 1.00 | 28.10 | 6 |
| ATOM | 651 | CD2 | LEU | A | 197 | 3.592 | 45.960 | 12.455 | 1.00 | 27.91 | 6 |
| ATOM | 652 | C | LEU | A | 197 | 0.858 | 45.132 | 9.195 | 1.00 | 22.96 | 6 |
| ATOM | 653 | O | LEU | A | 197 | 0.744 | 46.208 | 8.599 | 1.00 | 25.34 | 8 |
| ATOM | 654 | N | PHE | A | 198 | 1.456 | 44.113 | 8.670 | 1.00 | 22.19 | 7 |
| ATOM | 655 | CA | PHE | A | 198 | 2.074 | 44.173 | 7.320 | 1.00 | 26.14 | 6 |
| ATOM | 656 | CB | PHE | A | 198 | 3.191 | 43.158 | 7.237 | 1.00 | 25.23 | 6 |
| ATOM | 657 | CG | PHE | A | 198 | 4.401 | 43.555 | 8.043 | 1.00 | 24.37 | 6 |
| ATOM | 658 | CD1 | PHE | A | 198 | 4.583 | 43.021 | 9.311 | 1.00 | 27.98 | 6 |
| ATOM | 659 | CD2 | PHE | A | 198 | 5.290 | 44.493 | 7.600 | 1.00 | 26.06 | 6 |
| ATOM | 660 | CE1 | PHE | A | 198 | 5.669 | 43.416 | 10.068 | 1.00 | 26.50 | 6 |
| ATOM | 661 | CE2 | PHE | A | 198 | 6.376 | 44.898 | 8.324 | 1.00 | 26.50 | 6 |
| ATOM | 662 | CZ | PHE | A | 198 | 6.583 | 44.349 | 9.584 | 1.00 | 24.03 | 6 |
| ATOM | 663 | C | PHE | A | 198 | 1.063 | 44.075 | 6.215 | 1.00 | 27.88 | 6 |
| ATOM | 664 | O | PHE | A | 198 | 1.389 | 44.527 | 5.119 | 1.00 | 29.23 | 8 |
| ATOM | 665 | N | SER | A | 199 | −0.163 | 43.662 | 6.554 | 1.00 | 30.11 | 7 |
| ATOM | 666 | CA | SER | A | 199 | −1.196 | 43.609 | 5.519 | 1.00 | 32.39 | 6 |
| ATOM | 667 | CB | SER | A | 199 | −1.975 | 42.287 | 5.669 | 1.00 | 34.42 | 6 |
| ATOM | 668 | OG | SER | A | 199 | −2.802 | 42.466 | 6.800 | 1.00 | 43.38 | 8 |
| ATOM | 669 | C | SER | A | 199 | −2.129 | 44.790 | 5.572 | 1.00 | 32.01 | 6 |
| ATOM | 670 | O | SER | A | 199 | −3.108 | 44.873 | 4.809 | 1.00 | 36.63 | 8 |
| ATOM | 671 | N | GLY | A | 200 | −1.936 | 45.715 | 6.497 | 1.00 | 26.46 | 7 |
| ATOM | 672 | CA | GLY | A | 200 | −2.719 | 46.913 | 6.622 | 1.00 | 30.24 | 6 |
| ATOM | 673 | C | GLY | A | 200 | −4.089 | 46.697 | 7.221 | 1.00 | 37.40 | 6 |
| ATOM | 674 | O | GLY | A | 200 | −5.045 | 47.396 | 6.885 | 1.00 | 42.48 | 8 |
| ATOM | 675 | N | LYS | A | 201 | −4.195 | 45.797 | 8.186 | 1.00 | 35.07 | 7 |
| ATOM | 676 | CA | LYS | A | 201 | −5.466 | 45.583 | 8.887 | 1.00 | 39.63 | 6 |
| ATOM | 677 | CB | LYS | A | 201 | −5.761 | 44.094 | 9.088 | 1.00 | 41.19 | 6 |
| ATOM | 678 | CG | LYS | A | 201 | −5.538 | 43.369 | 7.769 | 1.00 | 43.81 | 6 |
| ATOM | 679 | CD | LYS | A | 201 | −6.418 | 42.142 | 7.586 | 1.00 | 52.66 | 6 |
| ATOM | 680 | CE | LYS | A | 201 | −6.541 | 41.945 | 6.069 | 1.00 | 53.36 | 6 |
| ATOM | 681 | NZ | LYS | A | 201 | −6.396 | 43.284 | 5.415 | 1.00 | 53.44 | 7 |
| ATOM | 682 | C | LYS | A | 201 | −5.373 | 46.308 | 10.219 | 1.00 | 44.11 | 6 |
| ATOM | 683 | O | LYS | A | 201 | −5.967 | 47.376 | 10.421 | 1.00 | 48.21 | 8 |
| ATOM | 684 | N | HIS | A | 202 | −4.645 | 45.700 | 11.127 | 1.00 | 41.73 | 7 |
| ATOM | 685 | CA | HIS | A | 202 | −4.429 | 46.288 | 12.448 | 1.00 | 47.06 | 6 |
| ATOM | 686 | C | HIS | A | 202 | −4.966 | 47.699 | 12.541 | 1.00 | 50.86 | 6 |
| ATOM | 687 | O | HIS | A | 202 | −6.043 | 47.930 | 13.140 | 1.00 | 51.62 | 8 |
| ATOM | 688 | CB | HIS | A | 202 | −2.892 | 46.295 | 12.678 | 1.00 | 39.32 | 6 |
| ATOM | 689 | CG | HIS | A | 202 | −2.571 | 45.523 | 13.918 | 1.00 | 54.43 | 6 |

-continued

PDB FILE LISTING –cd81el.pdb

| | | | | | | | | | | |
|---|---|---|---|---|---|---|---|---|---|---|
| ATOM | 690 | ND1 | HIS | A | 202 | −3.177 | 45.808 | 15.124 | 1.00 | 60.36 | 7 |
| ATOM | 691 | CD2 | HIS | A | 202 | −1.740 | 44.481 | 14.121 | 1.00 | 32.15 | 6 |
| ATOM | 692 | CE1 | HIS | A | 202 | −2.714 | 44.975 | 16.050 | 1.00 | 58.04 | 6 |
| ATOM | 693 | NE2 | HIS | A | 202 | −1.847 | 44.161 | 15.461 | 1.00 | 66.87 | 7 |
| ATOM | 694 | CB | PHE | B | 213 | 19.717 | 35.136 | 16.091 | 0.00 | 34.83 | 6 |
| ATOM | 695 | CG | PHE | B | 213 | 20.197 | 34.465 | 17.321 | 0.00 | 44.80 | 6 |
| ATOM | 696 | CD1 | PHE | B | 213 | 21.533 | 34.182 | 17.521 | 0.00 | 58.13 | 6 |
| ATOM | 697 | CD2 | PHE | B | 213 | 19.319 | 34.146 | 18.350 | 0.00 | 62.44 | 6 |
| ATOM | 698 | CE1 | PHE | B | 213 | 21.983 | 33.580 | 18.677 | 0.00 | 56.87 | 6 |
| ATOM | 699 | CE2 | PHE | B | 213 | 19.751 | 33.535 | 19.518 | 0.00 | 69.83 | 6 |
| ATOM | 700 | CZ | PHE | B | 213 | 21.091 | 33.243 | 19.683 | 0.00 | 53.63 | 6 |
| ATOM | 701 | C | PHE | B | 213 | 18.658 | 35.823 | 13.931 | 1.00 | 38.28 | 6 |
| ATOM | 702 | O | PHE | B | 213 | 19.511 | 36.353 | 13.199 | 1.00 | 40.98 | 8 |
| ATOM | 703 | N | PHE | B | 213 | 20.058 | 33.920 | 13.960 | 0.00 | 39.06 | 7 |
| ATOM | 704 | CA | PHE | B | 213 | 18.949 | 34.523 | 14.688 | 1.00 | 37.25 | 6 |
| ATOM | 705 | N | VAL | B | 214 | 17.444 | 36.311 | 14.059 | 1.00 | 28.83 | 7 |
| ATOM | 706 | CA | VAL | B | 214 | 17.111 | 37.604 | 13.427 | 1.00 | 27.89 | 6 |
| ATOM | 707 | CB | VAL | B | 214 | 15.585 | 37.806 | 13.482 | 1.00 | 22.89 | 6 |
| ATOM | 708 | CG1 | VAL | B | 214 | 15.193 | 39.183 | 12.890 | 1.00 | 26.71 | 6 |
| ATOM | 709 | CG2 | VAL | B | 214 | 14.947 | 36.736 | 12.598 | 1.00 | 28.90 | 6 |
| ATOM | 710 | C | VAL | B | 214 | 17.745 | 38.665 | 14.270 | 1.00 | 28.77 | 6 |
| ATOM | 711 | O | VAL | B | 214 | 17.533 | 38.794 | 15.474 | 1.00 | 28.76 | 8 |
| ATOM | 712 | N | ASN | B | 215 | 18.444 | 39.614 | 13.620 | 1.00 | 29.41 | 7 |
| ATOM | 713 | CA | ASN | B | 215 | 19.127 | 40.646 | 14.396 | 1.00 | 28.39 | 6 |
| ATOM | 714 | CB | ASN | B | 215 | 20.442 | 40.928 | 13.643 | 1.00 | 32.91 | 6 |
| ATOM | 715 | CG | ASN | B | 215 | 21.148 | 42.093 | 14.265 | 1.00 | 39.44 | 6 |
| ATOM | 716 | OD1 | ASN | B | 215 | 21.865 | 41.881 | 15.245 | 1.00 | 53.33 | 8 |
| ATOM | 717 | ND2 | ASN | B | 215 | 20.905 | 43.288 | 13.757 | 1.00 | 37.32 | 7 |
| ATOM | 718 | C | ASN | B | 215 | 18.259 | 41.895 | 14.501 | 1.00 | 27.27 | 6 |
| ATOM | 719 | O | ASN | B | 215 | 17.705 | 42.313 | 13.486 | 1.00 | 27.80 | 8 |
| ATOM | 720 | N | LYS | B | 216 | 18.223 | 42.525 | 15.657 | 1.00 | 29.93 | 7 |
| ATOM | 721 | CA | LYS | B | 216 | 17.420 | 43.699 | 15.889 | 1.00 | 30.04 | 6 |
| ATOM | 722 | CB | LYS | B | 216 | 17.601 | 44.227 | 17.320 | 1.00 | 38.33 | 6 |
| ATOM | 723 | CG | LYS | B | 216 | 17.259 | 45.678 | 17.506 | 1.00 | 51.27 | 6 |
| ATOM | 724 | CD | LYS | B | 216 | 18.220 | 46.399 | 18.436 | 1.00 | 60.50 | 6 |
| ATOM | 725 | CE | LYS | B | 216 | 17.949 | 47.901 | 18.401 | 1.00 | 41.22 | 6 |
| ATOM | 726 | NZ | LYS | B | 216 | 18.269 | 48.521 | 19.723 | 1.00 | 56.24 | 7 |
| ATOM | 727 | C | LYS | B | 216 | 17.571 | 44.843 | 14.896 | 1.00 | 32.97 | 6 |
| ATOM | 728 | O | LYS | B | 216 | 16.642 | 45.376 | 14.285 | 1.00 | 32.82 | 8 |
| ATOM | 729 | N | ASP | B | 217 | 18.815 | 45.234 | 14.662 | 1.00 | 30.39 | 7 |
| ATOM | 730 | CA | ASP | B | 217 | 19.079 | 46.384 | 13.755 | 1.00 | 28.18 | 6 |
| ATOM | 731 | CB | ASP | B | 217 | 20.615 | 46.597 | 13.856 | 1.00 | 37.07 | 6 |
| ATOM | 732 | CG | ASP | B | 217 | 20.974 | 47.025 | 15.271 | 1.00 | 50.77 | 6 |
| ATOM | 733 | OD1 | ASP | B | 217 | 20.325 | 47.961 | 15.789 | 1.00 | 50.99 | 8 |
| ATOM | 734 | OD2 | ASP | B | 217 | 21.873 | 46.381 | 15.855 | 1.00 | 48.20 | 8 |
| ATOM | 735 | C | ASP | B | 217 | 18.710 | 46.045 | 12.326 | 1.00 | 27.65 | 6 |
| ATOM | 736 | O | ASP | B | 217 | 18.209 | 46.917 | 11.586 | 1.00 | 29.68 | 8 |
| ATOM | 737 | N | GLN | B | 218 | 18.945 | 44.818 | 11.903 | 1.00 | 26.96 | 7 |
| ATOM | 738 | CA | GLN | B | 218 | 18.641 | 44.363 | 10.567 | 1.00 | 26.89 | 6 |
| ATOM | 739 | CB | GLN | B | 218 | 19.194 | 43.015 | 10.137 | 1.00 | 28.58 | 6 |
| ATOM | 740 | CG | GLN | B | 218 | 18.876 | 42.625 | 8.703 | 1.00 | 28.47 | 6 |
| ATOM | 741 | CD | GLN | B | 218 | 19.550 | 43.604 | 7.748 | 1.00 | 39.80 | 6 |
| ATOM | 742 | OE1 | GLN | B | 218 | 20.732 | 43.897 | 7.957 | 1.00 | 49.83 | 8 |
| ATOM | 743 | NE2 | GLN | B | 218 | 18.880 | 44.111 | 6.730 | 1.00 | 37.47 | 7 |
| ATOM | 744 | C | GLN | B | 218 | 17.118 | 44.408 | 10.342 | 1.00 | 26.99 | 6 |
| ATOM | 745 | O | GLN | B | 218 | 16.688 | 44.970 | 9.349 | 1.00 | 23.66 | 8 |
| ATOM | 746 | N | ILE | B | 219 | 16.361 | 43.806 | 11.268 | 1.00 | 22.98 | 7 |
| ATOM | 747 | CA | ILE | B | 219 | 14.909 | 43.777 | 11.054 | 1.00 | 22.46 | 6 |
| ATOM | 748 | CB | ILE | B | 219 | 14.209 | 42.791 | 11.998 | 1.00 | 24.01 | 6 |
| ATOM | 749 | CG2 | ILE | B | 219 | 14.320 | 43.076 | 13.484 | 1.00 | 23.36 | 6 |
| ATOM | 750 | CG1 | ILE | B | 219 | 12.723 | 42.606 | 11.625 | 1.00 | 27.82 | 6 |
| ATOM | 751 | CD1 | ILE | B | 219 | 12.575 | 42.170 | 10.187 | 1.00 | 28.39 | 6 |
| ATOM | 752 | C | ILE | B | 219 | 14.345 | 45.182 | 11.118 | 1.00 | 23.15 | 6 |
| ATOM | 753 | O | ILE | B | 219 | 13.418 | 45.528 | 10.374 | 1.00 | 24.69 | 8 |
| ATOM | 754 | N | ALA | B | 220 | 14.870 | 46.029 | 11.972 | 1.00 | 21.24 | 7 |
| ATOM | 755 | CA | ALA | B | 220 | 14.395 | 47.403 | 12.053 | 1.00 | 23.02 | 6 |
| ATOM | 756 | CB | ALA | B | 220 | 14.940 | 48.146 | 13.226 | 1.00 | 28.82 | 6 |
| ATOM | 757 | C | ALA | B | 220 | 14.573 | 48.131 | 10.730 | 1.00 | 23.96 | 6 |
| ATOM | 758 | O | ALA | B | 220 | 13.704 | 48.838 | 10.261 | 1.00 | 23.87 | 8 |
| ATOM | 759 | N | LYS | B | 221 | 15.767 | 47.916 | 10.161 | 1.00 | 25.79 | 7 |
| ATOM | 760 | CA | LYS | B | 221 | 16.086 | 48.555 | 8.865 | 1.00 | 26.23 | 6 |
| ATOM | 761 | CB | LYS | B | 221 | 17.518 | 48.106 | 8.505 | 1.00 | 23.73 | 6 |
| ATOM | 762 | CG | LYS | B | 221 | 17.859 | 48.602 | 7.084 | 1.00 | 32.18 | 6 |
| ATOM | 763 | CD | LYS | B | 221 | 19.349 | 48.458 | 6.835 | 1.00 | 48.70 | 6 |
| ATOM | 764 | CE | LYS | B | 221 | 19.738 | 48.828 | 5.402 | 1.00 | 49.31 | 6 |
| ATOM | 765 | NZ | LYS | B | 221 | 18.639 | 48.516 | 4.446 | 1.00 | 60.95 | 7 |
| ATOM | 766 | C | LYS | B | 221 | 15.111 | 48.086 | 7.783 | 1.00 | 26.25 | 6 |

-continued

PDB FILE LISTING –cd81lel.pdb

| ATOM | 767 | O | LYS | B | 221 | 14.595 | 48.870 | 6.961 | 1.00 | 24.99 | 8 |
|------|-----|------|-----|---|-----|--------|--------|--------|------|-------|---|
| ATOM | 768 | N | ASP | B | 222 | 14.904 | 46.759 | 7.727 | 1.00 | 24.13 | 7 |
| ATOM | 769 | CA | ASP | B | 222 | 13.988 | 46.167 | 6.775 | 1.00 | 23.28 | 6 |
| ATOM | 770 | CB | ASP | B | 222 | 13.982 | 44.670 | 6.968 | 1.00 | 26.58 | 6 |
| ATOM | 771 | CG | ASP | B | 222 | 15.288 | 43.945 | 6.671 | 1.00 | 37.75 | 6 |
| ATOM | 772 | OD1 | ASP | B | 222 | 16.177 | 44.545 | 6.002 | 1.00 | 35.10 | 8 |
| ATOM | 773 | OD2 | ASP | B | 222 | 15.441 | 42.777 | 7.110 | 1.00 | 31.39 | 8 |
| ATOM | 774 | C | ASP | B | 222 | 12.586 | 46.747 | 6.890 | 1.00 | 24.42 | 6 |
| ATOM | 775 | O | ASP | B | 222 | 11.842 | 46.970 | 5.918 | 1.00 | 25.24 | 8 |
| ATOM | 776 | N | VAL | B | 223 | 12.130 | 46.917 | 8.182 | 1.00 | 22.06 | 7 |
| ATOM | 777 | CA | VAL | B | 223 | 10.773 | 47.427 | 8.389 | 1.00 | 20.51 | 6 |
| ATOM | 778 | CB | VAL | B | 223 | 10.346 | 47.208 | 9.897 | 1.00 | 19.83 | 6 |
| ATOM | 779 | CG1 | VAL | B | 223 | 8.934 | 47.819 | 10.090 | 1.00 | 20.77 | 6 |
| ATOM | 780 | CG2 | VAL | B | 223 | 10.265 | 45.693 | 10.021 | 1.00 | 22.25 | 6 |
| ATOM | 781 | C | VAL | B | 223 | 10.653 | 48.898 | 8.031 | 1.00 | 21.93 | 6 |
| ATOM | 782 | O | VAL | B | 223 | 9.636 | 49.304 | 7.482 | 1.00 | 23.92 | 8 |
| ATOM | 783 | N | LYS | B | 224 | 11.687 | 49.704 | 8.307 | 1.00 | 24.30 | 7 |
| ATOM | 784 | CA | LYS | B | 224 | 11.651 | 51.102 | 7.873 | 1.00 | 22.31 | 6 |
| ATOM | 785 | CB | LYS | B | 224 | 12.864 | 51.841 | 8.430 | 1.00 | 23.89 | 6 |
| ATOM | 786 | CG | LYS | B | 224 | 12.817 | 51.931 | 9.959 | 1.00 | 26.32 | 6 |
| ATOM | 787 | CD | LYS | B | 224 | 14.034 | 52.827 | 10.307 | 1.00 | 30.62 | 6 |
| ATOM | 788 | CE | LYS | B | 224 | 14.495 | 52.556 | 11.713 | 1.00 | 36.62 | 6 |
| ATOM | 789 | NZ | LYS | B | 224 | 15.946 | 52.883 | 11.937 | 1.00 | 36.97 | 7 |
| ATOM | 790 | C | LYS | B | 224 | 11.724 | 51.116 | 6.341 | 1.00 | 22.74 | 6 |
| ATOM | 791 | O | LYS | B | 224 | 11.013 | 51.991 | 5.787 | 1.00 | 24.89 | 8 |
| ATOM | 792 | N | GLN | B | 225 | 12.380 | 50.174 | 5.720 | 1.00 | 23.32 | 7 |
| ATOM | 793 | CA | GLN | B | 225 | 12.371 | 50.203 | 4.236 | 1.00 | 25.62 | 6 |
| ATOM | 794 | CB | GLN | B | 225 | 13.406 | 49.210 | 3.710 | 1.00 | 32.12 | 6 |
| ATOM | 795 | CG | GLN | B | 225 | 13.606 | 49.177 | 2.203 | 1.00 | 38.34 | 6 |
| ATOM | 796 | CD | GLN | B | 225 | 14.606 | 48.107 | 1.788 | 1.00 | 49.03 | 6 |
| ATOM | 797 | OE1 | GLN | B | 225 | 14.901 | 47.117 | 2.477 | 1.00 | 39.12 | 8 |
| ATOM | 798 | NE2 | GLN | B | 225 | 15.160 | 48.322 | 0.591 | 1.00 | 50.68 | 7 |
| ATOM | 799 | C | GLN | B | 225 | 11.015 | 49.920 | 3.658 | 1.00 | 26.59 | 6 |
| ATOM | 800 | O | GLN | B | 225 | 10.508 | 50.492 | 2.680 | 1.00 | 27.36 | 8 |
| ATOM | 801 | N | PHE | B | 226 | 10.302 | 48.952 | 4.258 | 1.00 | 25.80 | 7 |
| ATOM | 802 | CA | PHE | B | 226 | 8.971 | 48.534 | 3.933 | 1.00 | 20.22 | 6 |
| ATOM | 803 | CB | PHE | B | 226 | 8.522 | 47.339 | 4.808 | 1.00 | 24.02 | 6 |
| ATOM | 804 | CG | PHE | B | 226 | 7.074 | 47.012 | 4.701 | 1.00 | 23.15 | 6 |
| ATOM | 805 | CD1 | PHE | B | 226 | 6.628 | 46.093 | 3.758 | 1.00 | 31.92 | 6 |
| ATOM | 806 | CD2 | PHE | B | 226 | 6.116 | 47.603 | 5.521 | 1.00 | 24.40 | 6 |
| ATOM | 807 | CE1 | PHE | B | 226 | 5.300 | 45.763 | 3.633 | 1.00 | 31.15 | 6 |
| ATOM | 808 | CE2 | PHE | B | 226 | 4.777 | 47.282 | 5.405 | 1.00 | 27.17 | 6 |
| ATOM | 809 | CZ | PHE | B | 226 | 4.258 | 46.347 | 4.480 | 1.00 | 30.58 | 6 |
| ATOM | 810 | C | PHE | B | 226 | 8.048 | 49.722 | 4.129 | 1.00 | 25.25 | 6 |
| ATOM | 811 | O | PHE | B | 226 | 7.144 | 49.992 | 3.322 | 1.00 | 24.87 | 8 |
| ATOM | 812 | N | TYR | B | 227 | 8.134 | 50.368 | 5.323 | 1.00 | 23.99 | 7 |
| ATOM | 813 | CA | TYR | B | 227 | 7.292 | 51.560 | 5.541 | 1.00 | 22.94 | 6 |
| ATOM | 814 | CB | TYR | B | 227 | 7.513 | 52.055 | 6.995 | 1.00 | 24.23 | 6 |
| ATOM | 815 | CG | TYR | B | 227 | 6.875 | 53.415 | 7.212 | 1.00 | 23.07 | 6 |
| ATOM | 816 | CD1 | TYR | B | 227 | 5.501 | 53.551 | 7.469 | 1.00 | 22.96 | 6 |
| ATOM | 817 | CE1 | TYR | B | 227 | 4.873 | 54.758 | 7.629 | 1.00 | 22.01 | 6 |
| ATOM | 818 | CD2 | TYR | B | 227 | 7.591 | 54.580 | 7.177 | 1.00 | 23.12 | 6 |
| ATOM | 819 | CE2 | TYR | B | 227 | 6.985 | 55.813 | 7.341 | 1.00 | 26.09 | 6 |
| ATOM | 820 | CZ | TYR | B | 227 | 5.634 | 55.910 | 7.543 | 1.00 | 23.78 | 6 |
| ATOM | 821 | OH | TYR | B | 227 | 5.113 | 57.191 | 7.727 | 1.00 | 28.18 | 8 |
| ATOM | 822 | C | TYR | B | 227 | 7.513 | 52.644 | 4.489 | 1.00 | 21.85 | 6 |
| ATOM | 823 | O | TYR | B | 227 | 6.545 | 53.199 | 3.930 | 1.00 | 27.43 | 8 |
| ATOM | 824 | N | ASP | B | 228 | 8.769 | 52.943 | 4.220 | 1.00 | 23.83 | 7 |
| ATOM | 825 | CA | ASP | B | 228 | 9.117 | 53.991 | 3.230 | 1.00 | 25.77 | 6 |
| ATOM | 826 | CB | ASP | B | 228 | 10.610 | 54.172 | 3.106 | 1.00 | 26.19 | 6 |
| ATOM | 827 | CG | ASP | B | 228 | 11.279 | 54.729 | 4.348 | 1.00 | 27.12 | 6 |
| ATOM | 828 | OD1 | ASP | B | 228 | 10.518 | 55.146 | 5.256 | 1.00 | 28.17 | 8 |
| ATOM | 829 | OD2 | ASP | B | 228 | 12.537 | 54.751 | 4.378 | 1.00 | 31.94 | 8 |
| ATOM | 830 | C | ASP | B | 228 | 8.519 | 53.695 | 1.862 | 1.00 | 25.92 | 6 |
| ATOM | 831 | O | ASP | B | 228 | 7.956 | 54.619 | 1.257 | 1.00 | 28.03 | 8 |
| ATOM | 832 | N | GLN | B | 229 | 8.540 | 52.452 | 1.469 | 1.00 | 27.73 | 7 |
| ATOM | 833 | CA | GLN | B | 229 | 7.956 | 52.045 | 0.199 | 1.00 | 31.06 | 6 |
| ATOM | 834 | CB | GLN | B | 229 | 8.436 | 50.632 | −0.154 | 1.00 | 32.10 | 6 |
| ATOM | 835 | CG | GLN | B | 229 | 7.569 | 50.055 | −1.271 | 1.00 | 40.19 | 6 |
| ATOM | 836 | CD | GLN | B | 229 | 8.063 | 48.701 | −1.765 | 1.00 | 35.54 | 6 |
| ATOM | 837 | OE1 | GLN | B | 229 | 7.397 | 47.704 | −1.552 | 1.00 | 55.35 | 8 |
| ATOM | 838 | NE2 | GLN | B | 229 | 9.228 | 48.759 | −2.400 | 1.00 | 49.50 | 7 |
| ATOM | 839 | C | GLN | B | 229 | 6.462 | 52.183 | 0.174 | 1.00 | 29.95 | 6 |
| ATOM | 840 | O | GLN | B | 229 | 5.849 | 52.694 | −0.755 | 1.00 | 30.54 | 8 |
| ATOM | 841 | N | ALA | B | 230 | 5.752 | 51.857 | 1.285 | 1.00 | 28.41 | 7 |
| ATOM | 842 | CA | ALA | B | 230 | 4.294 | 52.032 | 1.330 | 1.00 | 24.57 | 6 |
| ATOM | 843 | CB | ALA | B | 230 | 3.798 | 51.420 | 2.650 | 1.00 | 29.26 | 6 |

-continued

PDB FILE LISTING –cd81el.pdb

| ATOM | 844 | C | ALA | B | 230 | 3.929 | 53.503 | 1.291 | 1.00 | 27.29 | 6 |
|------|-----|-----|-----|---|-----|--------|--------|--------|------|-------|---|
| ATOM | 845 | O | ALA | B | 230 | 2.899 | 53.939 | 0.741 | 1.00 | 30.79 | 8 |
| ATOM | 846 | N | LEU | B | 231 | 4.736 | 54.350 | 1.937 | 1.00 | 24.06 | 7 |
| ATOM | 847 | CA | LEU | B | 231 | 4.454 | 55.788 | 1.977 | 1.00 | 26.67 | 6 |
| ATOM | 848 | CB | LEU | B | 231 | 5.489 | 56.473 | 2.816 | 1.00 | 33.38 | 6 |
| ATOM | 849 | CG | LEU | B | 231 | 5.296 | 57.803 | 3.506 | 1.00 | 35.20 | 6 |
| ATOM | 850 | CD1 | LEU | B | 231 | 4.007 | 57.825 | 4.338 | 1.00 | 36.95 | 6 |
| ATOM | 851 | CD2 | LEU | B | 231 | 6.470 | 57.979 | 4.478 | 1.00 | 30.01 | 6 |
| ATOM | 852 | C | LEU | B | 231 | 4.544 | 56.325 | 0.526 | 1.00 | 28.69 | 6 |
| ATOM | 853 | O | LEU | B | 231 | 3.664 | 57.109 | 0.174 | 1.00 | 32.37 | 8 |
| ATOM | 854 | N | GLN | B | 232 | 5.594 | 55.890 | −0.151 | 1.00 | 28.25 | 7 |
| ATOM | 855 | CA | GLN | B | 232 | 5.788 | 56.301 | −1.539 | 1.00 | 26.43 | 6 |
| ATOM | 856 | CB | GLN | B | 232 | 7.123 | 55.916 | −2.154 | 1.00 | 27.83 | 6 |
| ATOM | 857 | CG | GLN | B | 232 | 7.104 | 56.319 | −3.651 | 1.00 | 40.21 | 6 |
| ATOM | 858 | CD | GLN | B | 232 | 7.235 | 57.824 | −3.813 | 1.00 | 44.86 | 6 |
| ATOM | 859 | OE1 | GLN | B | 232 | 8.250 | 58.422 | −3.452 | 1.00 | 47.98 | 8 |
| ATOM | 860 | NE2 | GLN | B | 232 | 6.207 | 58.469 | −4.365 | 1.00 | 59.78 | 7 |
| ATOM | 861 | C | GLN | B | 232 | 4.602 | 55.793 | −2.328 | 1.00 | 32.25 | 6 |
| ATOM | 862 | O | GLN | B | 232 | 3.988 | 56.547 | −3.078 | 1.00 | 34.60 | 8 |
| ATOM | 863 | N | GLN | B | 233 | 4.268 | 54.515 | −2.235 | 1.00 | 30.14 | 7 |
| ATOM | 864 | CA | GLN | B | 233 | 3.120 | 53.953 | −2.896 | 1.00 | 31.57 | 6 |
| ATOM | 865 | CB | GLN | B | 233 | 3.050 | 52.432 | −2.787 | 1.00 | 36.28 | 6 |
| ATOM | 866 | CG | GLN | B | 233 | 4.251 | 51.705 | −3.354 | 1.00 | 48.59 | 6 |
| ATOM | 867 | CD | GLN | B | 233 | 4.203 | 50.201 | −3.105 | 1.00 | 57.17 | 6 |
| ATOM | 868 | OE1 | GLN | B | 233 | 3.292 | 49.661 | −2.475 | 1.00 | 55.45 | 8 |
| ATOM | 869 | NE2 | GLN | B | 233 | 5.212 | 49.490 | −3.609 | 1.00 | 52.72 | 7 |
| ATOM | 870 | C | GLN | B | 233 | 1.795 | 54.588 | −2.597 | 1.00 | 36.59 | 6 |
| ATOM | 871 | O | GLN | B | 233 | 0.978 | 54.775 | −3.490 | 1.00 | 33.24 | 8 |
| ATOM | 872 | N | ALA | B | 234 | 1.500 | 54.941 | −1.342 | 1.00 | 34.08 | 7 |
| ATOM | 873 | CA | ALA | B | 234 | 0.236 | 55.543 | −0.953 | 1.00 | 31.39 | 6 |
| ATOM | 874 | CB | ALA | B | 234 | 0.233 | 55.805 | 0.554 | 1.00 | 38.61 | 6 |
| ATOM | 875 | C | ALA | B | 234 | −0.023 | 56.910 | −1.579 | 1.00 | 37.11 | 6 |
| ATOM | 876 | O | ALA | B | 234 | −1.162 | 57.369 | −1.539 | 1.00 | 40.52 | 8 |
| ATOM | 877 | N | VAL | B | 235 | 1.020 | 57.582 | −1.993 | 1.00 | 35.31 | 7 |
| ATOM | 878 | CA | VAL | B | 235 | 0.886 | 58.936 | −2.523 | 1.00 | 45.20 | 6 |
| ATOM | 879 | CB | VAL | B | 235 | 2.237 | 59.674 | −2.510 | 1.00 | 45.97 | 6 |
| ATOM | 880 | CG1 | VAL | B | 235 | 2.240 | 60.797 | −3.520 | 1.00 | 57.51 | 6 |
| ATOM | 881 | CG2 | VAL | B | 235 | 2.552 | 60.112 | −1.095 | 1.00 | 52.58 | 6 |
| ATOM | 882 | C | VAL | B | 235 | 0.303 | 58.949 | −3.917 | 1.00 | 47.01 | 6 |
| ATOM | 883 | O | VAL | B | 235 | −0.462 | 59.839 | −4.250 | 1.00 | 44.05 | 8 |
| ATOM | 884 | N | VAL | B | 236 | 0.545 | 57.898 | −4.675 | 1.00 | 53.53 | 7 |
| ATOM | 885 | CA | VAL | B | 236 | 0.086 | 57.778 | −6.044 | 1.00 | 60.39 | 6 |
| ATOM | 886 | CB | VAL | B | 236 | 1.147 | 57.008 | −6.861 | 1.00 | 61.99 | 6 |
| ATOM | 887 | CG1 | VAL | B | 236 | 2.528 | 57.201 | −6.254 | 1.00 | 60.20 | 6 |
| ATOM | 888 | CG2 | VAL | B | 236 | 0.778 | 55.535 | −6.904 | 1.00 | 55.70 | 6 |
| ATOM | 889 | C | VAL | B | 236 | −1.253 | 57.088 | −6.212 | 1.00 | 62.78 | 6 |
| ATOM | 890 | O | VAL | B | 236 | −1.887 | 56.597 | −5.282 | 1.00 | 63.95 | 8 |
| ATOM | 891 | N | ASP | B | 237 | −1.720 | 57.051 | −7.456 | 1.00 | 65.68 | 7 |
| ATOM | 892 | CA | ASP | B | 237 | −2.972 | 56.428 | −7.831 | 1.00 | 67.82 | 6 |
| ATOM | 893 | CB | ASP | B | 237 | −2.741 | 54.984 | −8.278 | 1.00 | 72.56 | 6 |
| ATOM | 894 | CG | ASP | B | 237 | −2.597 | 54.853 | −9.782 | 1.00 | 75.01 | 6 |
| ATOM | 895 | OD1 | ASP | B | 237 | −2.837 | 55.847 | −10.500 | 1.00 | 71.57 | 8 |
| ATOM | 896 | OD2 | ASP | B | 237 | −2.249 | 53.743 | −10.241 | 1.00 | 73.99 | 8 |
| ATOM | 897 | C | ASP | B | 237 | −4.041 | 56.492 | −6.756 | 1.00 | 67.93 | 6 |
| ATOM | 898 | O | ASP | B | 237 | −3.990 | 57.440 | −5.938 | 1.00 | 69.24 | 8 |
| ATOM | 899 | CB | ASN | C | 242 | −2.832 | 47.036 | −0.049 | 1.00 | 52.44 | 6 |
| ATOM | 900 | CG | ASN | C | 242 | −3.531 | 46.708 | 1.256 | 1.00 | 53.59 | 6 |
| ATOM | 901 | OD1 | ASN | C | 242 | −4.754 | 46.644 | 1.309 | 1.00 | 68.85 | 8 |
| ATOM | 902 | ND2 | ASN | C | 242 | −2.755 | 46.521 | 2.306 | 1.00 | 62.22 | 7 |
| ATOM | 903 | C | ASN | C | 242 | −2.213 | 49.417 | 0.387 | 1.00 | 39.79 | 6 |
| ATOM | 904 | O | ASN | C | 242 | −2.332 | 49.370 | 1.630 | 1.00 | 39.72 | 8 |
| ATOM | 905 | N | ASN | C | 242 | −3.171 | 48.676 | −1.871 | 1.00 | 39.76 | 7 |
| ATOM | 906 | CA | ASN | C | 242 | −3.103 | 48.497 | −0.415 | 1.00 | 43.08 | 6 |
| ATOM | 907 | N | ALA | C | 243 | −1.401 | 50.254 | −0.254 | 1.00 | 36.60 | 7 |
| ATOM | 908 | CA | ALA | C | 243 | −0.491 | 51.133 | 0.430 | 1.00 | 34.21 | 6 |
| ATOM | 909 | CB | ALA | C | 243 | 0.480 | 51.825 | −0.534 | 1.00 | 32.11 | 6 |
| ATOM | 910 | C | ALA | C | 243 | −1.151 | 52.133 | 1.366 | 1.00 | 36.65 | 6 |
| ATOM | 911 | O | ALA | C | 243 | −0.621 | 52.349 | 2.471 | 1.00 | 33.63 | 8 |
| ATOM | 912 | N | LYS | C | 244 | −2.309 | 52.694 | 0.990 | 1.00 | 31.22 | 7 |
| ATOM | 913 | CA | LYS | C | 244 | −2.931 | 53.638 | 1.903 | 1.00 | 35.12 | 6 |
| ATOM | 914 | CB | LYS | C | 244 | −4.102 | 54.402 | 1.304 | 1.00 | 38.30 | 6 |
| ATOM | 915 | CG | LYS | C | 244 | −3.677 | 55.244 | 0.096 | 1.00 | 47.69 | 6 |
| ATOM | 916 | CD | LYS | C | 244 | −4.704 | 56.314 | −0.233 | 1.00 | 59.26 | 6 |
| ATOM | 917 | CE | LYS | C | 244 | −4.248 | 57.259 | −1.342 | 1.00 | 45.56 | 6 |
| ATOM | 918 | NZ | LYS | C | 244 | −3.736 | 56.493 | −2.515 | 1.00 | 48.06 | 7 |
| ATOM | 919 | C | LYS | C | 244 | −3.251 | 52.942 | 3.219 | 1.00 | 31.26 | 6 |
| ATOM | 920 | O | LYS | C | 244 | −3.045 | 53.522 | 4.294 | 1.00 | 37.97 | 8 |

-continued

PDB FILE LISTING –cd81el.pdb

| | | | | | | | | | | |
|---|---|---|---|---|---|---|---|---|---|---|
| ATOM | 921 | N | ALA | C | 245 | −3.851 | 51.759 | 3.155 | 1.00 | 35.96 | 7 |
| ATOM | 922 | CA | ALA | C | 245 | −4.202 | 51.044 | 4.371 | 1.00 | 35.05 | 6 |
| ATOM | 923 | CB | ALA | C | 245 | −5.204 | 49.931 | 4.208 | 1.00 | 37.25 | 6 |
| ATOM | 924 | C | ALA | C | 245 | −2.983 | 50.617 | 5.184 | 1.00 | 32.82 | 6 |
| ATOM | 925 | O | ALA | C | 245 | −3.059 | 50.740 | 6.420 | 1.00 | 29.94 | 8 |
| ATOM | 926 | N | VAL | C | 246 | −1.907 | 50.246 | 4.499 | 1.00 | 33.79 | 7 |
| ATOM | 927 | CA | VAL | C | 246 | −0.705 | 49.866 | 5.266 | 1.00 | 29.90 | 6 |
| ATOM | 928 | CB | VAL | C | 246 | 0.366 | 49.269 | 4.369 | 1.00 | 29.88 | 6 |
| ATOM | 929 | CG1 | VAL | C | 246 | 0.056 | 47.917 | 3.771 | 1.00 | 34.43 | 6 |
| ATOM | 930 | CG2 | VAL | C | 246 | 1.773 | 49.346 | 4.931 | 1.00 | 29.74 | 6 |
| ATOM | 931 | C | VAL | C | 246 | −0.168 | 51.083 | 5.984 | 1.00 | 30.62 | 6 |
| ATOM | 932 | O | VAL | C | 246 | 0.208 | 51.067 | 7.166 | 1.00 | 29.83 | 8 |
| ATOM | 933 | N | VAL | C | 247 | −0.095 | 52.225 | 5.269 | 1.00 | 28.26 | 7 |
| ATOM | 934 | CA | VAL | C | 247 | 0.348 | 53.468 | 5.911 | 1.00 | 25.89 | 6 |
| ATOM | 935 | CB | VAL | C | 247 | 0.316 | 54.634 | 4.873 | 1.00 | 32.16 | 6 |
| ATOM | 936 | CG1 | VAL | C | 247 | 0.468 | 55.966 | 5.600 | 1.00 | 29.03 | 6 |
| ATOM | 937 | CG2 | VAL | C | 247 | 1.529 | 54.419 | 3.961 | 1.00 | 37.46 | 6 |
| ATOM | 938 | C | VAL | C | 247 | −0.533 | 53.832 | 7.100 | 1.00 | 28.13 | 6 |
| ATOM | 939 | O | VAL | C | 247 | −0.035 | 54.171 | 8.176 | 1.00 | 27.03 | 8 |
| ATOM | 940 | N | LYS | C | 248 | −1.851 | 53.790 | 6.935 | 1.00 | 25.46 | 7 |
| ATOM | 941 | CA | LYS | C | 248 | −2.739 | 54.143 | 8.033 | 1.00 | 28.62 | 6 |
| ATOM | 942 | CB | LYS | C | 248 | −4.215 | 54.072 | 7.623 | 1.00 | 41.92 | 6 |
| ATOM | 943 | CG | LYS | C | 248 | −5.117 | 54.460 | 8.801 | 1.00 | 55.47 | 6 |
| ATOM | 944 | CD | LYS | C | 248 | −6.509 | 53.868 | 8.678 | 1.00 | 53.90 | 6 |
| ATOM | 945 | CE | LYS | C | 248 | −7.538 | 54.663 | 9.470 | 1.00 | 57.26 | 6 |
| ATOM | 946 | NZ | LYS | C | 248 | −7.729 | 56.016 | 8.867 | 1.00 | 64.95 | 7 |
| ATOM | 947 | C | LYS | C | 248 | −2.548 | 53.220 | 9.240 | 1.00 | 27.15 | 6 |
| ATOM | 948 | O | LYS | C | 248 | −2.552 | 53.715 | 10.363 | 1.00 | 27.05 | 8 |
| ATOM | 949 | N | THR | C | 249 | −2.356 | 51.947 | 8.963 | 1.00 | 27.77 | 7 |
| ATOM | 950 | CA | THR | C | 249 | −2.134 | 50.940 | 9.998 | 1.00 | 25.68 | 6 |
| ATOM | 951 | CB | THR | C | 249 | −2.085 | 49.544 | 9.335 | 1.00 | 32.70 | 6 |
| ATOM | 952 | OG1 | THR | C | 249 | −3.453 | 49.231 | 8.992 | 1.00 | 33.92 | 8 |
| ATOM | 953 | CG2 | THR | C | 249 | −1.680 | 48.496 | 10.385 | 1.00 | 28.13 | 6 |
| ATOM | 954 | C | THR | C | 249 | −0.862 | 51.225 | 10.734 | 1.00 | 21.92 | 6 |
| ATOM | 955 | O | THR | C | 249 | −0.862 | 51.153 | 11.973 | 1.00 | 26.37 | 8 |
| ATOM | 956 | N | PHE | C | 250 | 0.224 | 51.510 | 10.052 | 1.00 | 24.01 | 7 |
| ATOM | 957 | CA | PHE | C | 250 | 1.452 | 51.874 | 10.753 | 1.00 | 22.16 | 6 |
| ATOM | 958 | CB | PHE | C | 250 | 2.617 | 51.986 | 9.764 | 1.00 | 23.90 | 6 |
| ATOM | 959 | CG | PHE | C | 250 | 3.359 | 50.719 | 9.523 | 1.00 | 20.12 | 6 |
| ATOM | 960 | CD1 | PHE | C | 250 | 2.740 | 49.629 | 8.943 | 1.00 | 26.67 | 6 |
| ATOM | 961 | CD2 | PHE | C | 250 | 4.703 | 50.639 | 9.883 | 1.00 | 24.12 | 6 |
| ATOM | 962 | CE1 | PHE | C | 250 | 3.448 | 48.448 | 8.753 | 1.00 | 25.84 | 6 |
| ATOM | 963 | CE2 | PHE | C | 250 | 5.393 | 49.449 | 9.704 | 1.00 | 26.95 | 6 |
| ATOM | 964 | CZ | PHE | C | 250 | 4.788 | 48.377 | 9.098 | 1.00 | 26.24 | 6 |
| ATOM | 965 | C | PHE | C | 250 | 1.272 | 53.105 | 11.613 | 1.00 | 23.98 | 6 |
| ATOM | 966 | O | PHE | C | 250 | 1.713 | 53.163 | 12.779 | 1.00 | 23.60 | 8 |
| ATOM | 967 | N | HIS | C | 251 | 0.654 | 54.143 | 11.040 | 1.00 | 23.00 | 7 |
| ATOM | 968 | CA | HIS | C | 251 | 0.506 | 55.406 | 11.779 | 1.00 | 24.29 | 6 |
| ATOM | 969 | CB | HIS | C | 251 | −0.108 | 56.474 | 10.895 | 1.00 | 28.22 | 6 |
| ATOM | 970 | CG | HIS | C | 251 | 0.848 | 56.857 | 9.809 | 1.00 | 22.07 | 6 |
| ATOM | 971 | CD2 | HIS | C | 251 | 2.172 | 56.586 | 9.687 | 1.00 | 20.33 | 6 |
| ATOM | 972 | ND1 | HIS | C | 251 | 0.474 | 57.604 | 8.733 | 1.00 | 27.95 | 7 |
| ATOM | 973 | CE1 | HIS | C | 251 | 1.546 | 57.774 | 7.977 | 1.00 | 24.46 | 6 |
| ATOM | 974 | NE2 | HIS | C | 251 | 2.594 | 57.162 | 8.476 | 1.00 | 23.12 | 7 |
| ATOM | 975 | C | HIS | C | 251 | −0.307 | 55.195 | 13.030 | 1.00 | 20.90 | 6 |
| ATOM | 976 | O | HIS | C | 251 | 0.070 | 55.675 | 14.085 | 1.00 | 27.74 | 8 |
| ATOM | 977 | N | GLU | C | 252 | −1.409 | 54.479 | 12.901 | 1.00 | 24.95 | 7 |
| ATOM | 978 | CA | GLU | C | 252 | −2.287 | 54.246 | 14.059 | 1.00 | 28.46 | 6 |
| ATOM | 979 | CB | GLU | C | 252 | −3.544 | 53.531 | 13.532 | 1.00 | 33.82 | 6 |
| ATOM | 980 | CG | GLU | C | 252 | −4.584 | 54.560 | 13.085 | 1.00 | 50.99 | 6 |
| ATOM | 981 | CD | GLU | C | 252 | −5.218 | 55.177 | 14.320 | 1.00 | 58.60 | 6 |
| ATOM | 982 | OE1 | GLU | C | 252 | −5.078 | 54.538 | 15.384 | 1.00 | 71.21 | 8 |
| ATOM | 983 | OE2 | GLU | C | 252 | −5.827 | 56.258 | 14.217 | 1.00 | 74.51 | 8 |
| ATOM | 984 | C | GLU | C | 252 | −1.649 | 53.320 | 15.076 | 1.00 | 25.23 | 6 |
| ATOM | 985 | O | GLU | C | 252 | −1.725 | 53.623 | 16.292 | 1.00 | 27.62 | 8 |
| ATOM | 986 | N | THR | C | 253 | −0.948 | 52.285 | 14.608 | 1.00 | 24.22 | 7 |
| ATOM | 987 | CA | THR | C | 253 | −0.336 | 51.351 | 15.541 | 1.00 | 25.24 | 6 |
| ATOM | 988 | CB | THR | C | 253 | 0.122 | 50.084 | 14.769 | 1.00 | 30.19 | 6 |
| ATOM | 989 | OG1 | THR | C | 253 | −1.087 | 49.511 | 14.236 | 1.00 | 29.93 | 8 |
| ATOM | 990 | CG2 | THR | C | 253 | 0.659 | 49.055 | 15.758 | 1.00 | 29.01 | 6 |
| ATOM | 991 | C | THR | C | 253 | 0.830 | 51.942 | 16.282 | 1.00 | 26.99 | 6 |
| ATOM | 992 | O | THR | C | 253 | 0.987 | 51.670 | 17.488 | 1.00 | 26.85 | 8 |
| ATOM | 993 | N | LEU | C | 254 | 1.663 | 52.716 | 15.590 | 1.00 | 25.36 | 7 |
| ATOM | 994 | CA | LEU | C | 254 | 2.892 | 53.221 | 16.188 | 1.00 | 25.88 | 6 |
| ATOM | 995 | CB | LEU | C | 254 | 4.109 | 53.104 | 15.238 | 1.00 | 26.52 | 6 |
| ATOM | 996 | CG | LEU | C | 254 | 4.359 | 51.782 | 14.532 | 1.00 | 28.64 | 6 |
| ATOM | 997 | CD1 | LEU | C | 254 | 5.319 | 51.868 | 13.356 | 1.00 | 26.29 | 6 |

-continued

PDB FILE LISTING –cd81el.pdb

| ATOM | 998 | CD2 | LEU | C | 254 | 4.785 | 50.714 | 15.546 | 1.00 | 31.46 | 6 |
|---|---|---|---|---|---|---|---|---|---|---|---|
| ATOM | 999 | C | LEU | C | 254 | 2.771 | 54.634 | 16.713 | 1.00 | 23.22 | 6 |
| ATOM | 1000 | O | LEU | C | 254 | 3.703 | 55.129 | 17.323 | 1.00 | 29.91 | 8 |
| ATOM | 1001 | N | ASP | C | 255 | 1.650 | 55.306 | 16.425 | 1.00 | 26.04 | 7 |
| ATOM | 1002 | CA | ASP | C | 255 | 1.388 | 56.653 | 16.899 | 1.00 | 28.87 | 6 |
| ATOM | 1003 | CB | ASP | C | 255 | 1.580 | 56.705 | 18.457 | 1.00 | 27.97 | 6 |
| ATOM | 1004 | CG | ASP | C | 255 | 0.731 | 57.830 | 19.007 | 1.00 | 38.75 | 6 |
| ATOM | 1005 | OD1 | ASP | C | 255 | −0.377 | 58.016 | 18.460 | 1.00 | 39.85 | 8 |
| ATOM | 1006 | OD2 | ASP | C | 255 | 1.167 | 58.483 | 19.981 | 1.00 | 49.40 | 8 |
| ATOM | 1007 | C | ASP | C | 255 | 2.398 | 57.629 | 16.324 | 1.00 | 26.53 | 6 |
| ATOM | 1008 | O | ASP | C | 255 | 3.180 | 58.334 | 16.965 | 1.00 | 30.14 | 8 |
| ATOM | 1009 | N | CYS | C | 256 | 2.413 | 57.598 | 14.957 | 1.00 | 23.58 | 7 |
| ATOM | 1010 | CA | CYS | C | 256 | 3.298 | 58.532 | 14.225 | 1.00 | 23.99 | 6 |
| ATOM | 1011 | C | CYS | C | 256 | 2.648 | 58.853 | 12.873 | 1.00 | 23.60 | 6 |
| ATOM | 1012 | O | CYS | C | 256 | 1.527 | 58.447 | 12.512 | 1.00 | 25.41 | 8 |
| ATOM | 1013 | CB | CYS | C | 256 | 4.637 | 57.834 | 13.913 | 1.00 | 27.13 | 6 |
| ATOM | 1014 | SG | CYS | C | 256 | 4.516 | 56.303 | 12.969 | 1.00 | 25.36 | 16 |
| ATOM | 1015 | N | CYS | C | 257 | 3.385 | 59.714 | 12.151 | 1.00 | 24.12 | 7 |
| ATOM | 1016 | CA | CYS | C | 257 | 2.892 | 60.177 | 10.853 | 1.00 | 23.16 | 6 |
| ATOM | 1017 | C | CYS | C | 257 | 4.139 | 60.542 | 10.014 | 1.00 | 24.72 | 6 |
| ATOM | 1018 | O | CYS | C | 257 | 4.847 | 61.504 | 10.308 | 1.00 | 35.05 | 8 |
| ATOM | 1019 | CB | CYS | C | 257 | 2.010 | 61.419 | 11.084 | 1.00 | 25.12 | 6 |
| ATOM | 1020 | SG | CYS | C | 257 | 1.467 | 62.126 | 9.517 | 1.00 | 38.79 | 16 |
| ATOM | 1021 | N | GLY | C | 258 | 4.489 | 59.747 | 9.012 | 1.00 | 28.13 | 7 |
| ATOM | 1022 | CA | GLY | C | 258 | 5.588 | 60.028 | 8.166 | 1.00 | 29.38 | 6 |
| ATOM | 1023 | C | GLY | C | 258 | 6.986 | 59.897 | 8.749 | 1.00 | 27.80 | 6 |
| ATOM | 1024 | O | GLY | C | 258 | 7.302 | 59.270 | 9.763 | 1.00 | 27.20 | 8 |
| ATOM | 1025 | N | SER | C | 259 | 7.907 | 60.517 | 7.979 | 1.00 | 23.88 | 7 |
| ATOM | 1026 | CA | SER | C | 259 | 9.319 | 60.378 | 8.276 | 1.00 | 24.44 | 6 |
| ATOM | 1027 | CB | SER | C | 259 | 9.939 | 59.307 | 7.342 | 1.00 | 24.84 | 6 |
| ATOM | 1028 | OG | SER | C | 259 | 11.346 | 59.213 | 7.645 | 1.00 | 24.95 | 8 |
| ATOM | 1029 | C | SER | C | 259 | 10.034 | 61.697 | 8.068 | 1.00 | 23.27 | 6 |
| ATOM | 1030 | O | SER | C | 259 | 9.868 | 62.267 | 6.973 | 1.00 | 25.69 | 8 |
| ATOM | 1031 | N | SER | C | 260 | 10.980 | 62.031 | 8.914 | 1.00 | 23.41 | 7 |
| ATOM | 1032 | CA | SER | C | 260 | 11.848 | 63.181 | 8.666 | 1.00 | 26.33 | 6 |
| ATOM | 1033 | CB | SER | C | 260 | 12.884 | 63.261 | 9.785 | 1.00 | 27.51 | 6 |
| ATOM | 1034 | OG | SER | C | 260 | 12.179 | 63.570 | 10.989 | 1.00 | 28.13 | 8 |
| ATOM | 1035 | C | SER | C | 260 | 12.676 | 63.039 | 7.371 | 1.00 | 29.57 | 6 |
| ATOM | 1036 | O | SER | C | 260 | 13.077 | 64.066 | 6.849 | 1.00 | 30.79 | 8 |
| ATOM | 1037 | N | THR | C | 261 | 12.896 | 61.841 | 6.873 | 1.00 | 26.07 | 7 |
| ATOM | 1038 | CA | THR | C | 261 | 13.692 | 61.604 | 5.669 | 1.00 | 27.09 | 6 |
| ATOM | 1039 | CB | THR | C | 261 | 14.272 | 60.165 | 5.682 | 1.00 | 33.47 | 6 |
| ATOM | 1040 | OG1 | THR | C | 261 | 13.261 | 59.151 | 5.651 | 1.00 | 27.38 | 8 |
| ATOM | 1041 | CG2 | THR | C | 261 | 15.173 | 59.975 | 6.879 | 1.00 | 32.39 | 6 |
| ATOM | 1042 | C | THR | C | 261 | 12.864 | 61.784 | 4.414 | 1.00 | 28.01 | 6 |
| ATOM | 1043 | O | THR | C | 261 | 13.421 | 61.744 | 3.288 | 1.00 | 30.80 | 8 |
| ATOM | 1044 | N | LEU | C | 262 | 11.552 | 61.893 | 4.543 | 1.00 | 24.40 | 7 |
| ATOM | 1045 | CA | LEU | C | 262 | 10.639 | 61.952 | 3.428 | 1.00 | 25.43 | 6 |
| ATOM | 1046 | CB | LEU | C | 262 | 9.914 | 60.611 | 3.138 | 1.00 | 28.21 | 6 |
| ATOM | 1047 | CG | LEU | C | 262 | 10.883 | 59.510 | 2.708 | 1.00 | 26.53 | 6 |
| ATOM | 1048 | CD1 | LEU | C | 262 | 10.350 | 58.121 | 2.895 | 1.00 | 30.08 | 6 |
| ATOM | 1049 | CD2 | LEU | C | 262 | 11.259 | 59.683 | 1.219 | 1.00 | 28.90 | 6 |
| ATOM | 1050 | C | LEU | C | 262 | 9.616 | 63.049 | 3.657 | 1.00 | 23.19 | 6 |
| ATOM | 1051 | O | LEU | C | 262 | 8.439 | 62.766 | 3.792 | 1.00 | 26.41 | 8 |
| ATOM | 1052 | N | THR | C | 263 | 10.094 | 64.280 | 3.767 | 1.00 | 26.39 | 7 |
| ATOM | 1053 | CA | THR | C | 263 | 9.161 | 65.386 | 4.059 | 1.00 | 27.72 | 6 |
| ATOM | 1054 | CB | THR | C | 263 | 9.896 | 66.696 | 4.405 | 1.00 | 25.97 | 6 |
| ATOM | 1055 | OG1 | THR | C | 263 | 10.729 | 66.986 | 3.282 | 1.00 | 30.14 | 8 |
| ATOM | 1056 | CG2 | THR | C | 263 | 10.827 | 66.427 | 5.589 | 1.00 | 27.82 | 6 |
| ATOM | 1057 | C | THR | C | 263 | 8.032 | 65.629 | 3.102 | 1.00 | 26.70 | 6 |
| ATOM | 1058 | O | THR | C | 263 | 6.878 | 65.844 | 3.504 | 1.00 | 28.71 | 8 |
| ATOM | 1059 | N | ALA | C | 264 | 8.304 | 65.522 | 1.773 | 1.00 | 26.68 | 7 |
| ATOM | 1060 | CA | ALA | C | 264 | 7.204 | 65.683 | 0.833 | 1.00 | 28.81 | 6 |
| ATOM | 1061 | CB | ALA | C | 264 | 7.792 | 65.684 | −0.583 | 1.00 | 37.35 | 6 |
| ATOM | 1062 | C | ALA | C | 264 | 6.131 | 64.613 | 0.943 | 1.00 | 29.88 | 6 |
| ATOM | 1063 | O | ALA | C | 264 | 4.928 | 64.893 | 0.823 | 1.00 | 27.29 | 8 |
| ATOM | 1064 | N | LEU | C | 265 | 6.556 | 63.336 | 1.110 | 1.00 | 26.34 | 7 |
| ATOM | 1065 | CA | LEU | C | 265 | 5.538 | 62.287 | 1.253 | 1.00 | 25.11 | 6 |
| ATOM | 1066 | CB | LEU | C | 265 | 6.196 | 60.887 | 1.270 | 1.00 | 28.31 | 6 |
| ATOM | 1067 | CG | LEU | C | 265 | 6.907 | 60.588 | −0.062 | 1.00 | 29.73 | 6 |
| ATOM | 1068 | CD1 | LEU | C | 265 | 7.569 | 59.240 | 0.095 | 1.00 | 33.59 | 6 |
| ATOM | 1069 | CD2 | LEU | C | 265 | 5.839 | 60.531 | −1.146 | 1.00 | 28.63 | 6 |
| ATOM | 1070 | C | LEU | C | 265 | 4.751 | 62.425 | 2.549 | 1.00 | 23.39 | 6 |
| ATOM | 1071 | O | LEU | C | 265 | 3.559 | 62.162 | 2.563 | 1.00 | 26.66 | 8 |
| ATOM | 1072 | N | THR | C | 266 | 5.439 | 63.023 | 3.542 | 1.00 | 25.29 | 7 |
| ATOM | 1073 | CA | THR | C | 266 | 4.716 | 63.271 | 4.808 | 1.00 | 22.08 | 6 |
| ATOM | 1074 | CB | THR | C | 266 | 5.727 | 63.729 | 5.881 | 1.00 | 23.25 | 6 |

-continued

PDB FILE LISTING –cd81el.pdb

| ATOM | 1075 | OG1 | THR | C | 266 | 6.648 | 62.625 | 6.056 | 1.00 | 25.07 | 8 |
|---|---|---|---|---|---|---|---|---|---|---|---|
| ATOM | 1076 | CG2 | THR | C | 266 | 5.058 | 63.990 | 7.240 | 1.00 | 23.91 | 6 |
| ATOM | 1077 | C | THR | C | 266 | 3.654 | 64.375 | 4.578 | 1.00 | 22.75 | 6 |
| ATOM | 1078 | O | THR | C | 266 | 2.556 | 64.260 | 5.081 | 1.00 | 28.42 | 8 |
| ATOM | 1079 | N | THR | C | 267 | 4.040 | 65.386 | 3.793 | 1.00 | 25.87 | 7 |
| ATOM | 1080 | CA | THR | C | 267 | 3.019 | 66.421 | 3.509 | 1.00 | 26.21 | 6 |
| ATOM | 1081 | CB | THR | C | 267 | 3.635 | 67.461 | 2.586 | 1.00 | 28.25 | 6 |
| ATOM | 1082 | OG1 | THR | C | 267 | 4.745 | 68.101 | 3.197 | 1.00 | 28.51 | 8 |
| ATOM | 1083 | CG2 | THR | C | 267 | 2.581 | 68.472 | 2.123 | 1.00 | 27.94 | 6 |
| ATOM | 1084 | C | THR | C | 267 | 1.818 | 65.733 | 2.855 | 1.00 | 27.78 | 6 |
| ATOM | 1085 | O | THR | C | 267 | 0.690 | 65.985 | 3.208 | 1.00 | 29.01 | 8 |
| ATOM | 1086 | N | SER | C | 268 | 2.094 | 64.819 | 1.906 | 1.00 | 27.61 | 7 |
| ATOM | 1087 | CA | SER | C | 268 | 0.979 | 64.143 | 1.229 | 1.00 | 25.35 | 6 |
| ATOM | 1088 | CB | SER | C | 268 | 1.548 | 63.536 | −0.058 | 1.00 | 32.95 | 6 |
| ATOM | 1089 | OG | SER | C | 268 | 0.564 | 62.685 | −0.630 | 1.00 | 44.07 | 8 |
| ATOM | 1090 | C | SER | C | 268 | 0.101 | 63.347 | 2.138 | 1.00 | 30.80 | 6 |
| ATOM | 1091 | O | SER | C | 268 | −1.147 | 63.435 | 2.174 | 1.00 | 33.02 | 8 |
| ATOM | 1092 | N | VAL | C | 269 | 0.728 | 62.580 | 3.065 | 1.00 | 27.58 | 7 |
| ATOM | 1093 | CA | VAL | C | 269 | −0.081 | 61.844 | 4.023 | 1.00 | 34.13 | 6 |
| ATOM | 1094 | CB | VAL | C | 269 | 0.621 | 60.665 | 4.655 | 1.00 | 38.22 | 6 |
| ATOM | 1095 | CG1 | VAL | C | 269 | 0.872 | 59.601 | 3.584 | 1.00 | 45.09 | 6 |
| ATOM | 1096 | CG2 | VAL | C | 269 | 1.899 | 61.022 | 5.375 | 1.00 | 44.36 | 6 |
| ATOM | 1097 | C | VAL | C | 269 | −0.922 | 62.762 | 4.888 | 1.00 | 30.87 | 6 |
| ATOM | 1098 | O | VAL | C | 269 | −2.068 | 62.347 | 5.141 | 1.00 | 33.47 | 8 |
| ATOM | 1099 | N | LEU | C | 270 | −0.426 | 63.946 | 5.266 | 1.00 | 28.56 | 7 |
| ATOM | 1100 | CA | LEU | C | 270 | −1.285 | 64.827 | 6.067 | 1.00 | 30.65 | 6 |
| ATOM | 1101 | CB | LEU | C | 270 | −0.460 | 66.044 | 6.549 | 1.00 | 36.56 | 6 |
| ATOM | 1102 | CG | LEU | C | 270 | 0.538 | 65.662 | 7.647 | 1.00 | 34.36 | 6 |
| ATOM | 1103 | CD1 | LEU | C | 270 | 1.529 | 66.803 | 7.862 | 1.00 | 41.70 | 6 |
| ATOM | 1104 | CD2 | LEU | C | 270 | −0.232 | 65.408 | 8.925 | 1.00 | 35.94 | 6 |
| ATOM | 1105 | C | LEU | C | 270 | −2.396 | 65.387 | 5.189 | 1.00 | 33.16 | 6 |
| ATOM | 1106 | O | LEU | C | 270 | −3.505 | 65.574 | 5.686 | 1.00 | 45.89 | 8 |
| ATOM | 1107 | N | LYS | C | 271 | −2.124 | 65.660 | 3.938 | 1.00 | 34.32 | 7 |
| ATOM | 1108 | CA | LYS | C | 271 | −3.134 | 66.246 | 3.050 | 1.00 | 41.10 | 6 |
| ATOM | 1109 | CB | LYS | C | 271 | −2.472 | 66.769 | 1.783 | 1.00 | 32.67 | 6 |
| ATOM | 1110 | CG | LYS | C | 271 | −2.127 | 68.233 | 1.717 | 1.00 | 43.61 | 6 |
| ATOM | 1111 | CD | LYS | C | 271 | −0.952 | 68.551 | 0.830 | 1.00 | 50.73 | 6 |
| ATOM | 1112 | CE | LYS | C | 271 | −1.260 | 69.015 | −0.572 | 1.00 | 54.10 | 6 |
| ATOM | 1113 | NZ | LYS | C | 271 | −0.039 | 69.130 | −1.431 | 1.00 | 56.13 | 7 |
| ATOM | 1114 | C | LYS | C | 271 | −4.193 | 65.214 | 2.672 | 1.00 | 46.38 | 6 |
| ATOM | 1115 | O | LYS | C | 271 | −5.236 | 65.554 | 2.114 | 1.00 | 47.27 | 8 |
| ATOM | 1116 | N | ASN | C | 272 | −3.879 | 63.946 | 2.880 | 1.00 | 45.09 | 7 |
| ATOM | 1117 | CA | ASN | C | 272 | −4.778 | 62.853 | 2.522 | 1.00 | 43.41 | 6 |
| ATOM | 1118 | CB | ASN | C | 272 | −4.086 | 61.857 | 1.593 | 1.00 | 50.61 | 6 |
| ATOM | 1119 | CG | ASN | C | 272 | −3.723 | 62.457 | 0.250 | 1.00 | 49.74 | 6 |
| ATOM | 1120 | OD1 | ASN | C | 272 | −2.963 | 61.847 | −0.503 | 1.00 | 60.30 | 8 |
| ATOM | 1121 | ND2 | ASN | C | 272 | −4.256 | 63.636 | −0.037 | 1.00 | 52.35 | 7 |
| ATOM | 1122 | C | ASN | C | 272 | −5.367 | 62.117 | 3.710 | 1.00 | 42.86 | 6 |
| ATOM | 1123 | O | ASN | C | 272 | −5.855 | 60.989 | 3.575 | 1.00 | 42.83 | 8 |
| ATOM | 1124 | N | ASN | C | 273 | −5.378 | 62.712 | 4.895 | 1.00 | 42.22 | 7 |
| ATOM | 1125 | CA | ASN | C | 273 | −5.956 | 62.073 | 6.073 | 1.00 | 44.58 | 6 |
| ATOM | 1126 | CB | ASN | C | 273 | −7.465 | 62.188 | 6.138 | 1.00 | 52.14 | 6 |
| ATOM | 1127 | CG | ASN | C | 273 | −8.169 | 61.943 | 7.449 | 1.00 | 66.60 | 6 |
| ATOM | 1128 | OD1 | ASN | C | 273 | −9.311 | 61.452 | 7.442 | 1.00 | 61.59 | 8 |
| ATOM | 1129 | ND2 | ASN | C | 273 | −7.599 | 62.249 | 8.609 | 1.00 | 53.47 | 7 |
| ATOM | 1130 | C | ASN | C | 273 | −5.447 | 60.654 | 6.272 | 1.00 | 44.46 | 6 |
| ATOM | 1131 | O | ASN | C | 273 | −6.213 | 59.729 | 6.565 | 1.00 | 42.25 | 8 |
| ATOM | 1132 | N | LEU | C | 274 | −4.120 | 60.506 | 6.183 | 1.00 | 33.07 | 7 |
| ATOM | 1133 | CA | LEU | C | 274 | −3.513 | 59.186 | 6.407 | 1.00 | 37.06 | 6 |
| ATOM | 1134 | CB | LEU | C | 274 | −2.550 | 58.789 | 5.288 | 1.00 | 33.35 | 6 |
| ATOM | 1135 | CG | LEU | C | 274 | −3.171 | 58.526 | 3.908 | 1.00 | 36.17 | 6 |
| ATOM | 1136 | CD1 | LEU | C | 274 | −2.201 | 58.059 | 2.854 | 1.00 | 35.69 | 6 |
| ATOM | 1137 | CD2 | LEU | C | 274 | −4.292 | 57.498 | 4.023 | 1.00 | 42.68 | 6 |
| ATOM | 1138 | C | LEU | C | 274 | −2.827 | 59.212 | 7.772 | 1.00 | 35.03 | 6 |
| ATOM | 1139 | O | LEU | C | 274 | −2.224 | 58.213 | 8.172 | 1.00 | 39.17 | 8 |
| ATOM | 1140 | N | CYS | C | 275 | −3.049 | 60.262 | 8.549 | 1.00 | 34.81 | 7 |
| ATOM | 1141 | CA | CYS | C | 275 | −2.477 | 60.330 | 9.886 | 1.00 | 36.93 | 6 |
| ATOM | 1142 | C | CYS | C | 275 | −3.551 | 60.482 | 10.979 | 1.00 | 41.89 | 6 |
| ATOM | 1143 | O | CYS | C | 275 | −4.507 | 61.231 | 10.816 | 1.00 | 42.44 | 8 |
| ATOM | 1144 | CB | CYS | C | 275 | −1.450 | 61.458 | 9.952 | 1.00 | 37.22 | 6 |
| ATOM | 1145 | SG | CYS | C | 275 | 0.032 | 61.171 | 8.939 | 1.00 | 40.09 | 16 |
| ATOM | 1146 | N | PRO | C | 276 | −3.307 | 59.747 | 12.085 | 1.00 | 43.00 | 7 |
| ATOM | 1147 | CD | PRO | C | 276 | −2.168 | 58.833 | 12.246 | 1.00 | 46.79 | 6 |
| ATOM | 1148 | CA | PRO | C | 276 | −4.227 | 59.720 | 13.270 | 1.00 | 45.18 | 6 |
| ATOM | 1149 | CB | PRO | C | 276 | −3.501 | 58.834 | 14.281 | 1.00 | 43.00 | 6 |
| ATOM | 1150 | CG | PRO | C | 276 | −2.108 | 58.658 | 13.734 | 1.00 | 44.89 | 6 |
| ATOM | 1151 | C | PRO | C | 276 | −4.522 | 61.074 | 13.906 | 1.00 | 44.90 | 6 |

-continued

PDB FILE LISTING –cd81el.pdb

| ATOM | 1152 | O   | PRO | C | 276 | −3.683 | 61.964 | 13.848 | 1.00 | 40.22 | 8 |
|------|------|-----|-----|---|-----|--------|--------|--------|------|-------|---|
| ATOM | 1153 | N   | SER | C | 277 | −5.702 | 61.239 | 14.523 | 1.00 | 49.31 | 7 |
| ATOM | 1154 | CA  | SER | C | 277 | −6.057 | 62.560 | 15.080 | 1.00 | 53.44 | 6 |
| ATOM | 1155 | CB  | SER | C | 277 | −7.590 | 62.750 | 15.034 | 1.00 | 61.29 | 6 |
| ATOM | 1156 | OG  | SER | C | 277 | −7.984 | 63.864 | 15.817 | 1.00 | 59.45 | 8 |
| ATOM | 1157 | C   | SER | C | 277 | −5.531 | 62.914 | 16.533 | 1.00 | 56.84 | 6 |
| ATOM | 1158 | O   | SER | C | 277 | −6.323 | 63.093 | 17.457 | 1.00 | 58.71 | 8 |
| ATOM | 1159 | N   | GLY | C | 278 | −4.196 | 63.036 | 16.701 | 0.00 | 72.91 | 7 |
| ATOM | 1160 | CA  | GLY | C | 278 | −3.535 | 63.382 | 17.979 | 0.00 | 72.16 | 6 |
| ATOM | 1161 | C   | GLY | C | 278 | −2.623 | 64.645 | 17.863 | 0.00 | 71.11 | 6 |
| ATOM | 1162 | O   | GLY | C | 278 | −1.651 | 64.671 | 17.108 | 0.00 | 72.04 | 8 |
| ATOM | 1163 | N   | GLY | C | 279 | −3.014 | 65.688 | 18.600 | 0.00 | 67.96 | 7 |
| ATOM | 1164 | CA  | GLY | C | 279 | −2.296 | 66.962 | 18.676 | 0.00 | 66.01 | 6 |
| ATOM | 1165 | C   | GLY | C | 279 | −0.889 | 66.636 | 19.187 | 0.00 | 61.41 | 6 |
| ATOM | 1166 | O   | GLY | C | 279 | 0.045  | 67.424 | 19.020 | 0.00 | 60.21 | 8 |
| ATOM | 1167 | N   | ASN | C | 280 | −0.768 | 65.439 | 19.816 | 0.00 | 43.63 | 7 |
| ATOM | 1168 | CA  | ASN | C | 280 | 0.471  | 64.860 | 20.274 | 1.00 | 41.26 | 6 |
| ATOM | 1169 | CB  | ASN | C | 280 | 0.281  | 63.676 | 21.248 | 1.00 | 51.58 | 6 |
| ATOM | 1170 | CG  | ASN | C | 280 | 1.538  | 62.874 | 21.591 | 1.00 | 65.06 | 6 |
| ATOM | 1171 | OD1 | ASN | C | 280 | 2.201  | 63.121 | 22.603 | 1.00 | 62.58 | 8 |
| ATOM | 1172 | ND2 | ASN | C | 280 | 1.863  | 61.923 | 20.739 | 1.00 | 69.23 | 7 |
| ATOM | 1173 | C   | ASN | C | 280 | 1.134  | 64.414 | 19.000 | 1.00 | 39.27 | 6 |
| ATOM | 1174 | O   | ASN | C | 280 | 2.367  | 64.438 | 18.861 | 1.00 | 43.66 | 8 |
| ATOM | 1175 | N   | ILE | C | 281 | 0.309  | 63.983 | 18.044 | 1.00 | 37.18 | 7 |
| ATOM | 1176 | CA  | ILE | C | 281 | 0.909  | 63.540 | 16.783 | 1.00 | 39.37 | 6 |
| ATOM | 1177 | CB  | ILE | C | 281 | −0.106 | 62.955 | 15.765 | 1.00 | 35.78 | 6 |
| ATOM | 1178 | CG2 | ILE | C | 281 | 0.541  | 62.824 | 14.398 | 1.00 | 53.65 | 6 |
| ATOM | 1179 | CG1 | ILE | C | 281 | −0.652 | 61.595 | 16.245 | 1.00 | 34.01 | 6 |
| ATOM | 1180 | CD1 | ILE | C | 281 | 0.391  | 60.510 | 16.337 | 1.00 | 39.13 | 6 |
| ATOM | 1181 | C   | ILE | C | 281 | 1.619  | 64.698 | 16.132 | 1.00 | 37.32 | 6 |
| ATOM | 1182 | O   | ILE | C | 281 | 2.790  | 64.607 | 15.753 | 1.00 | 37.87 | 8 |
| ATOM | 1183 | N   | ILE | C | 282 | 0.906  | 65.826 | 16.001 | 1.00 | 29.62 | 7 |
| ATOM | 1184 | CA  | ILE | C | 282 | 1.445  | 66.989 | 15.332 | 1.00 | 29.15 | 6 |
| ATOM | 1185 | CB  | ILE | C | 282 | 0.318  | 68.006 | 15.057 | 1.00 | 29.10 | 6 |
| ATOM | 1186 | CG2 | ILE | C | 282 | 0.792  | 69.228 | 14.292 | 1.00 | 33.23 | 6 |
| ATOM | 1187 | CG1 | ILE | C | 282 | −0.887 | 67.372 | 14.382 | 1.00 | 37.23 | 6 |
| ATOM | 1188 | CD1 | ILE | C | 282 | −0.521 | 66.651 | 13.108 | 1.00 | 39.06 | 6 |
| ATOM | 1189 | C   | ILE | C | 282 | 2.622  | 67.555 | 16.086 | 1.00 | 27.74 | 6 |
| ATOM | 1190 | O   | ILE | C | 282 | 3.616  | 67.958 | 15.470 | 1.00 | 27.48 | 8 |
| ATOM | 1191 | N   | SER | C | 283 | 2.536  | 67.671 | 17.429 | 1.00 | 31.63 | 7 |
| ATOM | 1192 | CA  | SER | C | 283 | 3.632  | 68.234 | 18.186 | 1.00 | 28.41 | 6 |
| ATOM | 1193 | CB  | SER | C | 283 | 3.217  | 68.521 | 19.632 | 1.00 | 37.49 | 6 |
| ATOM | 1194 | OG  | SER | C | 283 | 3.292  | 67.403 | 20.469 | 1.00 | 52.68 | 8 |
| ATOM | 1195 | C   | SER | C | 283 | 4.900  | 67.401 | 18.084 | 1.00 | 30.27 | 6 |
| ATOM | 1196 | O   | SER | C | 283 | 6.003  | 67.938 | 18.285 | 1.00 | 30.36 | 8 |
| ATOM | 1197 | N   | ASN | C | 284 | 4.773  | 66.116 | 17.783 | 1.00 | 26.22 | 7 |
| ATOM | 1198 | CA  | ASN | C | 284 | 5.959  | 65.269 | 17.620 | 1.00 | 27.42 | 6 |
| ATOM | 1199 | CB  | ASN | C | 284 | 5.744  | 64.023 | 18.532 | 1.00 | 29.26 | 6 |
| ATOM | 1200 | CG  | ASN | C | 284 | 5.959  | 64.586 | 19.955 | 1.00 | 36.37 | 6 |
| ATOM | 1201 | OD1 | ASN | C | 284 | 7.018  | 65.179 | 20.173 | 1.00 | 34.52 | 8 |
| ATOM | 1202 | ND2 | ASN | C | 284 | 4.959  | 64.417 | 20.770 | 1.00 | 39.70 | 7 |
| ATOM | 1203 | C   | ASN | C | 284 | 6.060  | 64.717 | 16.192 | 1.00 | 22.07 | 6 |
| ATOM | 1204 | O   | ASN | C | 284 | 6.730  | 63.711 | 15.988 | 1.00 | 27.09 | 8 |
| ATOM | 1205 | N   | LEU | C | 285 | 5.436  | 65.408 | 15.232 | 1.00 | 25.57 | 7 |
| ATOM | 1206 | CA  | LEU | C | 285 | 5.477  | 64.935 | 13.835 | 1.00 | 24.22 | 6 |
| ATOM | 1207 | CB  | LEU | C | 285 | 5.021  | 66.064 | 12.899 | 1.00 | 28.37 | 6 |
| ATOM | 1208 | CG  | LEU | C | 285 | 5.034  | 65.744 | 11.397 | 1.00 | 27.69 | 6 |
| ATOM | 1209 | CD1 | LEU | C | 285 | 4.105  | 64.552 | 11.189 | 1.00 | 27.75 | 6 |
| ATOM | 1210 | CD2 | LEU | C | 285 | 4.488  | 66.992 | 10.655 | 1.00 | 24.39 | 6 |
| ATOM | 1211 | C   | LEU | C | 285 | 6.822  | 64.396 | 13.386 | 1.00 | 28.96 | 6 |
| ATOM | 1212 | O   | LEU | C | 285 | 6.917  | 63.272 | 12.850 | 1.00 | 26.23 | 8 |
| ATOM | 1213 | N   | PHE | C | 286 | 7.891  | 65.192 | 13.539 | 1.00 | 25.55 | 7 |
| ATOM | 1214 | CA  | PHE | C | 286 | 9.221  | 64.787 | 13.177 | 1.00 | 23.44 | 6 |
| ATOM | 1215 | CB  | PHE | C | 286 | 9.906  | 65.839 | 12.290 | 1.00 | 23.03 | 6 |
| ATOM | 1216 | CG  | PHE | C | 286 | 9.199  | 65.986 | 10.955 | 1.00 | 20.67 | 6 |
| ATOM | 1217 | CD1 | PHE | C | 286 | 8.607  | 67.187 | 10.626 | 1.00 | 23.30 | 6 |
| ATOM | 1218 | CD2 | PHE | C | 286 | 9.115  | 64.917 | 10.076 | 1.00 | 24.24 | 6 |
| ATOM | 1219 | CE1 | PHE | C | 286 | 7.950  | 67.339 | 9.417  | 1.00 | 28.29 | 6 |
| ATOM | 1220 | CE2 | PHE | C | 286 | 8.487  | 65.083 | 8.856  | 1.00 | 25.76 | 6 |
| ATOM | 1221 | CZ  | PHE | C | 286 | 7.926  | 66.293 | 8.495  | 1.00 | 25.94 | 6 |
| ATOM | 1222 | C   | PHE | C | 286 | 10.085 | 64.498 | 14.414 | 1.00 | 24.30 | 6 |
| ATOM | 1223 | O   | PHE | C | 286 | 11.143 | 63.917 | 14.225 | 1.00 | 28.00 | 8 |
| ATOM | 1224 | N   | LYS | C | 287 | 9.635  | 64.960 | 15.579 | 1.00 | 25.79 | 7 |
| ATOM | 1225 | CA  | LYS | C | 287 | 10.472 | 64.671 | 16.761 | 1.00 | 28.66 | 6 |
| ATOM | 1226 | CB  | LYS | C | 287 | 9.975  | 65.378 | 18.014 | 1.00 | 30.74 | 6 |
| ATOM | 1227 | CG  | LYS | C | 287 | 10.046 | 66.886 | 17.851 | 1.00 | 39.07 | 6 |
| ATOM | 1228 | CD  | LYS | C | 287 | 9.564  | 67.582 | 19.120 | 1.00 | 37.66 | 6 |

-continued

PDB FILE LISTING –cd81el.pdb

| ATOM | 1229 | CE  | LYS | C | 287 | 10.235 | 67.045 | 20.364 | 1.00 | 44.51 | 6  |
| ATOM | 1230 | NZ  | LYS | C | 287 | 9.589  | 67.630 | 21.579 | 1.00 | 51.78 | 7  |
| ATOM | 1231 | C   | LYS | C | 287 | 10.393 | 63.163 | 17.058 | 1.00 | 27.32 | 6  |
| ATOM | 1232 | O   | LYS | C | 287 | 11.378 | 62.681 | 17.638 | 1.00 | 32.08 | 8  |
| ATOM | 1233 | N   | GLU | C | 288 | 9.262  | 62.558 | 16.853 | 1.00 | 25.65 | 7  |
| ATOM | 1234 | CA  | GLU | C | 288 | 9.168  | 61.109 | 17.057 | 1.00 | 26.38 | 6  |
| ATOM | 1235 | CB  | GLU | C | 288 | 8.405  | 60.799 | 18.330 | 1.00 | 32.61 | 6  |
| ATOM | 1236 | CG  | GLU | C | 288 | 8.883  | 61.580 | 19.545 | 1.00 | 35.86 | 6  |
| ATOM | 1237 | CD  | GLU | C | 288 | 7.953  | 61.282 | 20.715 | 1.00 | 49.68 | 6  |
| ATOM | 1238 | OE1 | GLU | C | 288 | 7.772  | 62.105 | 21.631 | 1.00 | 55.75 | 8  |
| ATOM | 1239 | OE2 | GLU | C | 288 | 7.361  | 60.177 | 20.724 | 1.00 | 63.52 | 8  |
| ATOM | 1240 | C   | GLU | C | 288 | 8.424  | 60.477 | 15.876 | 1.00 | 24.79 | 6  |
| ATOM | 1241 | O   | GLU | C | 288 | 7.289  | 60.032 | 15.983 | 1.00 | 25.16 | 8  |
| ATOM | 1242 | N   | ASP | C | 289 | 9.125  | 60.434 | 14.753 | 1.00 | 26.85 | 7  |
| ATOM | 1243 | CA  | ASP | C | 289 | 8.568  | 59.980 | 13.508 | 1.00 | 24.56 | 6  |
| ATOM | 1244 | CB  | ASP | C | 289 | 9.369  | 60.684 | 12.398 | 1.00 | 25.50 | 6  |
| ATOM | 1245 | CG  | ASP | C | 289 | 10.715 | 60.115 | 12.072 | 1.00 | 27.35 | 6  |
| ATOM | 1246 | OD1 | ASP | C | 289 | 11.562 | 60.768 | 11.372 | 1.00 | 26.87 | 8  |
| ATOM | 1247 | OD2 | ASP | C | 289 | 11.060 | 58.983 | 12.489 | 1.00 | 26.73 | 8  |
| ATOM | 1248 | C   | ASP | C | 289 | 8.519  | 58.474 | 13.355 | 1.00 | 25.27 | 6  |
| ATOM | 1249 | O   | ASP | C | 289 | 8.888  | 57.761 | 14.315 | 1.00 | 24.29 | 8  |
| ATOM | 1250 | N   | CYS | C | 290 | 7.889  | 57.995 | 12.292 | 1.00 | 22.72 | 7  |
| ATOM | 1251 | CA  | CYS | C | 290 | 7.722  | 56.512 | 12.197 | 1.00 | 21.85 | 6  |
| ATOM | 1252 | C   | CYS | C | 290 | 9.039  | 55.781 | 12.183 | 1.00 | 23.09 | 6  |
| ATOM | 1253 | O   | CYS | C | 290 | 8.987  | 54.628 | 12.645 | 1.00 | 24.17 | 8  |
| ATOM | 1254 | CB  | CYS | C | 290 | 6.862  | 56.136 | 11.009 | 1.00 | 26.13 | 6  |
| ATOM | 1255 | SG  | CYS | C | 290 | 5.240  | 56.851 | 11.104 | 1.00 | 24.30 | 16 |
| ATOM | 1256 | N   | HIS | C | 291 | 10.181 | 56.308 | 11.712 | 1.00 | 21.89 | 7  |
| ATOM | 1257 | CA  | HIS | C | 291 | 11.421 | 55.547 | 11.830 | 1.00 | 19.74 | 6  |
| ATOM | 1258 | CB  | HIS | C | 291 | 12.547 | 56.294 | 11.070 | 1.00 | 25.39 | 6  |
| ATOM | 1259 | CG  | HIS | C | 291 | 12.326 | 56.132 | 9.596  | 1.00 | 23.25 | 6  |
| ATOM | 1260 | CD2 | HIS | C | 291 | 11.317 | 55.748 | 8.792  | 1.00 | 26.31 | 6  |
| ATOM | 1261 | ND1 | HIS | C | 291 | 13.423 | 56.382 | 8.784  | 1.00 | 27.59 | 7  |
| ATOM | 1262 | CE1 | HIS | C | 291 | 13.078 | 56.155 | 7.514  | 1.00 | 30.34 | 6  |
| ATOM | 1263 | NE2 | HIS | C | 291 | 11.831 | 55.757 | 7.489  | 1.00 | 25.82 | 7  |
| ATOM | 1264 | C   | HIS | C | 291 | 11.759 | 55.412 | 13.318 | 1.00 | 22.34 | 6  |
| ATOM | 1265 | O   | HIS | C | 291 | 12.280 | 54.354 | 13.735 | 1.00 | 25.37 | 8  |
| ATOM | 1266 | N   | GLN | C | 292 | 11.615 | 56.518 | 14.052 | 1.00 | 20.97 | 7  |
| ATOM | 1267 | CA  | GLN | C | 292 | 11.899 | 56.386 | 15.511 | 1.00 | 21.60 | 6  |
| ATOM | 1268 | CB  | GLN | C | 292 | 11.760 | 57.772 | 16.145 | 1.00 | 27.40 | 6  |
| ATOM | 1269 | CG  | GLN | C | 292 | 12.000 | 57.661 | 17.656 | 1.00 | 28.40 | 6  |
| ATOM | 1270 | CD  | GLN | C | 292 | 13.484 | 57.430 | 17.859 | 1.00 | 32.24 | 6  |
| ATOM | 1271 | QE1 | GLN | C | 292 | 14.393 | 58.103 | 17.336 | 1.00 | 39.00 | 8  |
| ATOM | 1272 | NE2 | GLN | C | 292 | 13.874 | 56.455 | 18.679 | 1.00 | 35.20 | 7  |
| ATOM | 1273 | C   | GLN | C | 292 | 10.977 | 55.406 | 16.173 | 1.00 | 22.96 | 6  |
| ATOM | 1274 | O   | GLN | C | 292 | 11.439 | 54.599 | 17.005 | 1.00 | 25.46 | 8  |
| ATOM | 1275 | N   | LYS | C | 293 | 9.706  | 55.391 | 15.844 | 1.00 | 20.49 | 7  |
| ATOM | 1276 | CA  | LYS | C | 293 | 8.766  | 54.437 | 16.454 | 1.00 | 24.11 | 6  |
| ATOM | 1277 | CB  | LYS | C | 293 | 7.316  | 54.705 | 16.123 | 1.00 | 21.49 | 6  |
| ATOM | 1278 | CG  | LYS | C | 293 | 6.906  | 56.132 | 16.541 | 1.00 | 20.82 | 6  |
| ATOM | 1279 | CD  | LYS | C | 293 | 7.166  | 56.246 | 18.080 | 1.00 | 26.19 | 6  |
| ATOM | 1280 | CE  | LYS | C | 293 | 6.380  | 57.510 | 18.465 | 1.00 | 31.71 | 6  |
| ATOM | 1281 | NZ  | LYS | C | 293 | 6.412  | 57.682 | 19.953 | 1.00 | 43.53 | 7  |
| ATOM | 1282 | C   | LYS | C | 293 | 9.094  | 52.995 | 16.091 | 1.00 | 24.90 | 6  |
| ATOM | 1283 | O   | LYS | C | 293 | 9.021  | 52.081 | 16.925 | 1.00 | 25.35 | 8  |
| ATOM | 1284 | N   | ILE | C | 294 | 9.502  | 52.769 | 14.834 | 1.00 | 23.01 | 7  |
| ATOM | 1285 | CA  | ILE | C | 294 | 9.914  | 51.416 | 14.443 | 1.00 | 21.69 | 6  |
| ATOM | 1286 | CB  | ILE | C | 294 | 10.149 | 51.365 | 12.898 | 1.00 | 20.45 | 6  |
| ATOM | 1287 | CG2 | ILE | C | 294 | 10.902 | 50.053 | 12.595 | 1.00 | 22.39 | 6  |
| ATOM | 1288 | CG1 | ILE | C | 294 | 8.826  | 51.424 | 12.182 | 1.00 | 22.59 | 6  |
| ATOM | 1289 | CD1 | ILE | C | 294 | 9.013  | 51.723 | 10.682 | 1.00 | 22.71 | 6  |
| ATOM | 1290 | C   | ILE | C | 294 | 11.139 | 50.978 | 15.210 | 1.00 | 21.79 | 6  |
| ATOM | 1291 | O   | ILE | C | 294 | 11.250 | 49.852 | 15.725 | 1.00 | 23.79 | 8  |
| ATOM | 1292 | N   | ASP | C | 295 | 12.098 | 51.912 | 15.441 | 1.00 | 23.67 | 7  |
| ATOM | 1293 | CA  | ASP | C | 295 | 13.281 | 51.560 | 16.213 | 1.00 | 23.07 | 6  |
| ATOM | 1294 | CB  | ASP | C | 295 | 14.291 | 52.722 | 16.301 | 1.00 | 27.78 | 6  |
| ATOM | 1295 | CG  | ASP | C | 295 | 15.082 | 52.938 | 15.034 | 1.00 | 37.31 | 6  |
| ATOM | 1296 | OD1 | ASP | C | 295 | 15.209 | 51.983 | 14.243 | 1.00 | 32.94 | 8  |
| ATOM | 1297 | OD2 | ASP | C | 295 | 15.570 | 54.098 | 14.872 | 1.00 | 41.42 | 8  |
| ATOM | 1298 | C   | ASP | C | 295 | 12.825 | 51.240 | 17.666 | 1.00 | 23.22 | 6  |
| ATOM | 1299 | O   | ASP | C | 295 | 13.357 | 50.303 | 18.289 | 1.00 | 26.53 | 8  |
| ATOM | 1300 | N   | ASP | C | 296 | 11.931 | 52.047 | 18.194 | 1.00 | 23.58 | 7  |
| ATOM | 1301 | CA  | ASP | C | 296 | 11.458 | 51.889 | 19.570 | 1.00 | 23.39 | 6  |
| ATOM | 1302 | CB  | ASP | C | 296 | 10.529 | 53.012 | 20.025 | 1.00 | 27.78 | 6  |
| ATOM | 1303 | CG  | ASP | C | 296 | 11.224 | 54.362 | 20.124 | 1.00 | 29.71 | 6  |
| ATOM | 1304 | OD1 | ASP | C | 296 | 12.461 | 54.427 | 20.176 | 1.00 | 31.37 | 8  |
| ATOM | 1305 | OD2 | ASP | C | 296 | 10.444 | 55.326 | 20.197 | 1.00 | 39.13 | 8  |

-continued

PDB FILE LISTING –cd81el.pdb

| | | | | | | | | | | |
|---|---|---|---|---|---|---|---|---|---|---|
| ATOM | 1306 | C | ASP | C | 296 | 10.756 | 50.552 | 19.733 | 1.00 | 27.01 | 6 |
| ATOM | 1307 | O | ASP | C | 296 | 10.850 | 49.914 | 20.794 | 1.00 | 29.39 | 8 |
| ATOM | 1308 | N | LEU | C | 297 | 10.007 | 50.102 | 18.742 | 1.00 | 23.26 | 7 |
| ATOM | 1309 | CA | LEU | C | 297 | 9.314 | 48.820 | 18.800 | 1.00 | 26.92 | 6 |
| ATOM | 1310 | CB | LEU | C | 297 | 8.515 | 48.599 | 17.481 | 1.00 | 23.50 | 6 |
| ATOM | 1311 | CG | LEU | C | 297 | 7.865 | 47.206 | 17.409 | 1.00 | 25.96 | 6 |
| ATOM | 1312 | CD1 | LEU | C | 297 | 6.821 | 46.978 | 18.514 | 1.00 | 23.25 | 6 |
| ATOM | 1313 | CD2 | LEU | C | 297 | 7.209 | 47.043 | 16.056 | 1.00 | 30.08 | 6 |
| ATOM | 1314 | C | LEU | C | 297 | 10.319 | 47.700 | 18.994 | 1.00 | 22.60 | 6 |
| ATOM | 1315 | O | LEU | C | 297 | 10.238 | 46.833 | 19.871 | 1.00 | 25.36 | 8 |
| ATOM | 1316 | N | PHE | C | 298 | 11.370 | 47.704 | 18.181 | 1.00 | 22.46 | 7 |
| ATOM | 1317 | CA | PHE | C | 298 | 12.397 | 46.657 | 18.190 | 1.00 | 22.98 | 6 |
| ATOM | 1318 | CB | PHE | C | 298 | 13.146 | 46.534 | 16.828 | 1.00 | 21.20 | 6 |
| ATOM | 1319 | CG | PHE | C | 298 | 12.215 | 45.936 | 15.763 | 1.00 | 21.65 | 6 |
| ATOM | 1320 | CD1 | PHE | C | 298 | 11.603 | 46.775 | 14.851 | 1.00 | 23.88 | 6 |
| ATOM | 1321 | CD2 | PHE | C | 298 | 11.945 | 44.579 | 15.727 | 1.00 | 19.61 | 6 |
| ATOM | 1322 | CE1 | PHE | C | 298 | 10.711 | 46.287 | 13.918 | 1.00 | 23.10 | 6 |
| ATOM | 1323 | CE2 | PHE | C | 298 | 10.976 | 44.082 | 14.879 | 1.00 | 22.89 | 6 |
| ATOM | 1324 | CZ | PHE | C | 298 | 10.385 | 44.944 | 13.954 | 1.00 | 22.89 | 6 |
| ATOM | 1325 | C | PHE | C | 298 | 13.346 | 46.765 | 19.366 | 1.00 | 22.24 | 6 |
| ATOM | 1326 | O | PHE | C | 298 | 13.995 | 45.762 | 19.696 | 1.00 | 26.14 | 8 |
| ATOM | 1327 | N | SER | C | 299 | 13.452 | 47.932 | 19.987 | 1.00 | 25.90 | 7 |
| ATOM | 1328 | CA | SER | C | 299 | 14.264 | 48.166 | 21.163 | 1.00 | 27.99 | 6 |
| ATOM | 1329 | CB | SER | C | 299 | 14.694 | 49.677 | 21.208 | 1.00 | 28.04 | 6 |
| ATOM | 1330 | OG | SER | C | 299 | 15.551 | 49.835 | 20.076 | 1.00 | 48.85 | 8 |
| ATOM | 1331 | C | SER | C | 299 | 13.465 | 47.944 | 22.441 | 1.00 | 27.66 | 6 |
| ATOM | 1332 | O | SER | C | 299 | 14.116 | 47.914 | 23.506 | 1.00 | 33.14 | 8 |
| ATOM | 1333 | N | GLY | C | 300 | 12.146 | 47.836 | 22.389 | 1.00 | 25.96 | 7 |
| ATOM | 1334 | CA | GLY | C | 300 | 11.389 | 47.595 | 23.618 | 1.00 | 26.90 | 6 |
| ATOM | 1335 | C | GLY | C | 300 | 11.182 | 48.875 | 24.404 | 1.00 | 30.76 | 6 |
| ATOM | 1336 | O | GLY | C | 300 | 11.023 | 48.830 | 25.639 | 1.00 | 31.00 | 8 |
| ATOM | 1337 | N | LYS | C | 301 | 11.073 | 49.975 | 23.685 | 1.00 | 29.45 | 7 |
| ATOM | 1338 | CA | LYS | C | 301 | 10.905 | 51.285 | 24.343 | 1.00 | 33.22 | 6 |
| ATOM | 1339 | CB | LYS | C | 301 | 12.104 | 52.130 | 23.800 | 1.00 | 34.54 | 6 |
| ATOM | 1340 | CG | LYS | C | 301 | 13.438 | 51.692 | 24.356 | 1.00 | 45.39 | 6 |
| ATOM | 1341 | CD | LYS | C | 301 | 14.579 | 52.509 | 23.760 | 1.00 | 55.89 | 6 |
| ATOM | 1342 | CE | LYS | C | 301 | 15.883 | 52.152 | 24.454 | 1.00 | 63.37 | 6 |
| ATOM | 1343 | NZ | LYS | C | 301 | 15.809 | 50.819 | 25.114 | 1.00 | 64.44 | 7 |
| ATOM | 1344 | C | LYS | C | 301 | 9.716 | 52.056 | 23.798 | 1.00 | 34.37 | 6 |
| ATOM | 1345 | O | LYS | C | 301 | 9.632 | 53.265 | 24.050 | 1.00 | 41.72 | 8 |
| ATOM | 1346 | N | HIS | C | 302 | 8.910 | 51.471 | 22.953 | 1.00 | 34.82 | 7 |
| ATOM | 1347 | CA | HIS | C | 302 | 7.804 | 52.130 | 22.291 | 1.00 | 37.17 | 6 |
| ATOM | 1348 | CB | HIS | C | 302 | 7.209 | 51.176 | 21.276 | 1.00 | 36.32 | 6 |
| ATOM | 1349 | CG | HIS | C | 302 | 6.061 | 51.594 | 20.444 | 1.00 | 49.41 | 6 |
| ATOM | 1350 | CD2 | HIS | C | 302 | 5.233 | 52.660 | 20.480 | 1.00 | 59.81 | 6 |
| ATOM | 1351 | ND1 | HIS | C | 302 | 5.644 | 50.821 | 19.377 | 1.00 | 48.06 | 7 |
| ATOM | 1352 | CE1 | HIS | C | 302 | 4.594 | 51.386 | 18.808 | 1.00 | 59.89 | 6 |
| ATOM | 1353 | NE2 | HIS | C | 302 | 4.330 | 52.514 | 19.455 | 1.00 | 63.35 | 7 |
| ATOM | 1354 | C | HIS | C | 302 | 6.748 | 52.610 | 23.267 | 1.00 | 38.73 | 6 |
| ATOM | 1355 | O | HIS | C | 302 | 6.229 | 51.770 | 24.028 | 1.00 | 38.79 | 8 |
| ATOM | 1356 | OXT | HIS | C | 302 | 6.450 | 53.825 | 23.192 | 1.00 | 50.99 | 8 |
| ATOM | 1357 | OW | WAT | W | 1 | −4.224 | 33.423 | 34.144 | 1.00 | 53.27 | 8 |
| ATOM | 1358 | OW | WAT | W | 2 | 18.813 | 49.538 | 11.784 | 1.00 | 43.86 | 8 |
| ATOM | 1359 | OW | WAT | W | 3 | 18.261 | 39.681 | 10.865 | 1.00 | 39.76 | 8 |
| ATOM | 1360 | OW | WAT | W | 4 | 8.904 | 33.078 | 11.851 | 1.00 | 38.31 | 8 |
| ATOM | 1361 | OW | WAT | W | 5 | 4.199 | 60.972 | 19.377 | 1.00 | 52.52 | 8 |
| ATOM | 1362 | OW | WAT | W | 6 | 14.477 | 53.540 | 5.612 | 1.00 | 48.28 | 8 |
| ATOM | 1363 | OW | WAT | W | 7 | 11.280 | 35.102 | −0.408 | 1.00 | 43.88 | 8 |
| ATOM | 1364 | OW | WAT | W | 8 | 10.087 | 32.358 | 34.001 | 1.00 | 39.96 | 8 |
| ATOM | 1365 | OW | WAT | W | 9 | 15.416 | 57.414 | 13.859 | 1.00 | 48.04 | 8 |
| ATOM | 1366 | OW | WAT | W | 10 | 1.929 | 52.862 | 20.272 | 1.00 | 55.69 | 8 |
| ATOM | 1367 | OW | WAT | W | 11 | 4.935 | 60.748 | 16.928 | 1.00 | 39.08 | 8 |
| ATOM | 1368 | OW | WAT | W | 12 | −3.393 | 52.954 | −1.588 | 1.00 | 50.38 | 8 |
| ATOM | 1369 | OW | WAT | W | 13 | −13.253 | 36.368 | 20.479 | 1.00 | 42.42 | 8 |
| ATOM | 1370 | OW | WAT | W | 14 | 0.313 | 32.026 | 34.781 | 1.00 | 47.16 | 8 |
| ATOM | 1371 | OW | WAT | W | 15 | −6.564 | 45.853 | 14.770 | 1.00 | 68.25 | 8 |
| ATOM | 1372 | OW | WAT | W | 16 | 12.038 | 51.785 | 0.724 | 1.00 | 41.22 | 8 |
| ATOM | 1373 | OW | WAT | W | 17 | 14.999 | 64.994 | 4.375 | 1.00 | 48.22 | 8 |
| ATOM | 1374 | OW | WAT | W | 18 | 17.970 | 48.546 | 24.089 | 1.00 | 68.67 | 8 |
| ATOM | 1375 | OW | WAT | W | 19 | 18.217 | 40.214 | 24.483 | 1.00 | 47.37 | 8 |
| ATOM | 1376 | OW | WAT | W | 20 | 1.939 | 28.873 | 14.169 | 1.00 | 44.69 | 8 |
| ATOM | 1377 | OW | WAT | W | 21 | 3.847 | 66.616 | −1.008 | 1.00 | 44.63 | 8 |
| ATOM | 1378 | OW | WAT | W | 22 | −3.915 | 63.084 | 7.867 | 1.00 | 45.45 | 8 |
| ATOM | 1379 | OW | WAT | W | 23 | 19.360 | 45.486 | 31.250 | 1.00 | 63.22 | 8 |
| ATOM | 1380 | OW | WAT | W | 24 | 10.025 | 47.358 | 30.471 | 1.00 | 67.04 | 8 |
| ATOM | 1381 | OW | WAT | W | 25 | 13.664 | 53.469 | 2.124 | 1.00 | 42.64 | 8 |
| ATOM | 1382 | OW | WAT | W | 26 | −5.012 | 60.157 | −2.193 | 1.00 | 61.60 | 8 |

-continued

PDB FILE LISTING –cd81el.pdb

| ATOM | 1383 | OW | WAT | W | 27 | 6.815 | 67.394 | 21.507 | 1.00 | 52.80 | 8 |
|---|---|---|---|---|---|---|---|---|---|---|---|
| ATOM | 1384 | OW | WAT | W | 28 | 17.915 | 33.402 | 34.758 | 1.00 | 44.35 | 8 |
| ATOM | 1385 | OW | WAT | W | 29 | 16.731 | 42.979 | 3.382 | 1.00 | 84.13 | 8 |
| ATOM | 1386 | OW | WAT | W | 30 | −6.288 | 67.664 | 0.468 | 1.00 | 45.25 | 8 |
| ATOM | 1387 | OW | WAT | W | 31 | 7.402 | 62.280 | 10.335 | 1.00 | 42.54 | 8 |
| ATOM | 1388 | OW | WAT | W | 32 | 15.598 | 43.947 | 1.369 | 1.00 | 56.42 | 8 |
| ATOM | 1389 | OW | WAT | W | 33 | −7.926 | 47.819 | 12.072 | 1.00 | 44.03 | 8 |
| ATOM | 1390 | OW | WAT | W | 34 | 16.998 | 49.958 | 15.318 | 1.00 | 48.80 | 8 |
| ATOM | 1391 | OW | WAT | W | 35 | 8.586 | 64.846 | 22.173 | 1.00 | 69.56 | 8 |
| ATOM | 1392 | OW | WAT | W | 36 | −0.416 | 48.332 | 28.972 | 1.00 | 49.67 | 8 |
| ATOM | 1393 | OW | WAT | W | 37 | −1.687 | 35.124 | 10.272 | 1.00 | 51.02 | 8 |
| ATOM | 1394 | OW | WAT | W | 38 | 8.930 | 32.323 | 14.635 | 1.00 | 43.76 | 8 |
| ATOM | 1395 | OW | WAT | W | 39 | 14.596 | 53.388 | 26.734 | 1.00 | 54.53 | 8 |
| ATOM | 1396 | OW | WAT | W | 40 | −11.348 | 62.652 | 8.819 | 1.00 | 63.88 | 8 |
| ATOM | 1397 | OW | WAT | W | 41 | 3.903 | 62.050 | 15.465 | 1.00 | 38.48 | 8 |
| ATOM | 1398 | OW | WAT | W | 42 | −7.252 | 41.756 | 19.850 | 1.00 | 52.81 | 8 |
| ATOM | 1399 | OW | WAT | W | 43 | −1.996 | 56.577 | 17.341 | 1.00 | 59.40 | 8 |
| ATOM | 1400 | OW | WAT | W | 44 | 4.137 | 49.725 | 23.884 | 1.00 | 48.85 | 8 |
| ATOM | 1401 | OW | WAT | W | 45 | 15.737 | 51.416 | 6.167 | 1.00 | 38.54 | 8 |
| ATOM | 1402 | OW | WAT | W | 46 | −5.011 | 40.117 | 20.046 | 1.00 | 38.42 | 8 |
| ATOM | 1403 | OW | WAT | W | 47 | −13.873 | 33.451 | 19.673 | 1.00 | 42.16 | 8 |
| ATOM | 1404 | OW | WAT | W | 48 | 11.057 | 53.487 | −1.251 | 1.00 | 51.34 | 8 |
| ATOM | 1405 | OW | WAT | W | 49 | 14.300 | 48.217 | 26.182 | 1.00 | 45.81 | 8 |
| ATOM | 1406 | OW | WAT | W | 50 | 12.120 | 58.997 | −1.940 | 1.00 | 63.88 | 8 |
| ATOM | 1407 | OW | WAT | W | 51 | −0.336 | 33.581 | 11.855 | 1.00 | 48.03 | 8 |
| ATOM | 1408 | OW | WAT | W | 52 | 16.829 | 63.174 | 4.226 | 1.00 | 48.59 | 8 |
| ATOM | 1409 | OW | WAT | W | 53 | 16.022 | 41.438 | 23.130 | 1.00 | 41.43 | 8 |
| ATOM | 1410 | OW | WAT | W | 54 | −15.200 | 36.945 | 22.654 | 1.00 | 28.98 | 8 |
| ATOM | 1411 | OW | WAT | W | 55 | 13.277 | 40.851 | 6.595 | 1.00 | 29.49 | 8 |
| ATOM | 1412 | OW | WAT | W | 56 | 12.069 | 61.338 | 14.855 | 1.00 | 27.04 | 8 |
| ATOM | 1413 | OW | WAT | W | 57 | 3.227 | 32.023 | 23.771 | 1.00 | 30.91 | 8 |
| ATOM | 1414 | OW | WAT | W | 58 | 9.562 | 62.631 | 0.352 | 1.00 | 32.41 | 8 |
| ATOM | 1415 | OW | WAT | W | 59 | 6.585 | 69.144 | 1.589 | 1.00 | 39.21 | 8 |
| ATOM | 1416 | OW | WAT | W | 60 | 5.345 | 68.911 | −0.882 | 1.00 | 44.18 | 8 |
| ATOM | 1417 | OW | WAT | W | 61 | −0.751 | 50.368 | 19.292 | 1.00 | 32.73 | 8 |
| ATOM | 1418 | OW | WAT | W | 62 | 17.617 | 40.863 | 26.974 | 1.00 | 32.29 | 8 |
| ATOM | 1419 | OW | WAT | W | 63 | 1.179 | 39.116 | 32.520 | 1.00 | 34.20 | 8 |
| ATOM | 1420 | OW | WAT | W | 64 | −3.110 | 37.236 | 22.171 | 1.00 | 33.88 | 8 |
| ATOM | 1421 | OW | WAT | W | 65 | 14.044 | 57.099 | 4.209 | 1.00 | 33.65 | 8 |
| ATOM | 1422 | OW | WAT | W | 66 | 15.989 | 40.653 | 9.396 | 1.00 | 30.96 | 8 |
| ATOM | 1423 | OW | WAT | W | 67 | 5.371 | 35.579 | 5.640 | 1.00 | 34.67 | 8 |
| ATOM | 1424 | OW | WAT | W | 68 | −4.275 | 34.135 | 21.863 | 1.00 | 40.99 | 8 |
| ATOM | 1425 | OW | WAT | W | 69 | −10.323 | 38.406 | 25.608 | 1.00 | 36.01 | 8 |
| ATOM | 1426 | OW | WAT | W | 70 | −2.810 | 46.901 | 24.190 | 1.00 | 39.93 | 8 |
| ATOM | 1427 | OW | WAT | W | 71 | 13.870 | 64.852 | 12.989 | 1.00 | 34.39 | 8 |
| ATOM | 1428 | OW | WAT | W | 72 | 4.793 | 27.473 | 30.299 | 1.00 | 46.24 | 8 |
| ATOM | 1429 | OW | WAT | W | 73 | −15.971 | 32.066 | 20.578 | 1.00 | 38.92 | 8 |
| ATOM | 1430 | OW | WAT | W | 74 | 5.399 | 34.420 | 8.086 | 1.00 | 39.29 | 8 |
| ATOM | 1431 | OW | WAT | W | 75 | −0.519 | 32.450 | 14.342 | 1.00 | 33.68 | 8 |
| ATOM | 1432 | OW | WAT | W | 76 | 2.179 | 32.697 | 11.146 | 1.00 | 36.98 | 8 |
| ATOM | 1433 | OW | WAT | W | 77 | 10.170 | 56.080 | −0.241 | 1.00 | 39.89 | 8 |
| ATOM | 1434 | OW | WAT | W | 78 | 5.714 | 48.333 | 1.212 | 1.00 | 37.11 | 8 |
| ATOM | 1435 | OW | WAT | W | 79 | −4.290 | 33.857 | 16.226 | 1.00 | 37.36 | 8 |
| ATOM | 1436 | OW | WAT | W | 80 | 2.780 | 25.857 | 19.866 | 1.00 | 36.02 | 8 |
| ATOM | 1437 | OW | WAT | W | 81 | 12.798 | 43.202 | 2.474 | 1.00 | 34.74 | 8 |
| ATOM | 1438 | OW | WAT | W | 82 | −7.897 | 39.332 | 18.472 | 1.00 | 41.75 | 8 |
| ATOM | 1439 | OW | WAT | W | 83 | 16.117 | 44.618 | 21.247 | 1.00 | 31.97 | 8 |
| ATOM | 1440 | OW | WAT | W | 84 | 11.055 | 65.023 | 0.596 | 1.00 | 38.11 | 8 |
| ATOM | 1441 | OW | WAT | W | 85 | 12.824 | 45.673 | 3.486 | 1.00 | 33.54 | 8 |
| ATOM | 1442 | OW | WAT | W | 86 | 15.100 | 60.207 | 1.681 | 1.00 | 45.21 | 8 |
| ATOM | 1443 | OW | WAT | W | 87 | −4.960 | 50.919 | 0.707 | 1.00 | 47.99 | 8 |
| ATOM | 1444 | OW | WAT | W | 88 | 9.128 | 42.918 | 32.795 | 1.00 | 44.27 | 8 |
| ATOM | 1445 | OW | WAT | W | 89 | 9.762 | 58.054 | 20.187 | 1.00 | 47.67 | 8 |
| ATOM | 1446 | OW | WAT | W | 90 | 12.540 | 34.153 | 9.788 | 1.00 | 45.77 | 8 |
| ATOM | 1447 | OW | WAT | W | 91 | 17.905 | 51.635 | 10.678 | 1.00 | 40.67 | 8 |
| ATOM | 1448 | OW | WAT | W | 92 | −3.398 | 39.623 | 8.128 | 1.00 | 45.41 | 8 |
| ATOM | 1449 | OW | WAT | W | 93 | 6.924 | 42.895 | −0.650 | 1.00 | 42.91 | 8 |
| ATOM | 1450 | OW | WAT | W | 94 | 7.797 | 55.535 | 21.646 | 1.00 | 50.17 | 8 |
| ATOM | 1451 | OW | WAT | W | 95 | 12.822 | 64.411 | 2.584 | 1.00 | 37.53 | 8 |
| ATOM | 1452 | OW | WAT | W | 96 | 10.955 | 46.835 | −5.508 | 1.00 | 45.36 | 8 |
| ATOM | 1453 | OW | WAT | W | 97 | 13.257 | 59.487 | 9.888 | 1.00 | 36.34 | 8 |
| ATOM | 1454 | OW | WAT | W | 98 | 14.865 | 39.030 | 19.548 | 1.00 | 41.41 | 8 |
| ATOM | 1455 | OW | WAT | W | 99 | −2.138 | 41.902 | 25.462 | 1.00 | 41.60 | 8 |
| ATOM | 1456 | OW | WAT | W | 100 | −3.706 | 31.806 | 24.679 | 1.00 | 40.94 | 8 |
| ATOM | 1457 | OW | WAT | W | 101 | 5.836 | 33.167 | 1.082 | 1.00 | 43.31 | 8 |
| ATOM | 1458 | OW | WAT | W | 102 | 23.483 | 39.507 | 35.275 | 1.00 | 57.98 | 8 |
| ATOM | 1459 | OW | WAT | W | 103 | 17.559 | 63.021 | 7.407 | 1.00 | 50.25 | 8 |

-continued

PDB FILE LISTING –cd81el.pdb

| ATOM | 1460 | OW | WAT | W | 104 | 19.056 | 43.139 | 28.930 | 1.00 | 42.00 | 8 |
| ATOM | 1461 | OW | WAT | W | 105 | 19.572 | 41.453 | 18.032 | 1.00 | 45.63 | 8 |
| ATOM | 1462 | OW | WAT | W | 106 | 6.525 | 39.243 | −0.417 | 1.00 | 40.74 | 8 |
| ATOM | 1463 | OW | WAT | W | 107 | 3.627 | 31.518 | 12.831 | 1.00 | 38.63 | 8 |
| ATOM | 1464 | OW | WAT | W | 108 | 5.366 | 58.591 | 23.270 | 1.00 | 55.71 | 8 |
| ATOM | 1465 | OW | WAT | W | 109 | −0.088 | 26.458 | 16.764 | 1.00 | 52.60 | 8 |
| ATOM | 1466 | OW | WAT | W | 110 | 17.119 | 48.571 | −9.546 | 1.00 | 47.91 | 8 |
| ATOM | 1467 | OW | WAT | W | 111 | 1.096 | 44.692 | 2.583 | 1.00 | 40.04 | 8 |
| ATOM | 1468 | OW | WAT | W | 112 | 16.042 | 35.471 | 8.298 | 1.00 | 50.36 | 8 |
| ATOM | 1469 | OW | WAT | W | 113 | 12.648 | 35.159 | 33.701 | 1.00 | 39.34 | 8 |
| ATOM | 1470 | OW | WAT | W | 114 | 3.337 | 49.000 | −0.094 | 1.00 | 52.85 | 8 |
| ATOM | 1471 | OW | WAT | W | 115 | 20.033 | 39.068 | 22.889 | 1.00 | 58.35 | 8 |
| ATOM | 1472 | OW | WAT | W | 116 | 10.097 | 47.403 | 34.472 | 1.00 | 58.00 | 8 |
| ATOM | 1473 | OW | WAT | W | 117 | 10.830 | 41.416 | −3.209 | 1.00 | 41.27 | 8 |
| ATOM | 1474 | OW | WAT | W | 118 | 12.754 | 36.719 | 35.635 | 1.00 | 54.11 | 8 |
| ATOM | 1475 | OW | WAT | W | 119 | −0.813 | 31.338 | 21.906 | 1.00 | 46.66 | 8 |
| ATOM | 1476 | OW | WAT | W | 120 | 3.965 | 25.061 | 22.618 | 1.00 | 44.72 | 8 |
| ATOM | 1477 | OW | WAT | W | 121 | 13.777 | 59.149 | 13.305 | 1.00 | 41.18 | 8 |
| ATOM | 1478 | OW | WAT | W | 122 | 4.277 | 55.533 | 20.931 | 1.00 | 46.53 | 8 |
| ATOM | 1479 | OW | WAT | W | 123 | −7.345 | 30.636 | 20.890 | 1.00 | 46.01 | 8 |
| ATOM | 1480 | OW | WAT | W | 124 | 16.037 | 45.847 | −5.475 | 1.00 | 50.06 | 8 |
| ATOM | 1481 | OW | WAT | W | 125 | −3.061 | 47.338 | 18.259 | 1.00 | 41.61 | 8 |
| ATOM | 1482 | OW | WAT | W | 126 | 10.453 | 31.620 | 10.805 | 1.00 | 50.39 | 8 |
| ATOM | 1483 | OW | WAT | W | 127 | 17.496 | 40.971 | 20.796 | 1.00 | 55.25 | 8 |
| ATOM | 1484 | OW | WAT | W | 128 | −6.207 | 32.805 | 19.155 | 1.00 | 58.66 | 8 |
| ATOM | 1485 | OW | WAT | W | 129 | 16.601 | 45.869 | −1.260 | 1.00 | 59.55 | 8 |
| ATOM | 1486 | OW | WAT | W | 130 | 2.484 | 51.452 | 22.049 | 1.00 | 47.45 | 8 |
| ATOM | 1487 | OW | WAT | W | 131 | 11.516 | 67.657 | 23.120 | 1.00 | 55.77 | 8 |
| ATOM | 1488 | OW | WAT | W | 132 | 5.346 | 61.188 | 13.510 | 1.00 | 29.53 | 8 |
| ATOM | 1489 | OW | WAT | W | 133 | 13.484 | 40.850 | 3.961 | 1.00 | 38.04 | 8 |
| ATOM | 1490 | OW | WAT | W | 134 | 6.017 | 48.953 | 24.748 | 1.00 | 98.99 | 8 |
| ATOM | 1491 | OW | WAT | W | 135 | 12.715 | 45.073 | 31.090 | 1.00 | 47.26 | 8 |
| ATOM | 1492 | OW | WAT | W | 136 | 8.319 | 40.420 | −2.773 | 1.00 | 47.04 | 8 |
| ATOM | 1493 | OW | WAT | W | 137 | −8.731 | 32.859 | 33.302 | 1.00 | 49.10 | 8 |
| ATOM | 1494 | OW | WAT | W | 138 | 15.813 | 48.959 | 17.249 | 1.00 | 53.10 | 8 |
| ATOM | 1495 | OW | WAT | W | 139 | −15.705 | 39.364 | 21.958 | 1.00 | 63.55 | 8 |
| ATOM | 1496 | OW | WAT | W | 140 | −5.095 | 45.138 | 17.428 | 1.00 | 45.00 | 8 |
| ATOM | 1497 | OW | WAT | W | 141 | −13.312 | 30.683 | 20.947 | 1.00 | 53.07 | 8 |
| ATOM | 1498 | OW | WAT | W | 142 | −13.192 | 60.851 | 8.504 | 1.00 | 52.13 | 8 |
| ATOM | 1499 | OW | WAT | W | 143 | 23.328 | 40.686 | 16.795 | 1.00 | 47.26 | 8 |
| ATOM | 1500 | OW | WAT | W | 144 | 13.616 | 60.813 | 17.279 | 1.00 | 43.28 | 8 |
| ATOM | 1501 | OW | WAT | W | 145 | 12.017 | 47.329 | −3.100 | 1.00 | 48.09 | 8 |
| ATOM | 1502 | OW | WAT | W | 146 | 10.595 | 61.299 | −1.506 | 1.00 | 49.06 | 8 |
| ATOM | 1503 | OW | WAT | W | 147 | 8.027 | 61.147 | −4.069 | 1.00 | 52.20 | 8 |
| ATOM | 1504 | OW | WAT | W | 148 | −6.283 | 49.644 | 10.949 | 1.00 | 57.39 | 8 |
| ATOM | 1505 | OW | WAT | W | 149 | −9.469 | 40.692 | 26.922 | 1.00 | 43.53 | 8 |
| ATOM | 1506 | OW | WAT | W | 150 | 19.210 | 50.226 | 21.171 | 1.00 | 58.41 | 8 |
| ATOM | 1507 | OW | WAT | W | 151 | 2.611 | 26.546 | 15.184 | 1.00 | 50.95 | 8 |
| ATOM | 1508 | OW | WAT | W | 152 | 3.965 | 46.489 | −3.009 | 1.00 | 57.99 | 8 |
| ATOM | 1509 | OW | WAT | W | 153 | 16.271 | 55.882 | 11.030 | 1.00 | 48.24 | 8 |
| ATOM | 1510 | OW | WAT | W | 154 | 1.184 | 67.205 | −1.174 | 1.00 | 47.38 | 8 |
| ATOM | 1511 | OW | WAT | W | 155 | 2.482 | 46.558 | 0.974 | 1.00 | 67.17 | 8 |
| ATOM | 1512 | OW | WAT | W | 156 | 11.027 | 55.889 | 23.958 | 1.00 | 54.67 | 8 |
| ATOM | 1513 | OW | WAT | W | 157 | −4.446 | 30.923 | 22.181 | 1.00 | 62.18 | 8 |
| ATOM | 1514 | OW | WAT | W | 158 | −3.844 | 44.313 | 24.890 | 1.00 | 42.34 | 8 |
| ATOM | 1515 | OW | WAT | W | 159 | 14.549 | 53.163 | 20.560 | 1.00 | 49.30 | 8 |
| ATOM | 1516 | OW | WAT | W | 160 | −3.797 | 31.575 | 19.705 | 1.00 | 69.49 | 8 |
| ATOM | 1517 | OW | WAT | W | 161 | 6.756 | 25.504 | 17.575 | 1.00 | 49.43 | 8 |
| ATOM | 1518 | OW | WAT | W | 162 | 10.788 | 30.257 | 35.433 | 1.00 | 36.60 | 8 |
| ATOM | 1519 | OW | WAT | W | 163 | 21.237 | 50.223 | 9.133 | 1.00 | 56.25 | 8 |
| ATOM | 1520 | OW | WAT | W | 164 | −6.177 | 45.663 | 3.966 | 1.00 | 58.49 | 8 |
| ATOM | 1521 | OW | WAT | W | 165 | −1.644 | 33.990 | 22.144 | 1.00 | 32.61 | 8 |
| ATOM | 1522 | OW | WAT | W | 166 | 20.594 | 39.565 | 9.528 | 1.00 | 54.57 | 8 |
| ATOM | 1523 | OW | WAT | W | 167 | 15.964 | 59.646 | 9.793 | 1.00 | 50.70 | 8 |
| ATOM | 1524 | OW | WAT | W | 168 | 7.316 | 50.423 | 25.713 | 1.00 | 47.49 | 8 |
| ATOM | 1525 | OW | WAT | W | 169 | 23.295 | 32.789 | 15.200 | 1.00 | 57.39 | 8 |
| ATOM | 1526 | OW | WAT | W | 170 | −6.898 | 46.350 | 20.730 | 1.00 | 50.13 | 8 |
| ATOM | 1527 | OW | WAT | W | 171 | −8.760 | 52.976 | −3.940 | 1.00 | 55.95 | 8 |
| ATOM | 1528 | OW | WAT | W | 172 | −2.895 | 48.110 | 26.454 | 1.00 | 68.31 | 8 |
| ATOM | 1529 | OW | WAT | W | 173 | −1.144 | 71.221 | 17.499 | 1.00 | 50.95 | 8 |
| ATOM | 1530 | OW | WAT | W | 174 | 12.604 | 56.338 | 22.115 | 1.00 | 55.77 | 8 |
| ATOM | 1531 | OW | WAT | W | 175 | 22.778 | 50.987 | 6.750 | 1.00 | 51.42 | 8 |
| ATOM | 1532 | OW | WAT | W | 176 | 9.430 | 60.647 | −6.523 | 1.00 | 61.73 | 8 |
| ATOM | 1533 | OW | WAT | W | 177 | 15.767 | 60.697 | 14.713 | 1.00 | 61.57 | 8 |
| ATOM | 1534 | OW | WAT | W | 178 | 22.291 | 46.306 | 8.351 | 1.00 | 64.25 | 8 |
| ATOM | 1535 | OW | WAT | W | 179 | 14.393 | 57.247 | 1.565 | 1.00 | 50.53 | 8 |
| ATOM | 1536 | OW | WAT | W | 180 | 6.277 | 72.244 | 1.677 | 1.00 | 56.50 | 8 |

-continued

| PDB FILE LISTING – cd81el.pdb | | | | | | | | | |
|---|---|---|---|---|---|---|---|---|---|
| ATOM | 1537 | OW | WAT | W | 181 | −5.357 | 56.977 | 16.549 | 1.00 | 63.38 | 8 |
| ATOM | 1538 | OW | WAT | W | 182 | 20.252 | 47.811 | 25.759 | 1.00 | 59.54 | 8 |
| ATOM | 1539 | OW | WAT | W | 183 | −0.767 | 65.909 | −2.025 | 1.00 | 59.74 | 8 |
| ATOM | 1540 | OW | WAT | W | 184 | 8.023 | 52.581 | −3.823 | 1.00 | 57.61 | 8 |
| ATOM | 1541 | OW | WAT | W | 185 | 22.973 | 31.298 | 13.186 | 1.00 | 61.46 | 8 |
| ATOM | 1542 | OW | WAT | W | 186 | 21.890 | 46.952 | 18.566 | 1.00 | 62.99 | 8 |
| ATOM | 1543 | OW | WAT | W | 187 | 12.545 | 56.301 | −0.180 | 1.00 | 62.12 | 8 |
| ATOM | 1544 | OW | WAT | W | 188 | 0.899 | 33.958 | 8.083 | 1.00 | 52.91 | 8 |
| ATOM | 1545 | OW | WAT | W | 189 | −4.871 | 46.670 | 29.841 | 1.00 | 66.19 | 8 |
| ATOM | 1546 | OW | WAT | W | 190 | −1.898 | 31.738 | 34.170 | 1.00 | 52.17 | 8 |
| ATOM | 1547 | OW | WAT | W | 191 | −1.189 | 41.151 | 2.866 | 1.00 | 53.86 | 8 |
| ATOM | 1548 | OW | WAT | W | 192 | 22.565 | 44.586 | 11.059 | 1.00 | 62.34 | 8 |
| ATOM | 1549 | OW | WAT | W | 193 | −5.244 | 44.118 | 13.781 | 1.00 | 60.66 | 8 |
| ATOM | 1550 | OW | WAT | W | 194 | 5.422 | 49.607 | −0.947 | 1.00 | 53.84 | 8 |
| END | | | | | | | | | | | |

The invention claimed is:

1. A method for identifying a ligand for the large extracellular loop of CD81, comprising the steps of (a) providing a 3D structural representation of the large extracellular loop of CD81, wherein the 3D structural representation comprises a D helix having a residue Phe186, and wherein the 3D structural representation of the large extracellular loop of CD81 is set forth in the atomic co-ordinates of Table 1, or variants of the atomic co-ordinates of Table 1 thereof, in which the r.m.s. deviation of the x, y and z co-ordinates for all heavy atoms is less than 2.5 Å; (b) providing a 3D structural representation of a potential ligand; (c) using a computer to dock the 3D structural representation of the potential ligand with the 3D structural representation of the large extracellular loop of CD81 at a site comprising the residue Phe186, wherein a potential ligand that docks with the large extracellular loop of CD81 at the site comprising the residue Phe186 is identified as a ligand for the large extracellular loop of CD81; (d) contacting the ligand identified in step (c) with CD81 or a fragment thereof containing the large extracellular loop, and (e) assaying the interaction between the ligand and CD81 or the fragment thereof containing the large extracellular loop to determine whether the ligand identified in step (c) is a ligand for the large extracellular loop of CD81.

2. The method of claim 1, wherein using the computer to dock the 3D structural representations of the potential ligand with the 3D structural representation of the large extracellular loop of CD81 comprises geometric matching or minimising the energy of interaction between the ligand and the large extracellular loop of CD81.

3. The method of claim 2, wherein the step of using the computer to dock the potential ligand with the large extracellular loop of CD81 comprises screening members of a structural library of potential ligands to identify a ligand for CD81.

4. The method of claim 1, further comprising comparing the structures of the ligand identified in step (c), thereby defining a pharmacophore.

5. The method of claim 4, wherein the pharmacophore is used in de novo drug design.

6. The method of claim 1, wherein the 3D structural representation of the large extracellular loop of CD81 includes van der Waals contacts, electrostatic interactions, and/or hydrogen bonding opportunities on the CD81 surface.

7. The method of claim 1, wherein the site comprising the residue Phe186 further comprises one or more of Leu154, Thr163, Ile181, Ile182, Leu185, Glu188, and Asp196.

8. The method of claim 1, wherein the site comprising the residue Phe186 is the D-helix region Asn180-Phe186.

9. A method for identifying a ligand for the large extracellular loop of CD81, comprising:

(a) contacting a ligand with CD81 or a fragment thereof containing the large extracellular loop, and (b) assaying the interaction between the ligand and CD81 or the fragment thereof containing the large extracellular loop to determine whether the ligand is a ligand for CD81, wherein the ligand of step (a) was identified by a method comprising:

providing a 3D structural representation of the large extracellular loop of CD81, wherein the 3D structural representation comprises a D helix having a residue Phe186, and wherein the 3D structural representation of the large extracellular loop of CD81 is set forth in the atomic co-ordinates of Table 1, or variants of the atomic co-ordinates of Table 1, in which the r.m.s. deviation of the x, y and z co-ordinates for all heavy atoms is less than 2.5 Å;

providing a 3D structural representation of a potential ligand;

using a computer to dock the 3D structural representation of the potential ligand with the 3D structural representation of the large extracellular loop of CD81 at a site comprising the residue Phe186, wherein a potential ligand that docks with the large extracellular loop of CD81 at a site comprising the residue Phe186 is identified as a ligand for the large extracellular loop of CD81.

10. The method of claim 9, wherein the site comprising the residue Phe186 further comprises one or more of Leu154, Thr163, Ile181, Ile182, Leu185, Glu188, and Asp196.

11. The method of claim 9, wherein the site comprising the residue Phe186 is the D-helix region Asn180-Phe186.

* * * * *

UNITED STATES PATENT AND TRADEMARK OFFICE
CERTIFICATE OF CORRECTION

PATENT NO. : 7,657,385 B2  Page 1 of 1
APPLICATION NO. : 10/312490
DATED : February 2, 2010
INVENTOR(S) : Bolognesi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 581 days.

Signed and Sealed this

Thirtieth Day of November, 2010

David J. Kappos
*Director of the United States Patent and Trademark Office*